(12) United States Patent
Harrison et al.

(10) Patent No.: US 9,999,418 B2
(45) Date of Patent: Jun. 19, 2018

(54) MEDICAL DEVICE HAVING A POSITION INDICATOR

(71) Applicant: Anchor Orthopedics XT Inc., Mississauga (CA)

(72) Inventors: Robert Harrison, Milton (CA); Jeffery Arnett, Gilbert, AZ (US); Neil Godara, Milton (CA); Laura Man Yee Yu, Markham (CA)

(73) Assignee: Anchor Orthopedics XT Inc., Mississauga (CA)

( * ) Notice: Subject to any disclaimer, the term of this patent is extended or adjusted under 35 U.S.C. 154(b) by 0 days. days.

(21) Appl. No.: 15/056,810

(22) Filed: Feb. 29, 2016

(65) Prior Publication Data

US 2016/0249907 A1 Sep. 1, 2016

Related U.S. Application Data

(63) Continuation-in-part of application No. 13/589,151, filed on Aug. 19, 2012, now Pat. No. 9,271,724, and
(Continued)

(51) Int. Cl.
*A61B 17/34* (2006.01)
*A61B 17/04* (2006.01)
(Continued)

(52) U.S. Cl.
CPC ...... *A61B 17/0469* (2013.01); *A61B 17/0482* (2013.01); *A61B 17/062* (2013.01);
(Continued)

(58) Field of Classification Search
CPC ........ A61B 5/150885; A61B 5/150893; A61B 5/1509; A61B 5/150908; A61B 5/150923;
(Continued)

(56) References Cited

U.S. PATENT DOCUMENTS 6,641,592 B1 11/2003 Sauer et al.
7,407,505 B2 8/2008 Sauer et al.
(Continued)

FOREIGN PATENT DOCUMENTS

WO 2009053986 A2 4/2009
WO 2010085793 A2 7/2010

*Primary Examiner* — Jonathan Miles
(74) *Attorney, Agent, or Firm* — Nir Lifshitz; Glenn Arnold

(57) ABSTRACT

A medical device is described, the medical device comprising a moveable member, moveable between a first position and a second position; an actuating member coupled to the moveable member, directly or indirectly, for manipulating the moveable member, that is for causing the movement of the moveable member; and an indicator mechanism coupled, directly or indirectly, to the actuating member, said indicator mechanism comprising at least two components that interact to produce an indication; the indicator and actuating member being cooperatively operable such that the interaction between the at least two components of the indicator mechanism occurs automatically to automatically indicate advancement of the moveable member to the second position from the first position upon a predetermined actuation of the actuating member.

14 Claims, 44 Drawing Sheets

Related U.S. Application Data a continuation-in-part of application No. 14/238,945, filed as application No. PCT/IB2012/054204 on Aug. 17, 2012.

(60) Provisional application No. 61/524,765, filed on Aug. 18, 2011, provisional application No. 61/524,766, filed on Aug. 18, 2011, provisional application No. 61/561,486, filed on Nov. 18, 2011, provisional application No. 61/582,464, filed on Jan. 2, 2012, provisional application No. 61/586,287, filed on Jan. 13, 2012, provisional application No. 61/593,843, filed on Feb. 1, 2012, provisional application No. 61/597,449, filed on Feb. 10, 2012.

(51) Int. Cl.
| | |
|---|---|
| *A61B 17/062* | (2006.01) |
| *A61B 90/00* | (2016.01) |
| *A61B 17/00* | (2006.01) |
| *A61B 17/06* | (2006.01) |

(52) U.S. Cl.
CPC ........... *A61B 2017/00455* (2013.01); *A61B 2017/0475* (2013.01); *A61B 2017/0496* (2013.01); *A61B 2017/06052* (2013.01); *A61B 2090/0811* (2016.02)

(58) Field of Classification Search
CPC . A61B 17/0469; A61B 17/0482; A61B 17/06; A61B 2019/4857
See application file for complete search history.

(56) References Cited

U.S. PATENT DOCUMENTS

| | | | |
|---|---|---|---|
| 7,731,727 B2 | 6/2010 | Sauer | |
| 2003/0208139 A1* | 11/2003 | Crawford | A61B 5/150351 600/576 |
| 2009/0030442 A1* | 1/2009 | Potter | A61B 5/1411 606/182 |
| 2010/0211082 A1 | 8/2010 | Sauer | |

\* cited by examiner

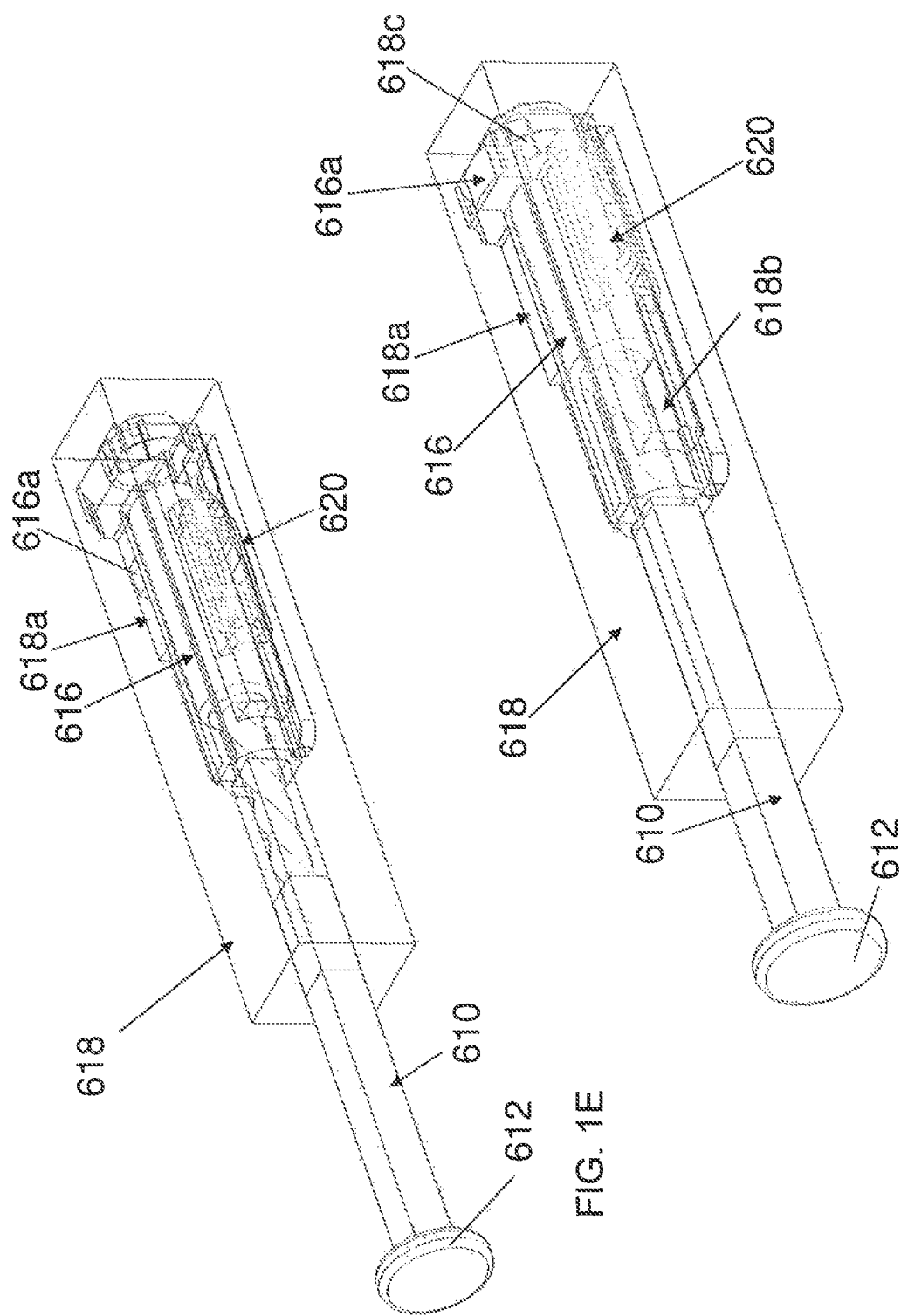

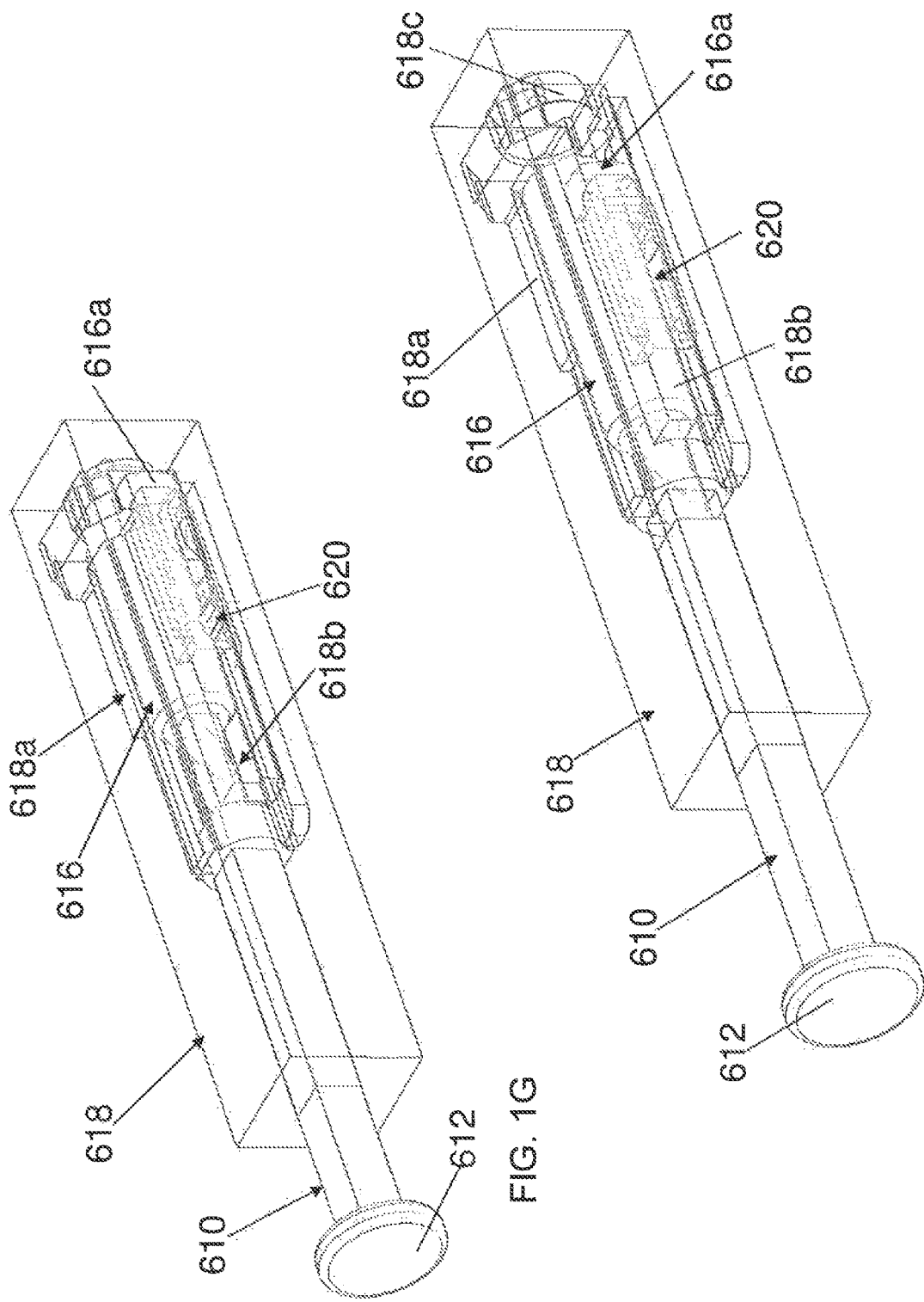

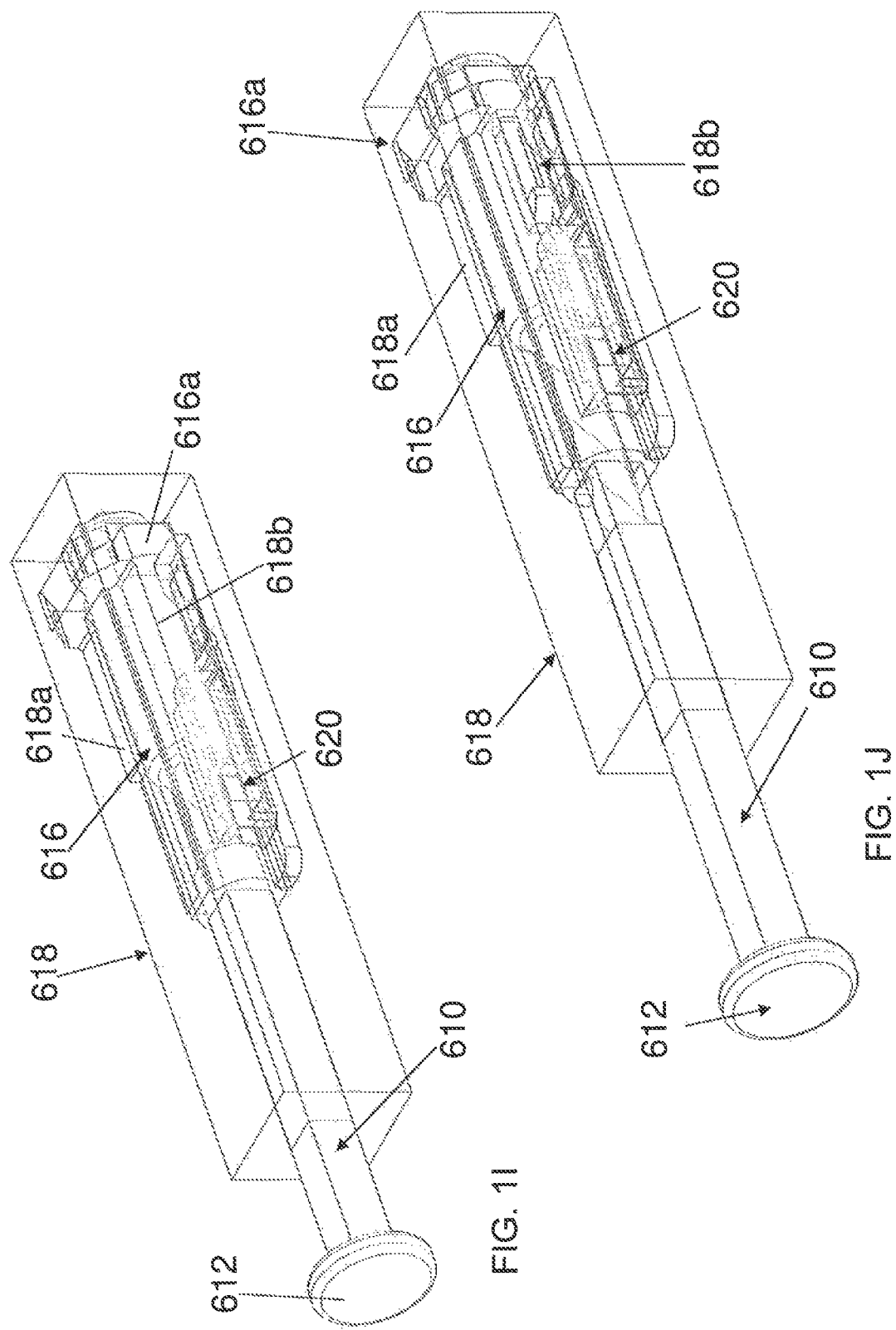

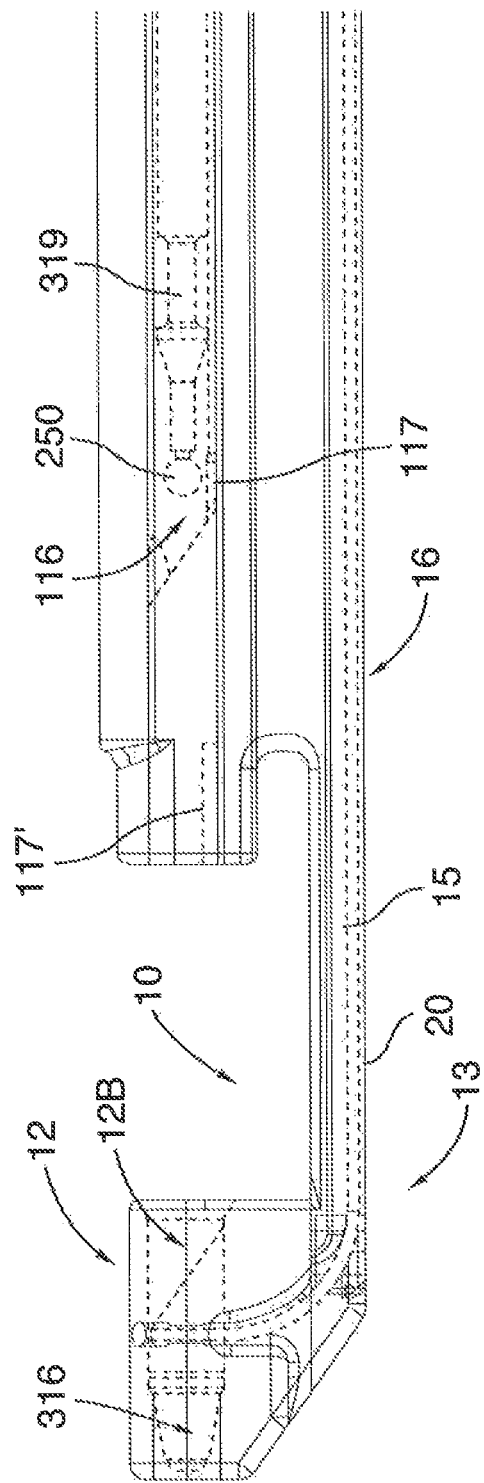

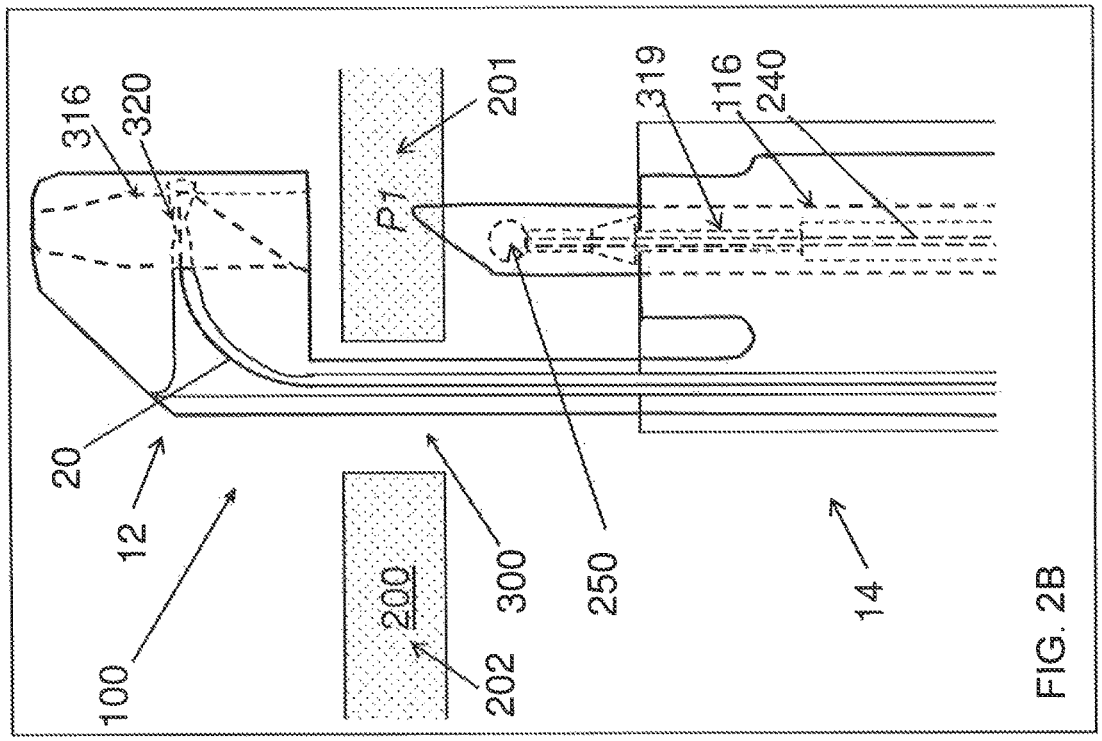
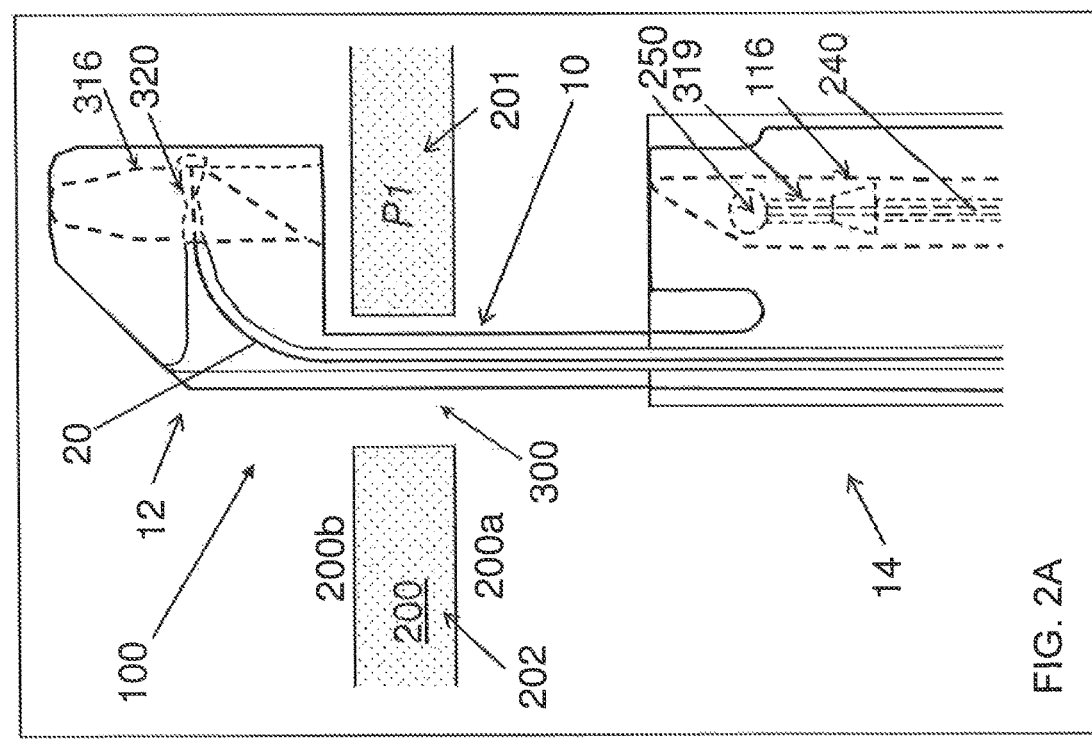

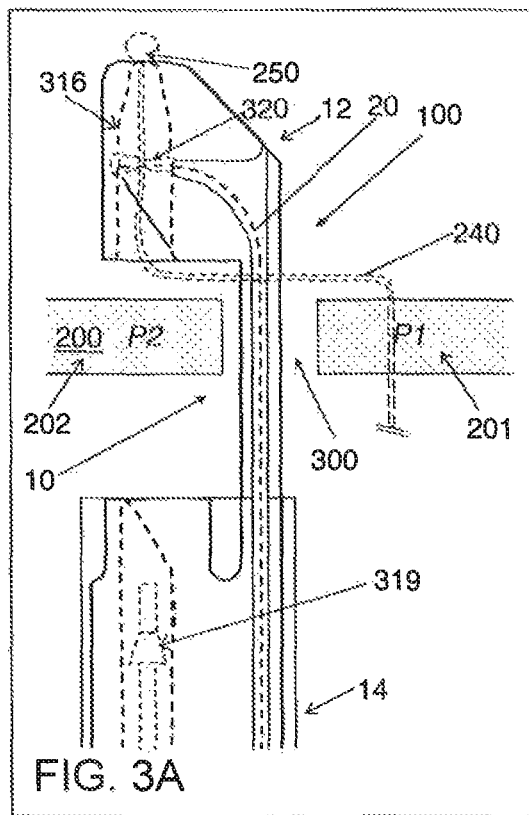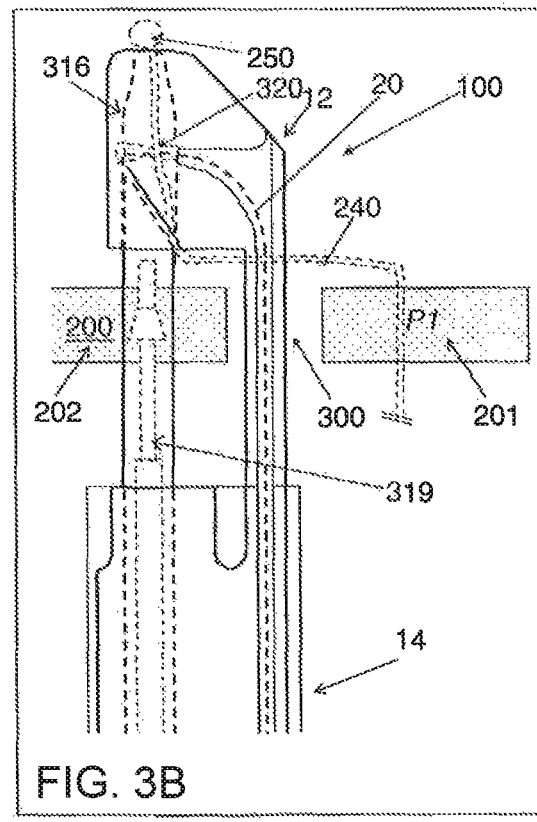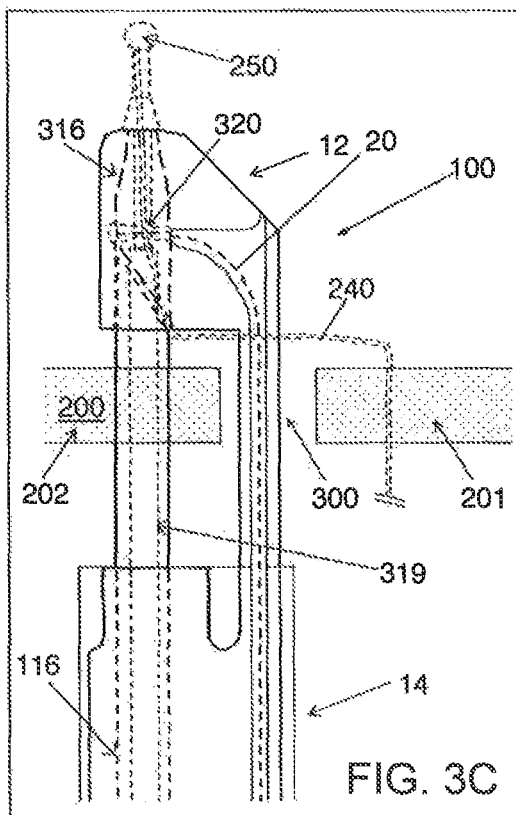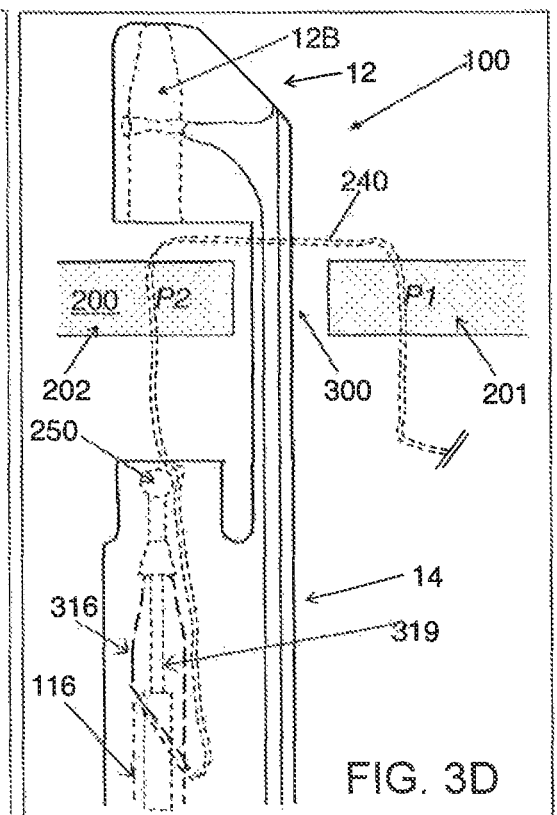

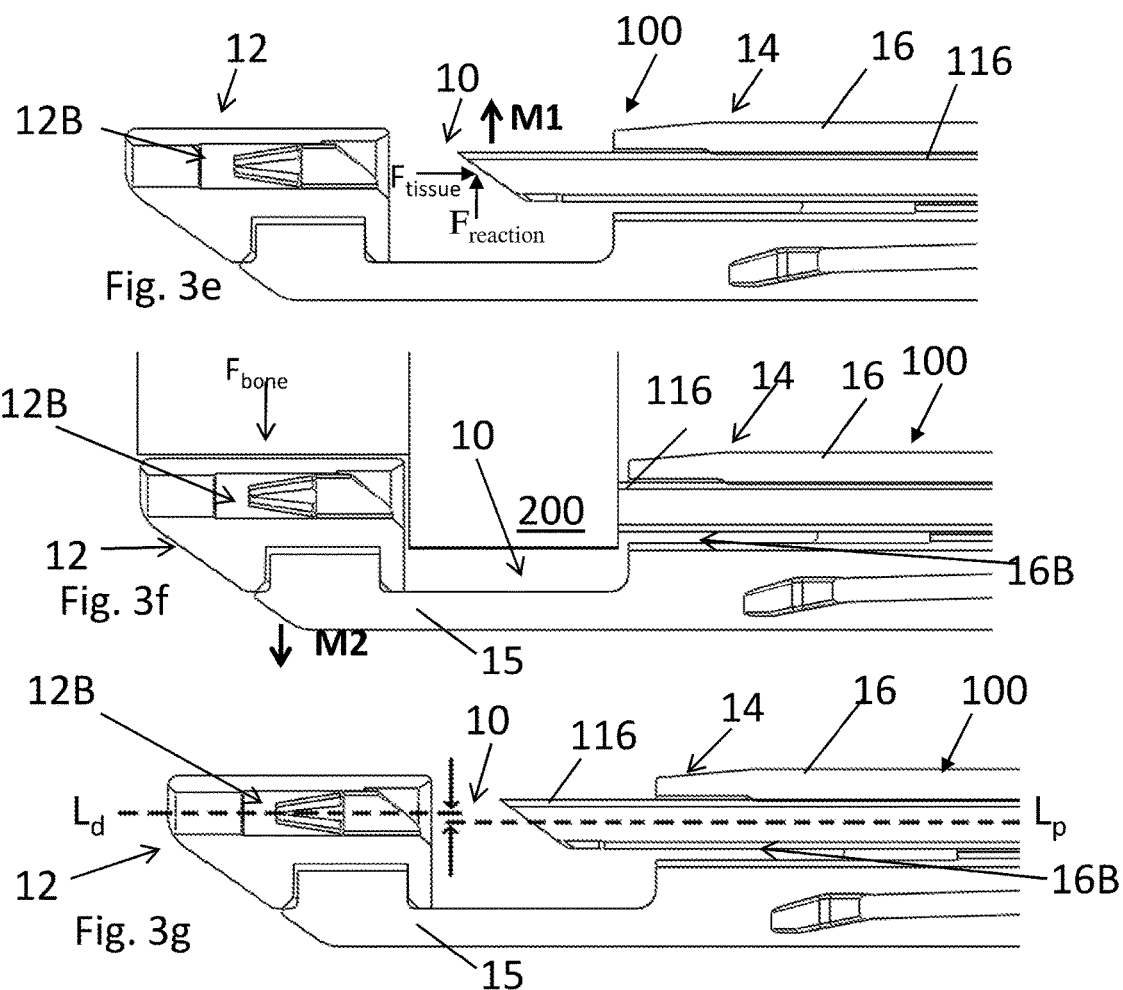

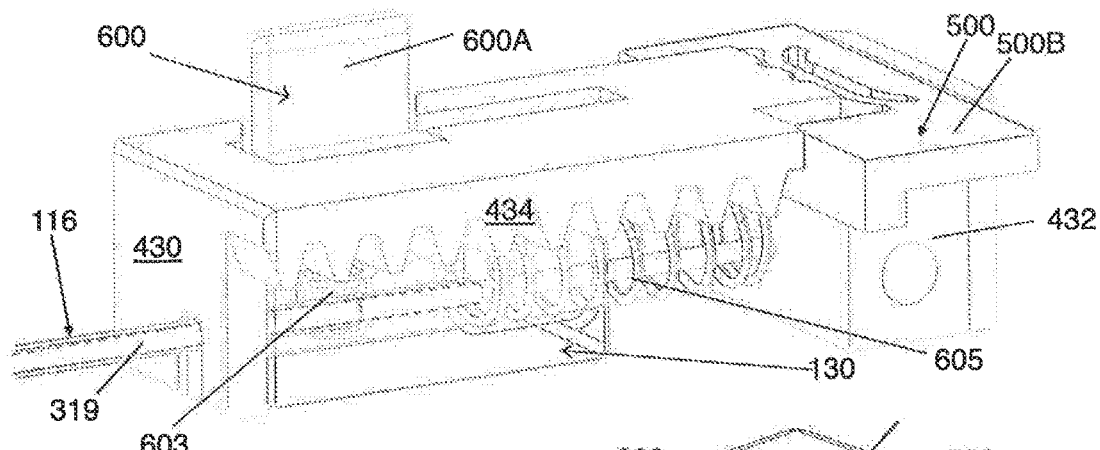
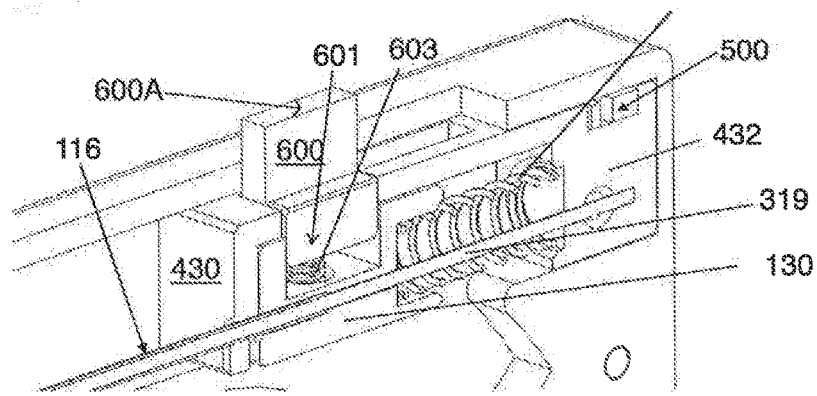
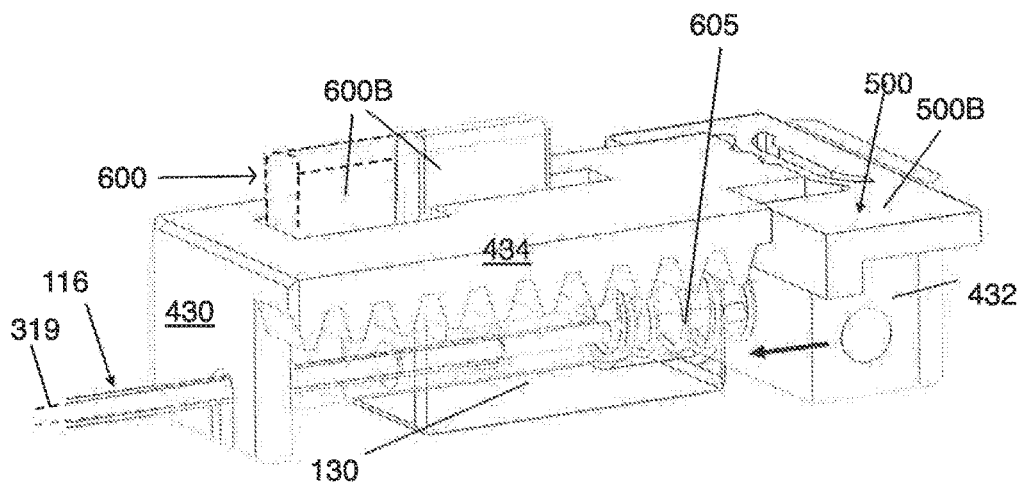

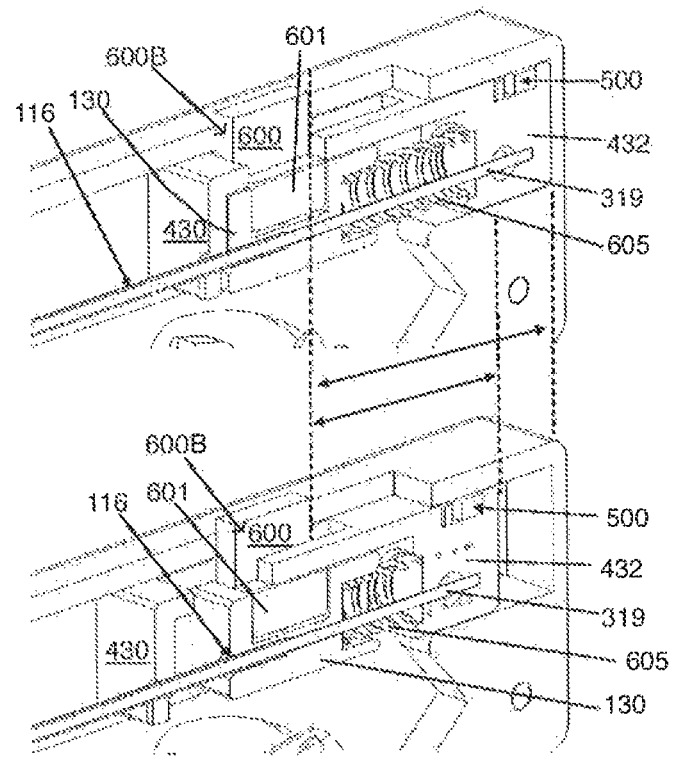
FIG. 4F
FIG. 4G
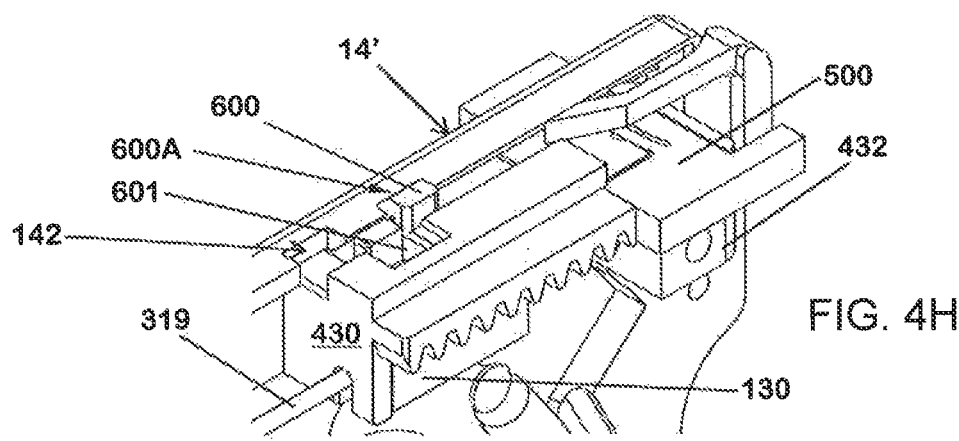
FIG. 4H
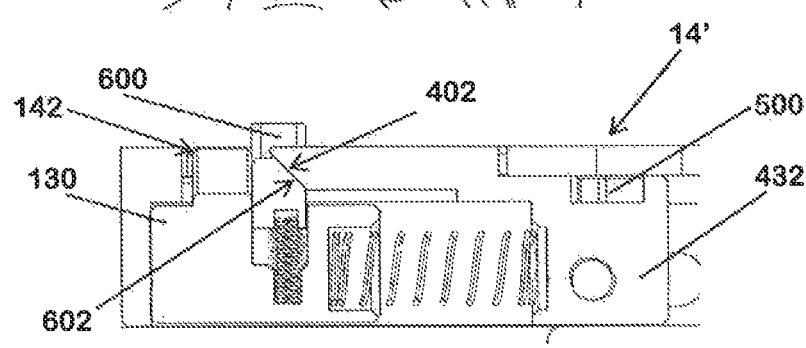
FIG. 4I

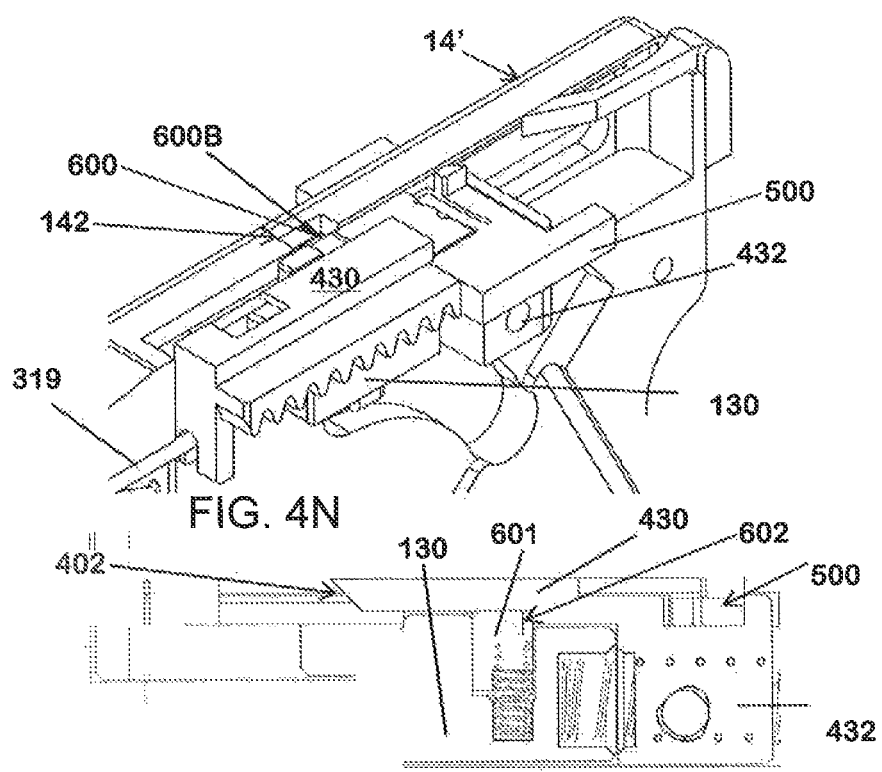

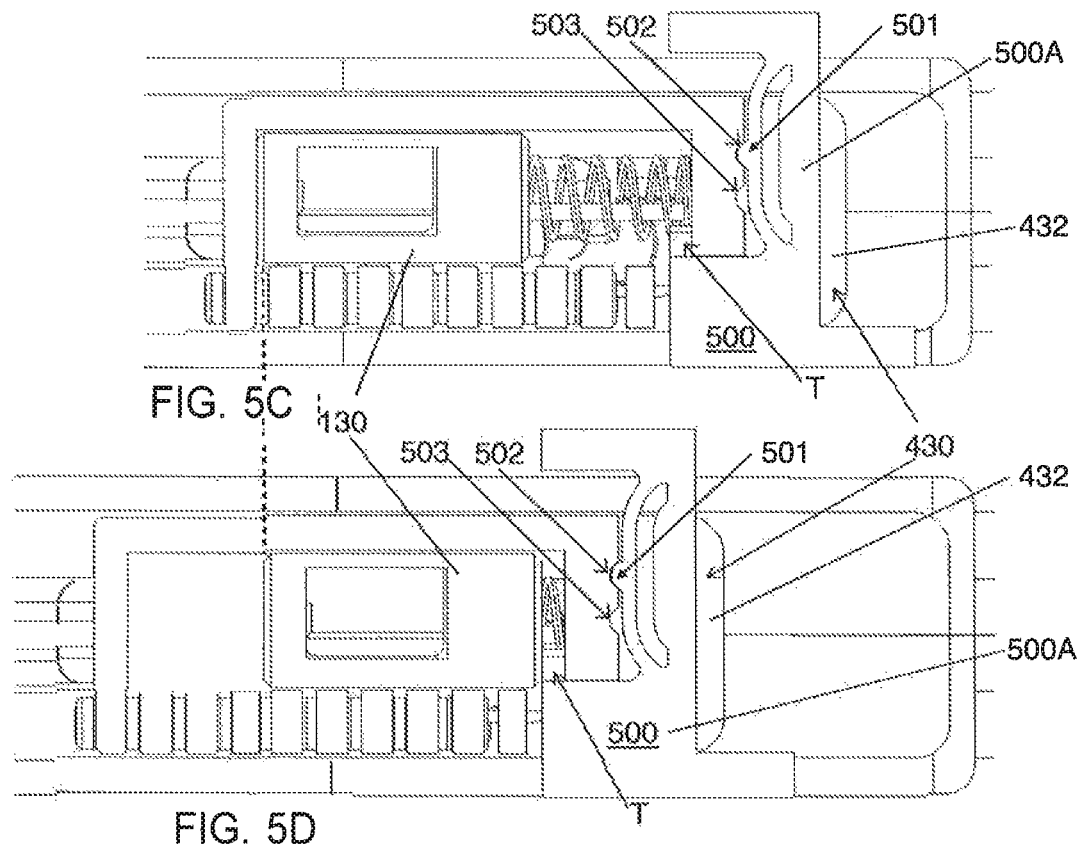
FIG. 5C
FIG. 5D
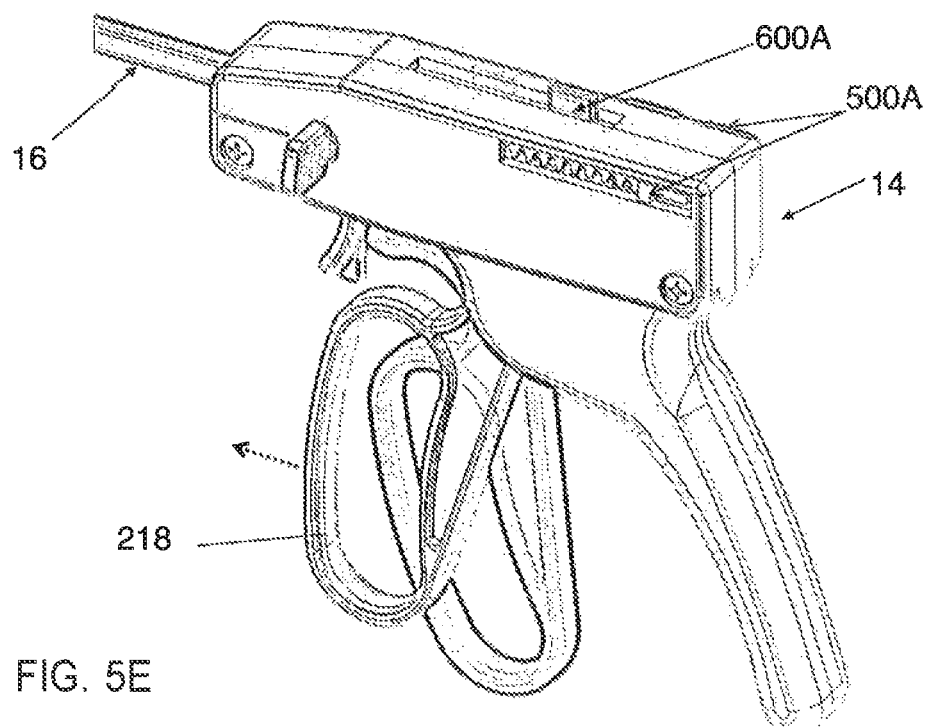
FIG. 5E

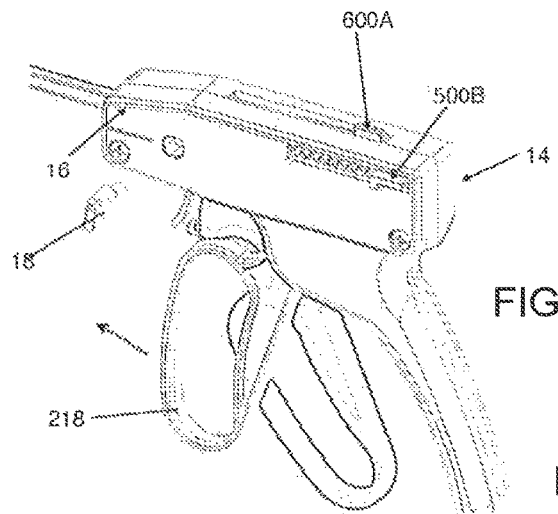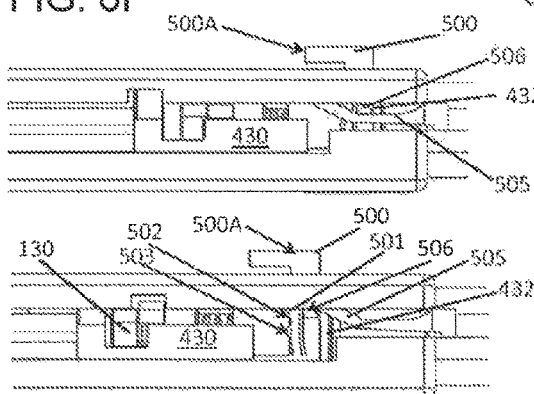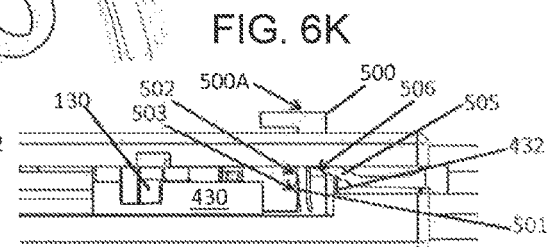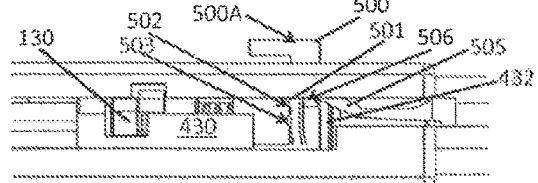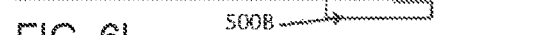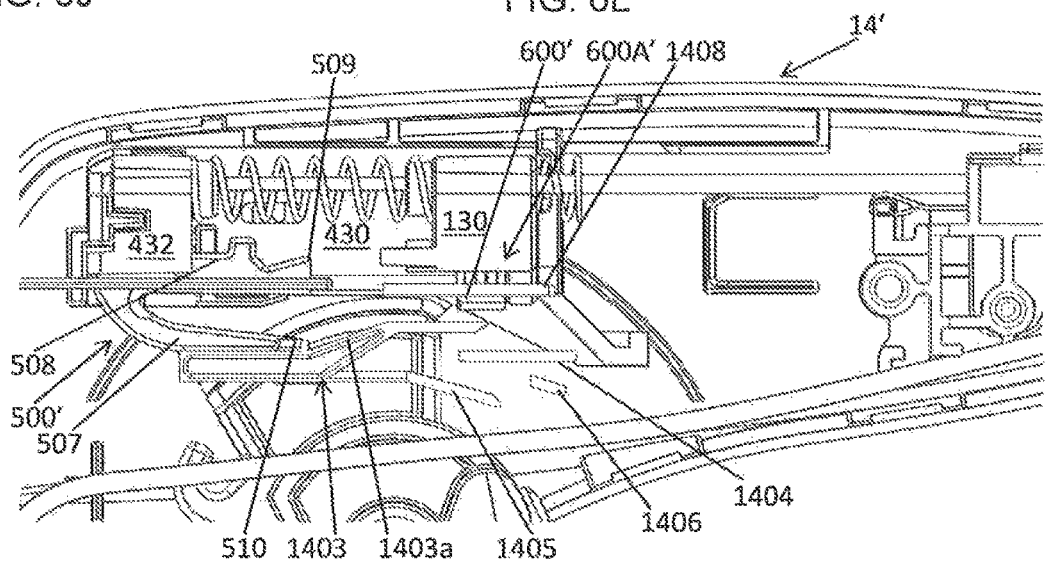

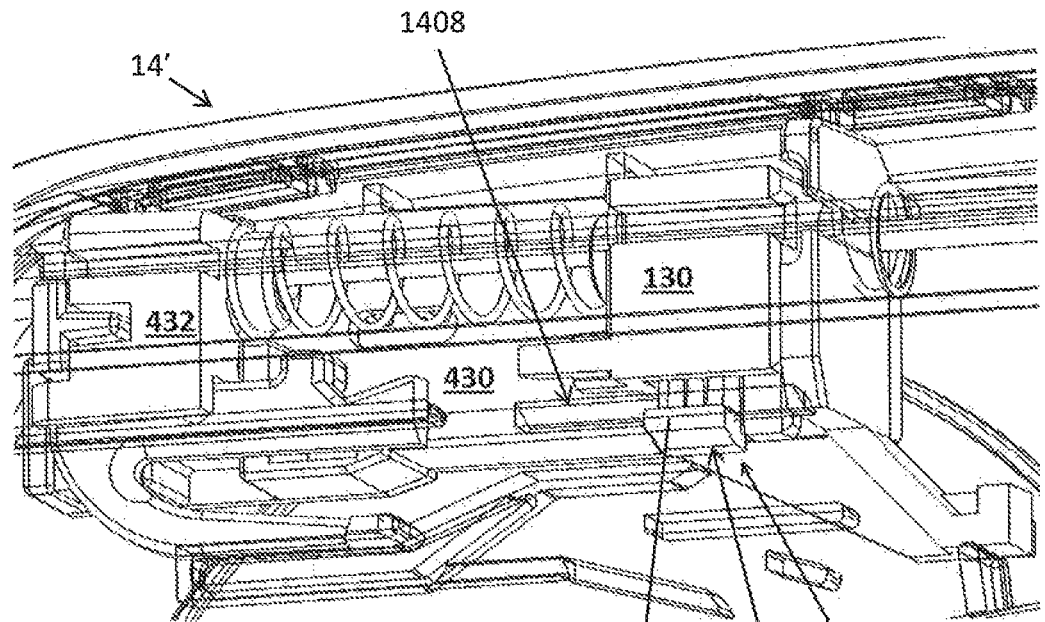
FIG.6M(ii)
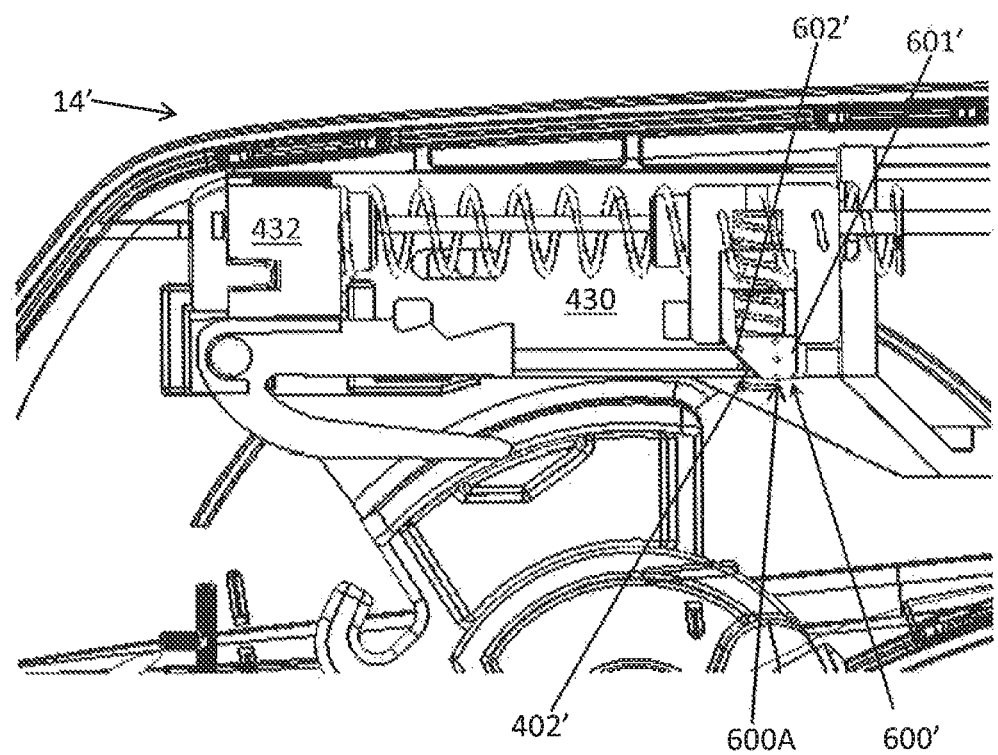
FIG.6M(iii)

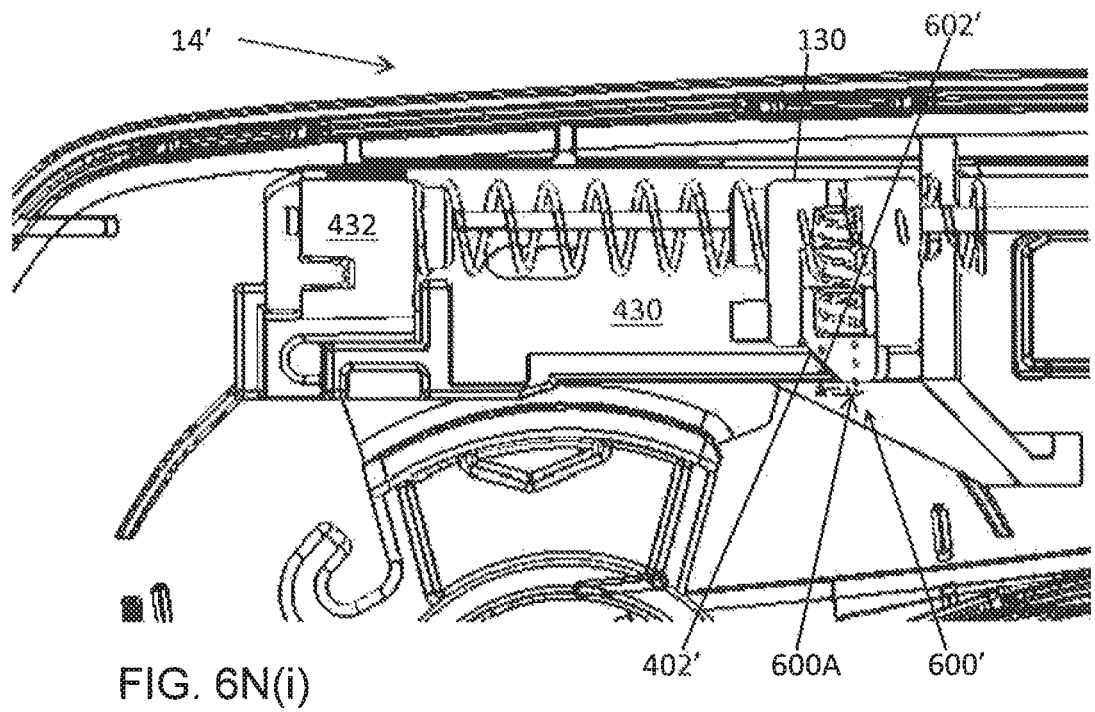
FIG. 6N(i)
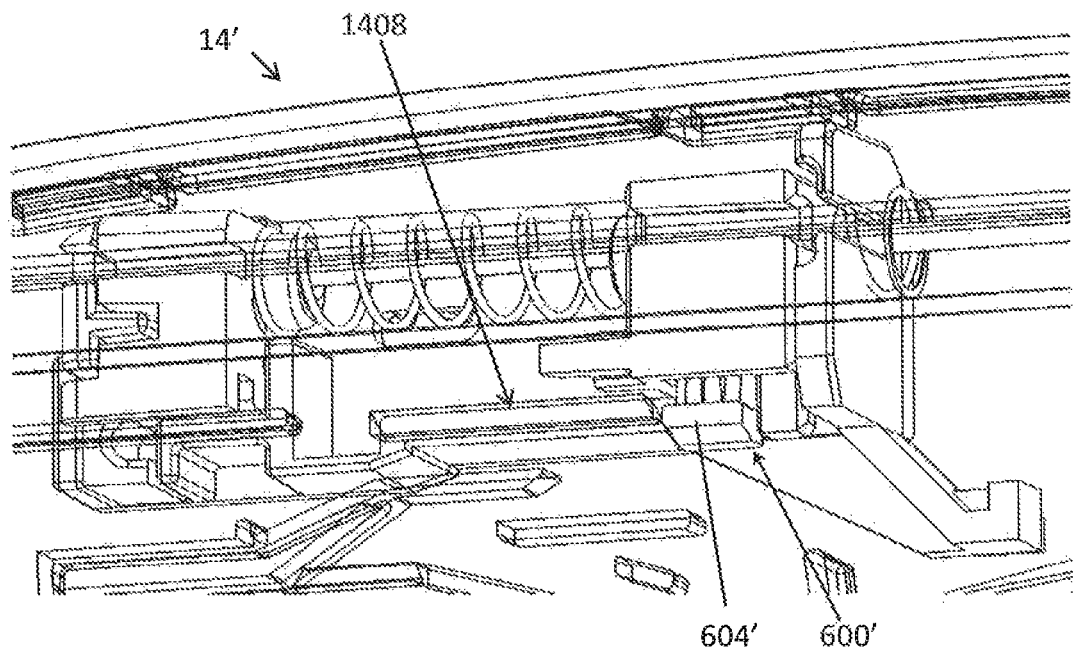
FIG. 6N(ii)

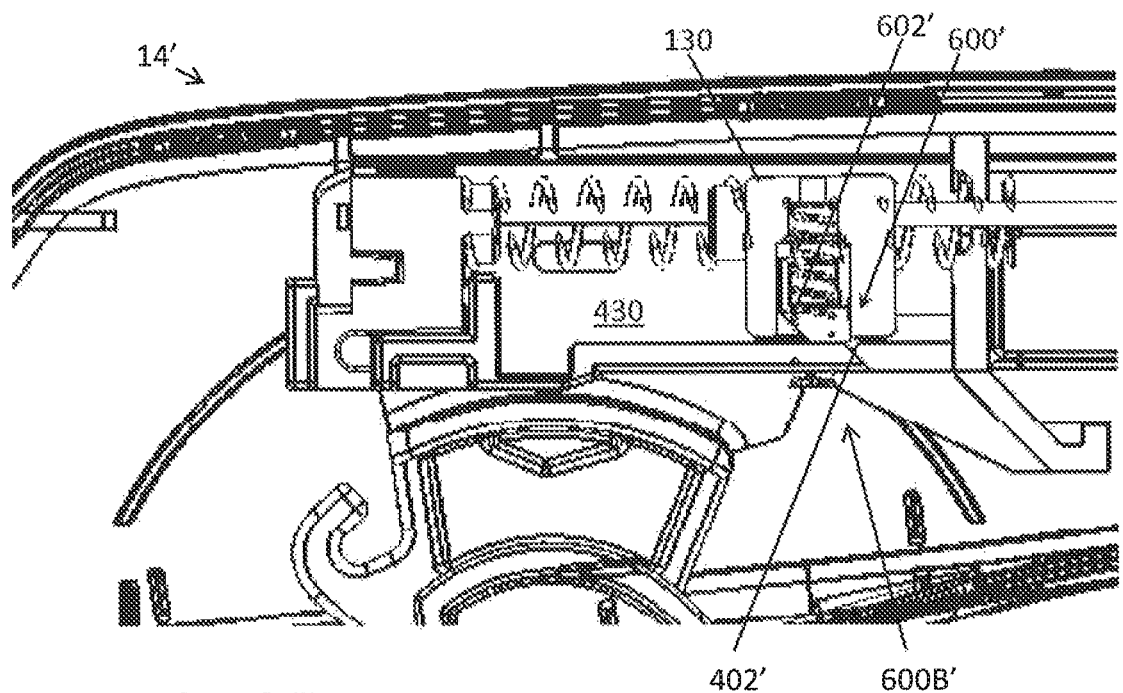
FIG. 6O(i)
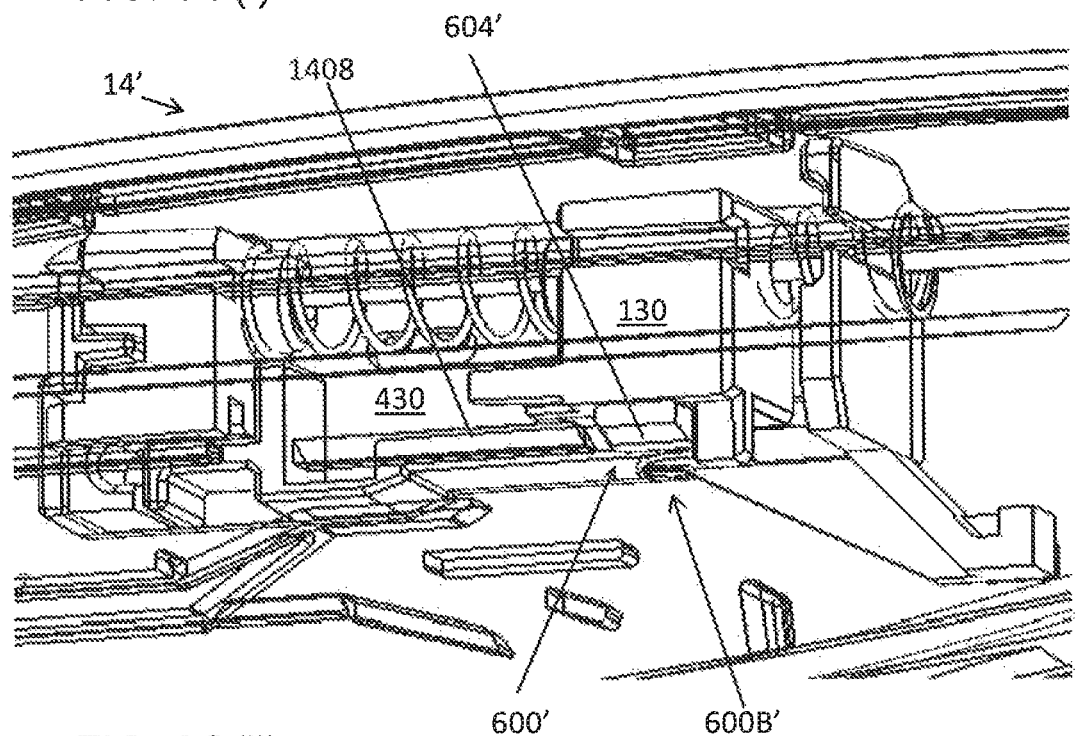
FIG. 6O(ii)

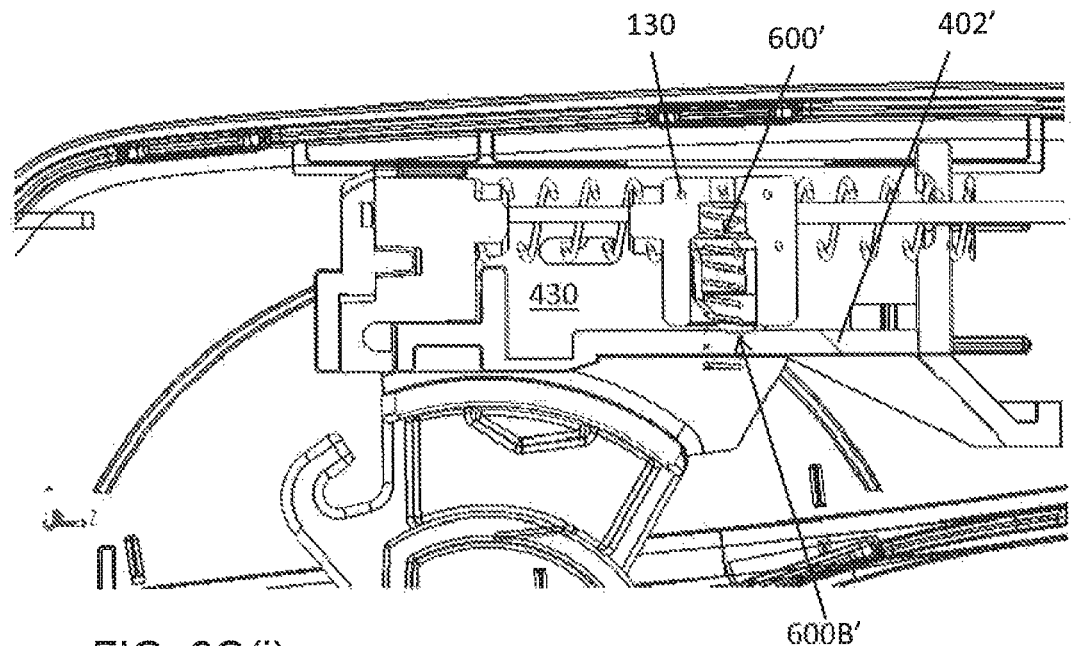
FIG. 6Q(i)
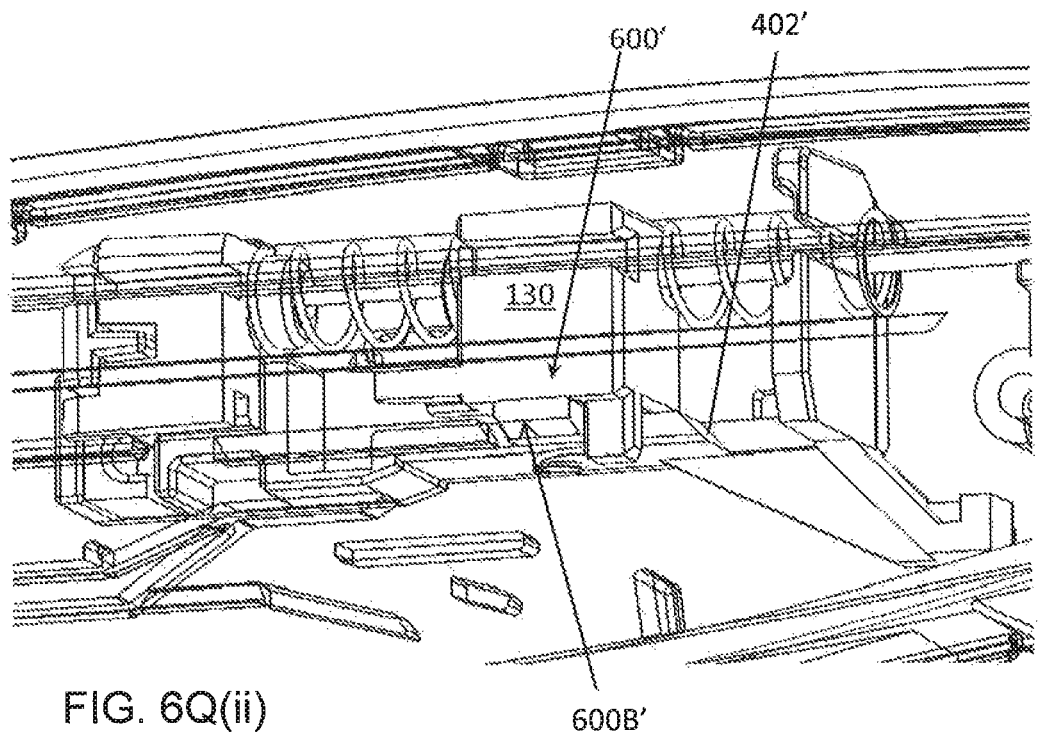
FIG. 6Q(ii)

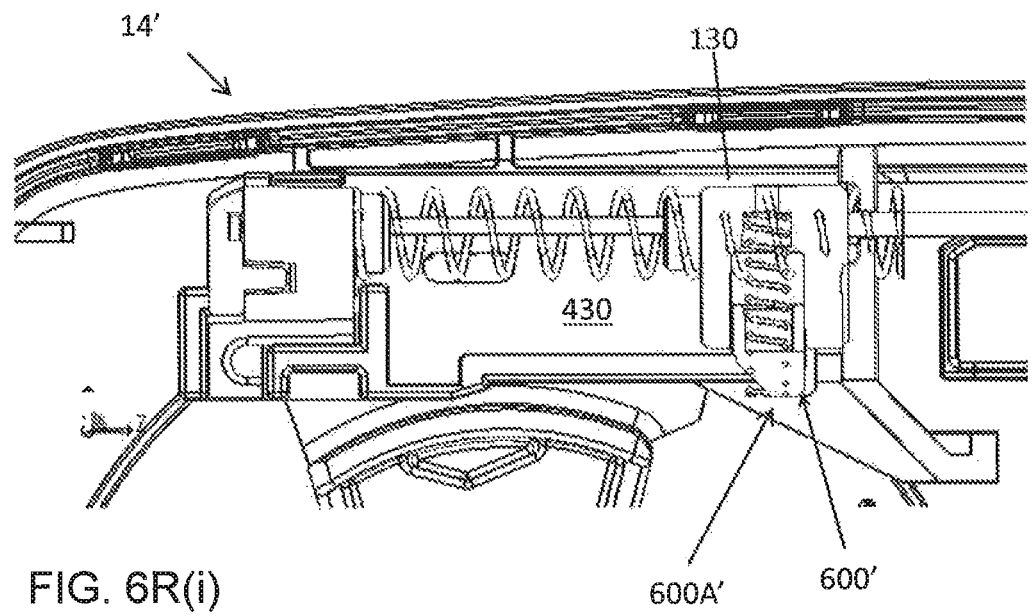
FIG. 6R(i)
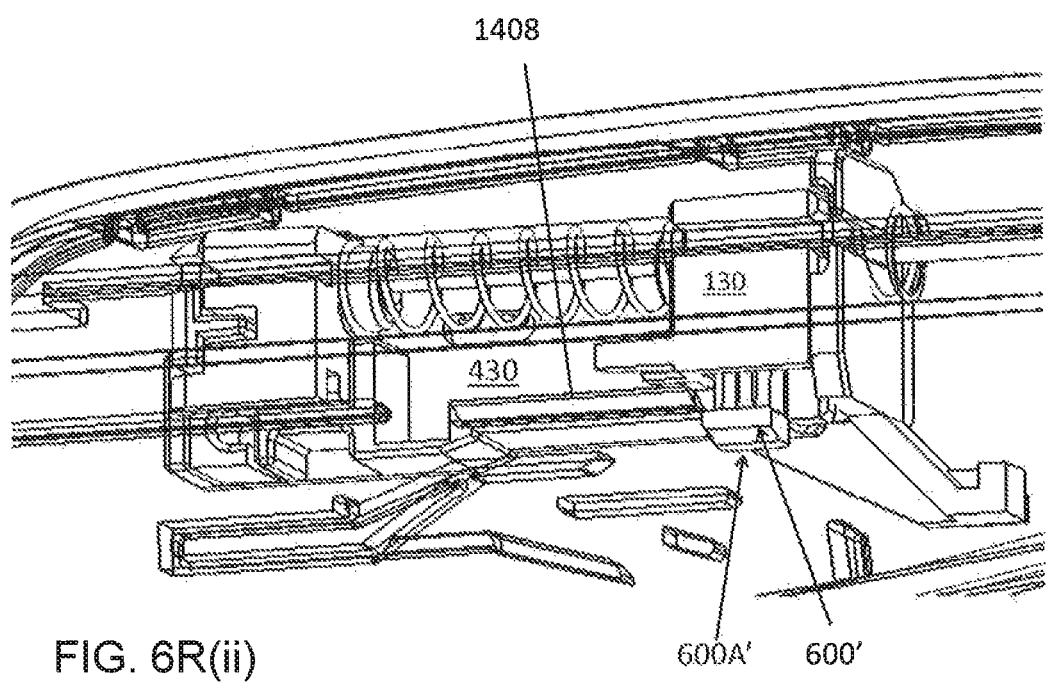
FIG. 6R(ii)

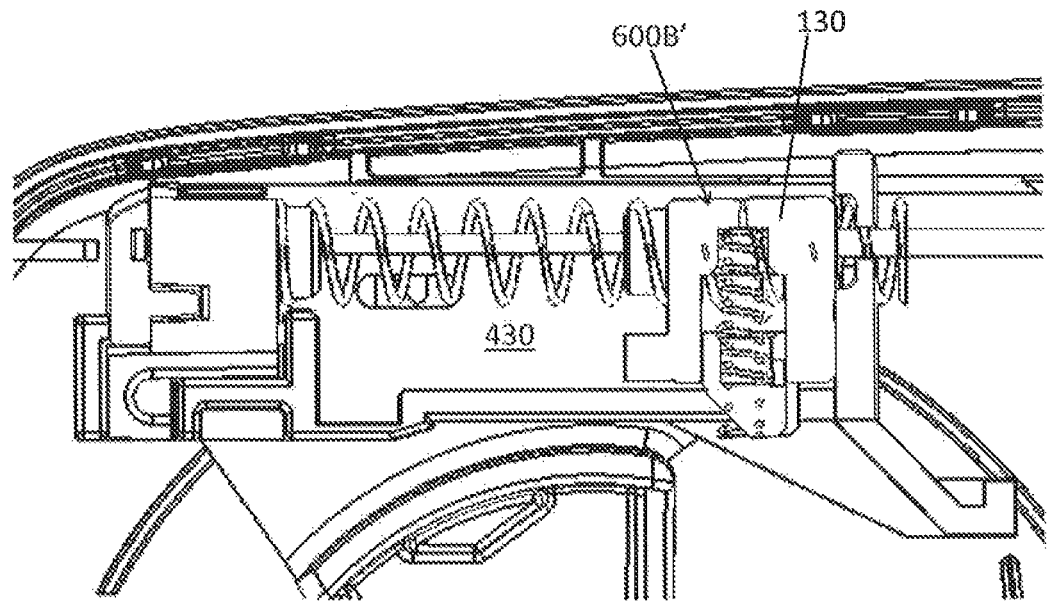
FIG. 6S(i)
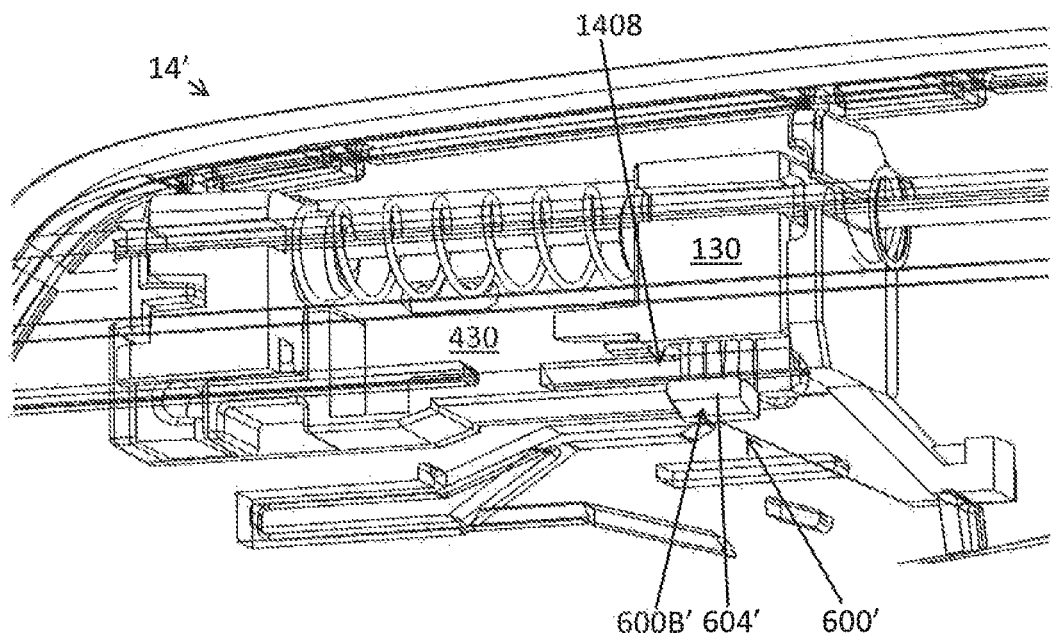
FIG. 6S(ii)

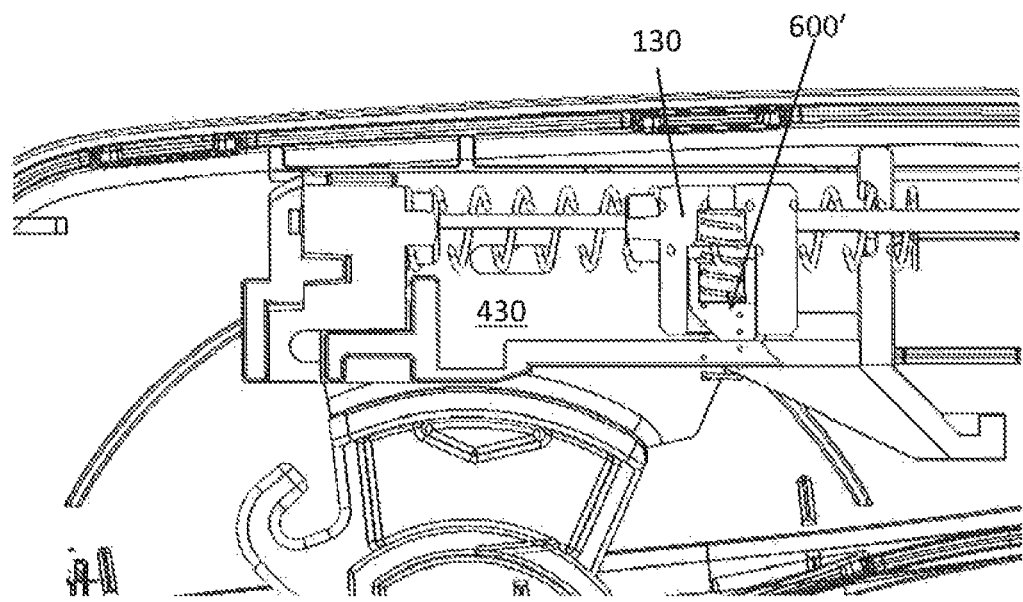
FIG. 6T(i)
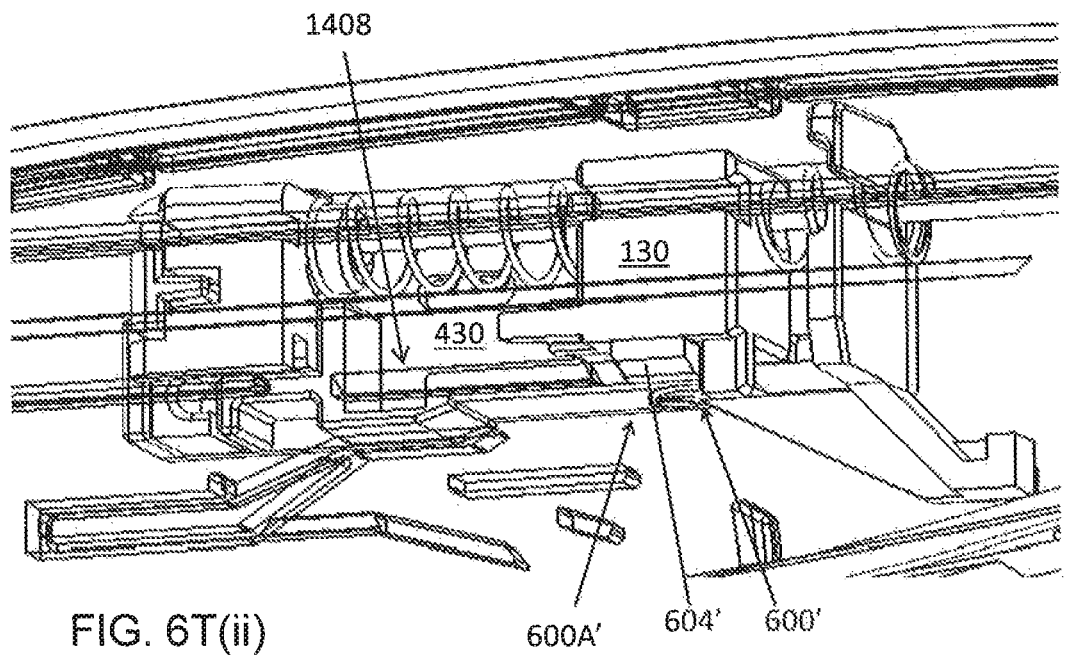
FIG. 6T(ii)

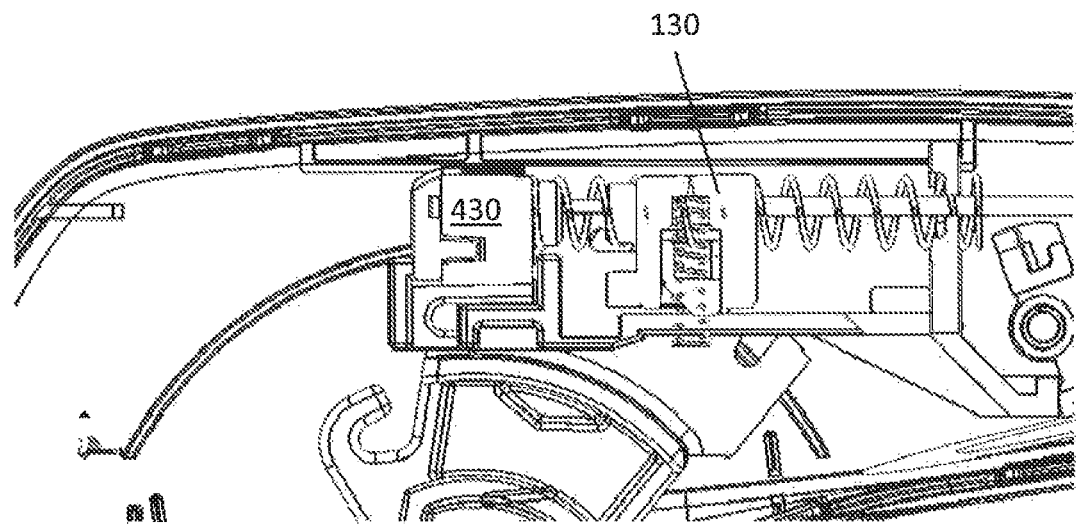
FIG. 6V(i)
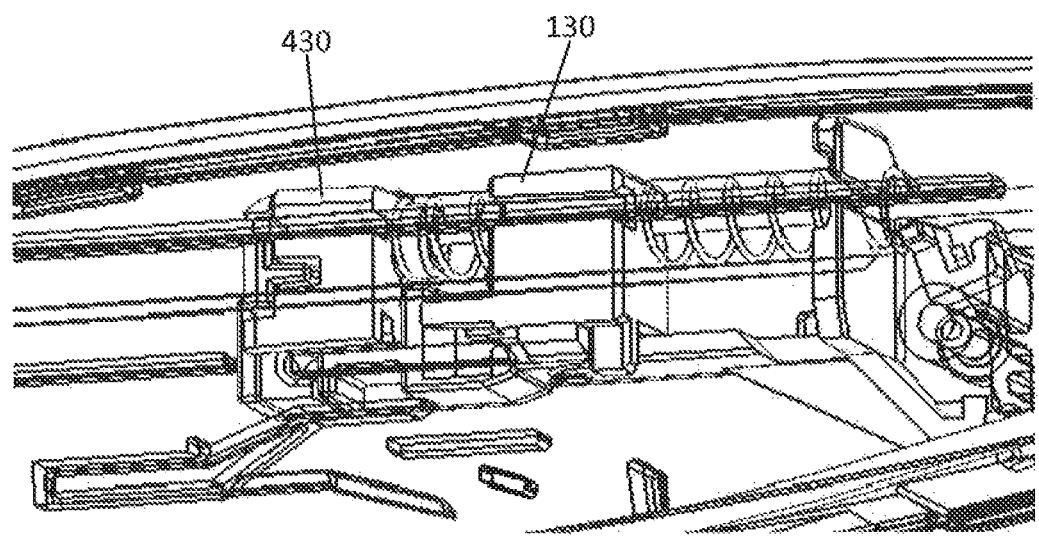
FIG. 6V(ii)

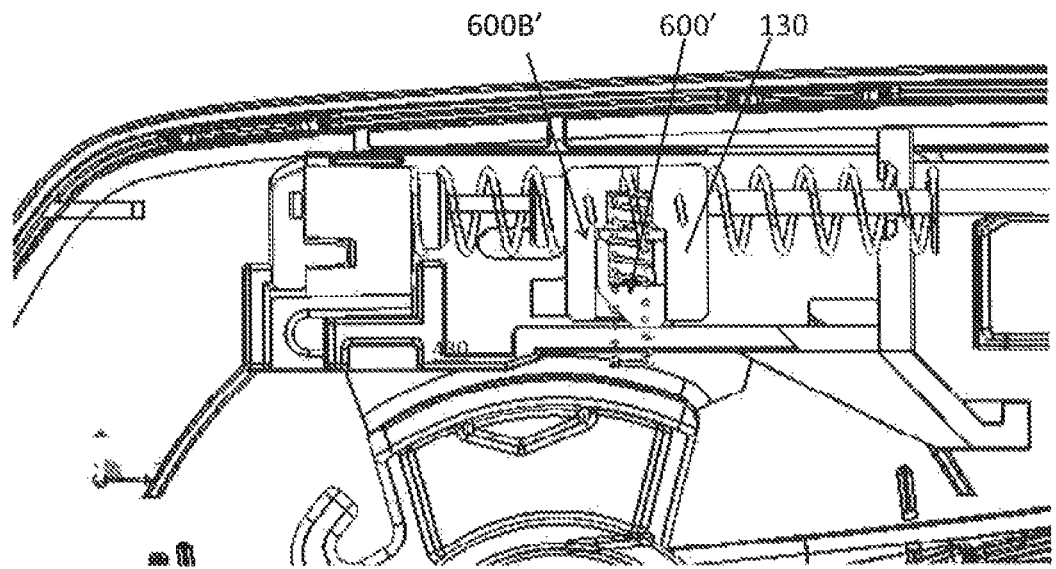
FIG. 6W(i)
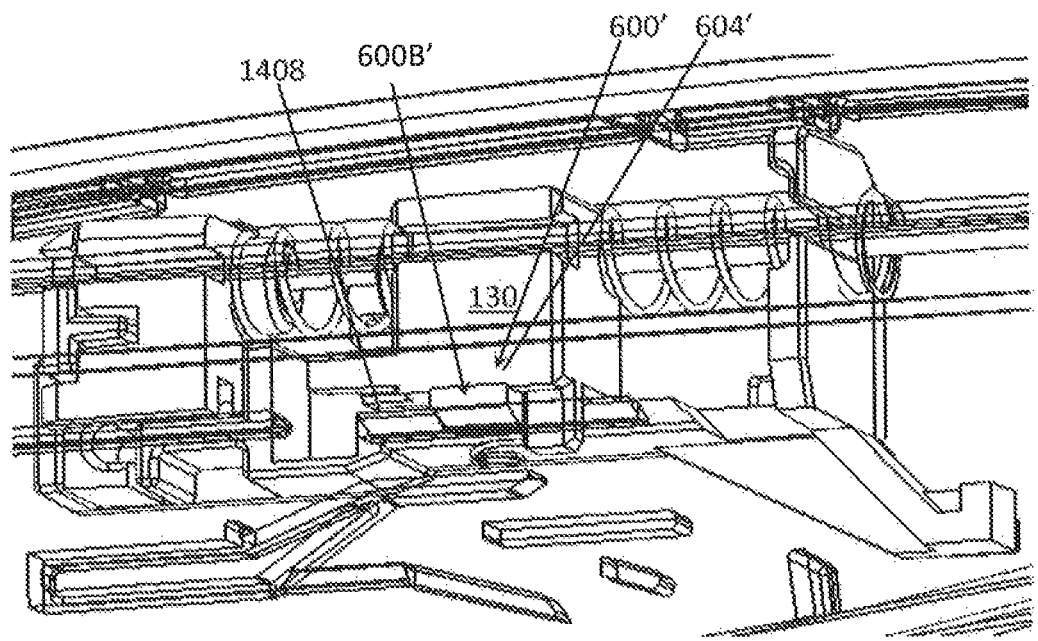
FIG. 6W(ii)

MEDICAL DEVICE HAVING A POSITION INDICATOR

CROSS-REFERENCES TO RELATED APPLICATIONS

This application is a continuation in part of U.S. patent application Ser. No. 11/589,151, now U.S. Pat. No. 9,271,724, which is a non-provisional of U.S. Provisional Patent Application No. 61/524,765, filed on 2011 Aug. 18, and is a non-provisional of U.S. Provisional Patent Application No. 61/524,766, filed on 2011 Aug. 18, and is a non-provisional of U.S. Provisional Patent Application No. 61/561,486, filed on 2011 Nov. 18, and is a non-provisional of U.S. Provisional Patent Application No. 61/582,464, filed on 2012 Jan. 2, and is a non-provisional of U.S. Provisional Patent Application No. 61/586,287, filed on 2012 Jan. 13, and is a non-provisional of U.S. Provisional Patent Application No. 61/593,843, filed on 2012 Feb. 1, and is a non-provisional of U.S. Provisional Patent Application No. 61/597,449, filed on 2012 Feb. 10.

This application is also a continuation in part of U.S. patent application Ser. No. 14/238,945 which is a national phase entry of PCT/IB2012/054204, and which claims benefit from U.S. Provisional Patent Application No. 61/524,765, filed on 2011 Aug. 18, and U.S. Provisional Patent Application No. 61/524,766, filed on 2011 Aug. 18, and U.S. Provisional Patent Application No. 61/561,486, filed on 2011 Nov. 18, and U.S. Provisional Patent Application No. 61/582,464, filed on 2012 Jan. 2, and U.S. Provisional Patent Application No. 61/586,287, filed on 2012 Jan. 13, and U.S. Provisional Patent Application No. 61/593,843, filed on 2012 Feb. 1, and U.S. Provisional Patent Application No. 61/597,449, filed on 2012 Feb. 10.

Each of the aforementioned applications is incorporated herein by reference in its entirety.

TECHNICAL FIELD

The disclosure relates to a medical device, more specifically to a medical device having an indicator for indicating the position of a portion of the device.

SUMMARY

In one broad aspect, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In one broad aspect embodiments of the present invention provide a medical device comprising: a moveable member that is moveable between a first position and a second position for transferring a component; and an indicator mechanism coupled to the moveable member for indicating a position of said moveable member, said indicator mechanism comprising at least two components that are functional to interact with one another to produce an indication; wherein the interaction between the at least two components occurs automatically upon actuation of the moveable member, thereby providing an automatic indication of the movement of the moveable member between the first and second positions.

As a feature of this broad aspect, the indication comprises an audible indication.

As another feature of this broad aspect, one of the at least two components of the indicator mechanism is coupled to the moveable member. In one such example, one of the at least two components is indirectly coupled to the moveable member.

In some embodiments, one of the at least two components is moveable within the housing upon actuation of the moveable member. In some such embodiments, the device comprises a housing, wherein another of the at least two components comprises a feature of the housing.

As another feature of this broad aspect, one of the at least two components comprises a biased component and the other of the at least two components comprises a non-biased component. As an example of this feature, the biased component comprises a deflectable member and the non-biased component comprises a rigid member.

In one particular embodiment, the deflectable member comprises a deflectable arm that is a part of a depth selector. In one such embodiment, the rigid member comprises a feature that is integral with the housing.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

In one broad aspect, embodiments of the present invention include a medical device comprising: an actuator coupled, directly or indirectly, to a moveable member and being for actuating said movable member from a first position to a second position; and an indicator for indicating a position of said moveable member, said indicator being actuated by movement of said moveable member.

As a feature of this broad aspect, the indicator is configured to automatically transition between a first state and a second state upon a predetermined actuation of the actuator which moves said movable member from said first position to said second position.

The actuator, such as a trigger, may be coupled to the indicator directly or indirectly, for example via one or more additional components.

In some embodiments, the device further comprises a component for detachably coupling to the moveable member, wherein movement of the moveable member between the first position and the second position upon actuation of the trigger results in translation of the component between the first position and the second position; and wherein the change in the indicator between the first state and the second state indicates the translation of the component to the second position. In some examples, the component comprises a suture-carrying shuttle or suture trap, a suture or an anchor. In some examples, wherein the moveable member comprises an elongate member, the moveable member may be a needle or a stylet.

In some embodiments, the elongate member automatically returns to the first position after advancement to the second position upon release of the trigger. In one example, the indicator changes between the first state and the second state upon release of the trigger.

In some embodiments, the indicator may be a sensory indicator, such as a visual indicator, an audible indicator, or a tactile indicator. In some examples of a visual indicator, the indicator may be a mechanical indicator or an electronic indicator. In an example of a mechanical indicator, the indicator defines a proximal position wherein said indicator is in the first state and a distal position wherein said indicator is in the second state. In one example of an electronic indicator, the indicator comprises a light-emitting diode (LED). In an example of a tactile indicator, the indicator comprises a protrusion or projection, for example on a surface of the medical device, wherein the protrusion or projection may be retracted or otherwise repositioned upon transition from the first state to the second state.

In a further broad aspect, embodiments of the present invention include a medical device comprising: a needle; a trigger coupled to the needle for reciprocally translating the needle between a first position and a second predetermined position; and an indicator coupled to the trigger, said indicator having a first state and a second state; wherein said indicator automatically transitions between the first state and the second state to indicate advancement of the needle to the second predetermined position from the first position upon actuation of the trigger.

In an additional broad aspect, embodiments of the present invention comprise a medical device comprising: a device proximal portion and a distal tip coupled to the proximal portion; an elongate member housed within the proximal portion; a suture trap for removably coupling to the elongate member; an actuating member for allowing reciprocal movement of the elongate member for translating the trap between a trap proximal position and a trap distal position; and an indicator having a first state and a second state; the actuating member and the elongate member being cooperatively coupled such that actuation of the actuating member advances the elongate member for transferring the trap to the trap distal position, whereby the indicator automatically transitions from the first state to the second state.

In an example of this broad aspect, the first actuation of trigger allows the trap to automatically engage with the device distal tip. In a further example, the second actuation of the trigger allows the trap to automatically disengage with the device distal tip.

In some embodiments, the indicator is housed within the device proximal portion. In one example, the device proximal portion comprises a first aperture and a second aperture and wherein said indicator is visible from a first aperture in said first state and said indicator is visible from a second aperture in said second state.

In one example, the indicator automatically transitions between the first state and the second state upon actuation of the trigger. In a further example, the indicator automatically moves between the first state and the second state upon release of the trigger.

In some embodiments, the indicator serves as an indication of the completion of one or more steps of a multi-step medical procedure.

BRIEF DESCRIPTION OF THE DRAWINGS

In order that the invention may be readily understood, embodiments of the invention are illustrated by way of examples in the accompanying drawings, in which:

FIG. 1E-1K illustrate operation of a device, in accordance with an embodiment of the present invention.

FIGS. 1L, 1M are an illustration of a device for practicing a method in accordance with an embodiment of the present invention;

FIGS. 2A-2F illustrate steps of a method in accordance with an embodiment of the present invention;

FIGS. 3A-3D illustrate further steps of a method in accordance with an embodiment of the present invention;

FIGS. 3E-3H illustrate alternative embodiments of a device and method in accordance with the present invention;

FIGS. 4C-4G illustrate various components of a device in accordance with an embodiment of the present invention;

FIGS. 4H-4O illustrate a device in accordance with an alternate embodiment of the present invention;

FIG. 5A-5E illustrate steps of a method in accordance with an embodiment of the present invention;

FIGS. 6A-6H show a device and method in accordance with an embodiment of the present invention;

FIGS. 6I-6L illustrate a device and method in accordance with an alternative embodiment of the present invention;

FIGS. 6M(i)-6W(ii) illustrate a device and method in accordance with yet another alternative embodiment of the present invention;

DETAILED DESCRIPTION

Figure 1A:
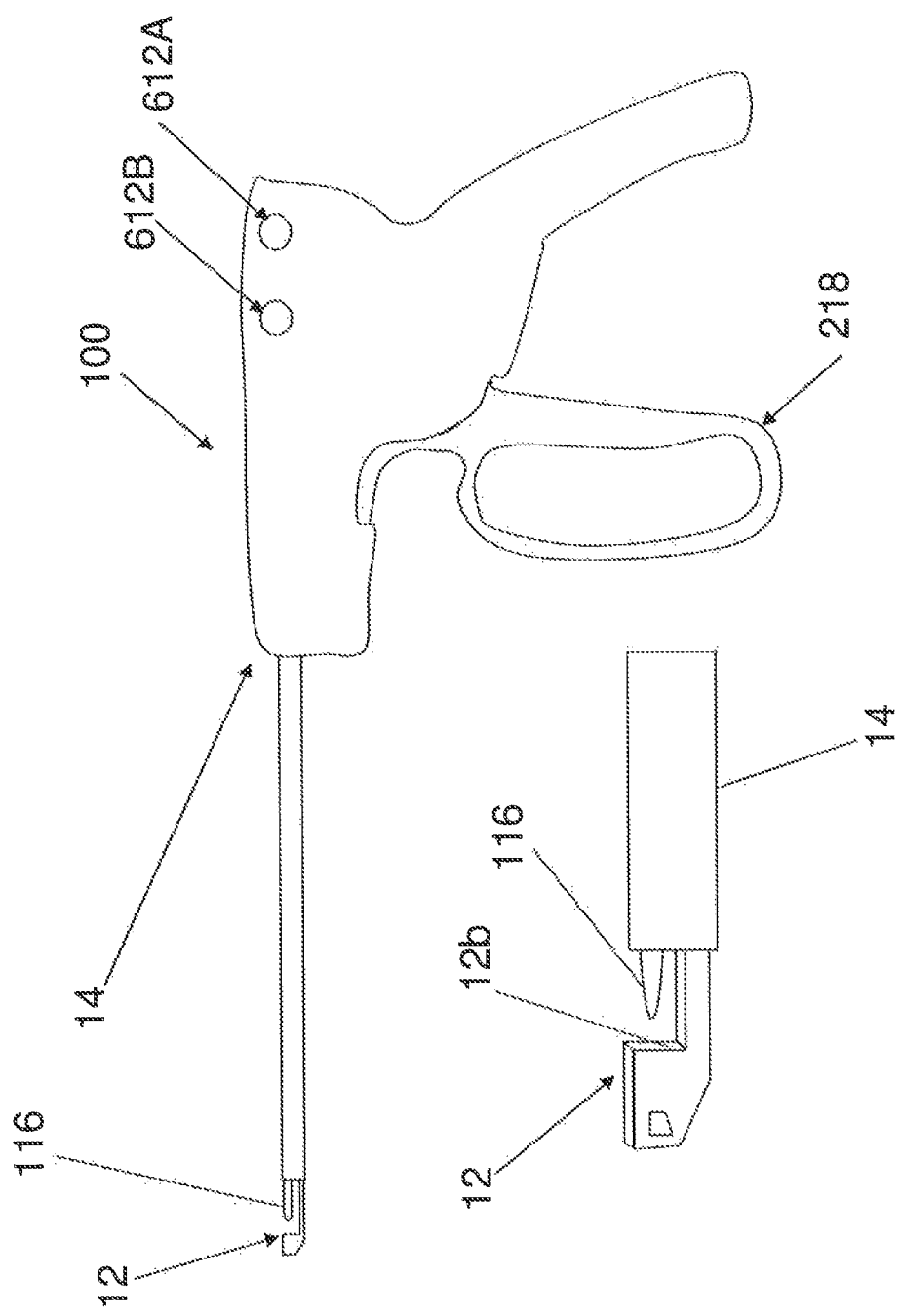
FIG. 1A is a view of portions of a device in accordance with an embodiment of the present invention.

Certain medical procedures require the use of a medical device including a moveable portion or member that is translated or manipulated during the course of the medical procedure. Oftentimes, the position or location of the moveable portion once it has been translated or manipulated is not visible to the practitioner, either directly or via a medical imaging modality. In some specific applications, such as with procedures utilizing suture passing instrumentation to blindly pass a suture or suture retaining component through a tissue and back, it is desirable for a user to be aware of when the moveable portion has reached a position, relative to another portion of the device, for operably engaging with that other portion of the medical device.

For example, medical procedures involving the passage of suture may require capture or retrieval of the suture or a suture carrying component from a side of the tissue opposite a user. In some such cases, it would be beneficial for a user to be made aware when a suture retrieval component has reached a position whereby the capture of the suture (or suture carrying component) may be achieved.

In the past, certain devices have incorporated manual actuators for engaging or coupling components of a medical device, wherein the actuators include indicia indicating that the components have been coupled or decoupled. Such devices require manual assessment by a practitioner that the components of the medical device are in a position to be coupled, after which the actuator is manipulated to couple the components and indicate the coupling.

The present inventors have discovered and reduced to practice several embodiments of means for indicating a position of a portion or component of a medical device during use. Such embodiments are particularly useful and advantageous, for example, when the position or location of the portion or component is hidden from a user's view and/or when the portion or component are not amenable to visualization using an imaging modality (or when such imaging is unavailable to a user). Exemplary embodiments of the present invention provide an automatic mechanism for a medical device that is operable to provide an indication to a user, for example a sensory indication such as an audible or visual indication, when the portion or component of the medical device has, for example, been positioned at a certain location, has been moved or translated by a certain distance or amount or has reached a certain location relative to another component of the medical device.

Embodiments of the present invention avoid manual assessment of whether a moveable portion of the medical device has reached a desired position. The moveable member is coupled to the actuator so that the actuator serves to advance the moveable member from a first position to a second position, whereby, upon the moveable member reaching the second position, the indicator automatically transitions to its second state. In some such embodiments, incomplete actuation of the actuator does not fully advance the moveable member to the second position and does not result in a change of state of the indicator.

In some embodiments of the present invention, an indication mechanism is provided that is coupled to the moveable member whereby actuation of an actuator to move the moveable member from a first position to a second position causes at least two components to interact with one another to produce an indication, whereby the interaction between the two components occurs automatically providing an automatic indication of the movement of the moveable member between the first and second positions. In some such embodiments, the at least two components interact to provide an audible indication. In some such examples, one of the at least two components is coupled to the moveable member. In a specific example of this, the one of the at least two components is indirectly coupled to the moveable member.

In one broad aspect, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Example 1

Embodiments of an indicator mechanism are disclosed that are useful for example with a first embodiment of a device 100. More specifically, embodiments of an indicator mechanism are disclosed that are usable with a device 100 that allows for access to a region of tissue as disclosed herein, such as for example, to puncture tissue and/or to deliver an article within a region of tissue. The device 100 comprises a member which may be moveable between a first position and a second position, for example the member may be moveable between a proximal position and a distal position. In a specific example, the member is moveable from a proximal position to a distal position and is retractable from the distal position to the proximal position. The moveable member may be an elongate member such as a needle 116 that may be housed within a device proximal portion 14. The device 100 may comprise an actuator (such as a trigger 218 shown in shown in FIG. 1A) for advancing the needle 116 with respect to a proximal portion 14 of the device 100. As the trigger 218 is actuated, the needle 116 translates longitudinally from the proximal portion 14 of device 100 towards a distal portion of the device such as a distal tip 12 and it may puncture a region of tissue as it is advanced. In other words the needle 116 is advanced in a direction along the longitudinal axis of device 100. In one example, the needle 116 is a reciprocating needle which is advanced towards the distal tip 12 upon actuation of the trigger 118 and retracted proximally back towards the proximal portion 14 of the device when the trigger is released. In some embodiments, the moveable member is an elongated member that may comprise a stylet and/or needle. In some examples, the moveable member may be configured to be coupled to a component in order to carry the component and deposit it within the tissue. Some examples of components include but are not limited to a suture, a shuttle carrying a suture, a suture trap or an anchor. In some examples, the moveable member may itself comprise a component, i.e. the component may be a portion of the moveable member.

In one embodiment, the device 100 may be used to repair a defect within a region of tissue within a patient's body. For example, as illustrated in FIGS. 1B and 1C, the device 100 may be used to access a defect 300, a puncture may be created in the region of tissue adjacent the defect using the moveable member and delivering an article/component through the puncture in order to repair the defect. The device 100 is inserted at the site of a defect 300, as illustrated in FIGS. 1B and 1C, to allow the moveable member which may be a tissue puncturing member to be passed from the proximal side of the tissue 200 (for example, the external surface of the tissue), to the distal side of the tissue 200 (for example, the internal surface of the tissue). In one example, the tissue puncturing member is a needle/trap assembly 216. In another example, the tissue puncturing member is a needle 116. A tissue supporting member may be positioned through the defect on the distal side of the tissue adjacent the tissue distal surface 204 and may facilitate puncturing of the tissue using the tissue puncturing member. A desired first puncture site P1 is defined at some distance from the defect 300.

In one example of this method, the tissue puncturing member further allows an article/component to be carried from the proximal side of the tissue to the distal side of the tissue, for example, to repair the defect 300. In some embodiments, the tissue puncturing member such as needle 116 itself carries the article/component from the proximal to distal side of the tissue while puncturing the tissue. In other embodiments, the tissue puncturing member creates a puncture to allow access for the delivery of an article/component therethrough. In one example, the tissue puncturing member comprises a needle/trap assembly 216 and the article/component for repairing the defect is a suture 240. In another example, the article/component for repairing the defect is an anchor which may be coupled to or be a part of the moveable member which may be an elongate member such as needle 116. In one specific example of a method of repairing a defect, a needle/trap assembly 216 is used to pass a suture 240. The suture 240 is coupled to the trap 316 of the needle/trap assembly 216. As the needle/trap assembly 216 of device 100 is advanced against the tissue it applies a force against the proximal surface 202 of the tissue in order to puncture the tissue near the defect 300 at the desired puncture site P1.

Figure 1B:
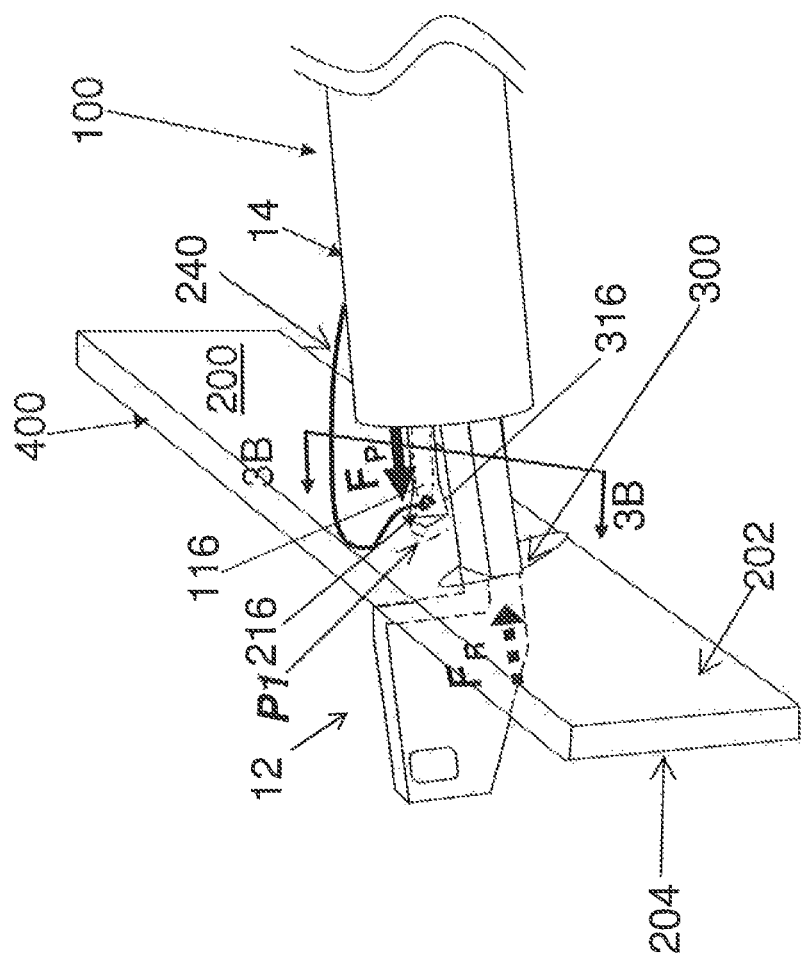
FIG. 1B is an illustration of a method in accordance with an embodiment of the present invention.
Figure 1C:
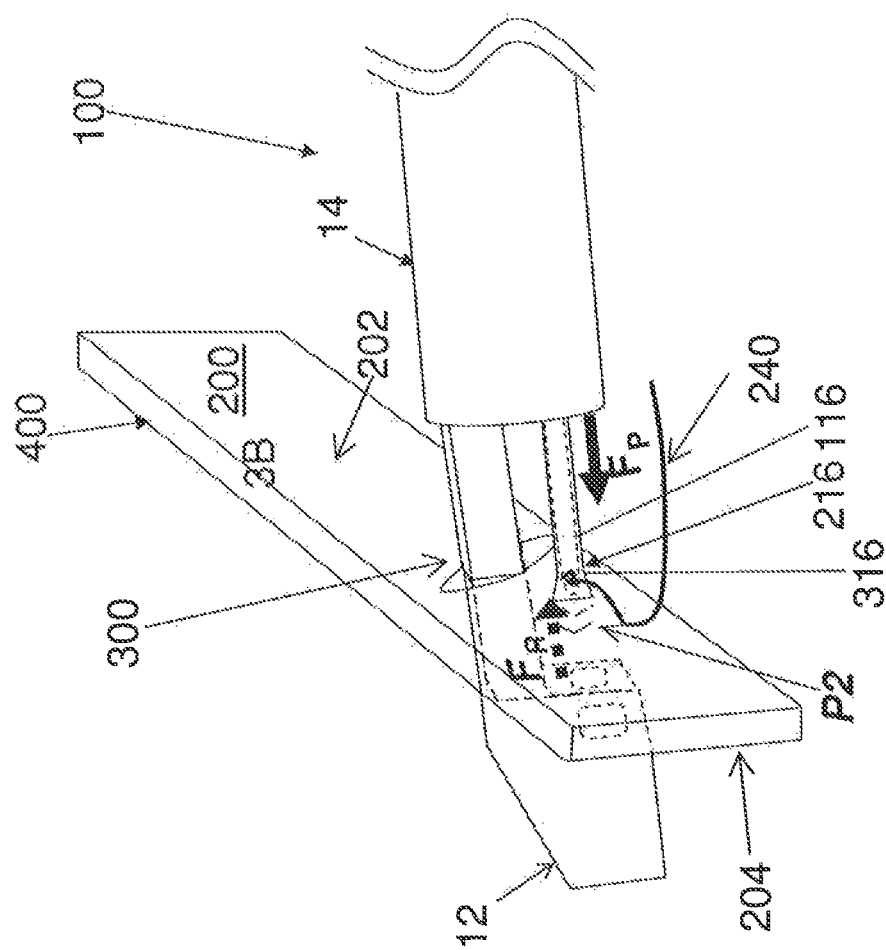
FIG. 1C is an illustration of a method in accordance with an embodiment of the present invention.

As shown in FIG. 1A, a trigger 218 is actuated to advance the tissue puncturing member such as the needle/trap assembly 216 from its first position to a second desired predetermined position such that it pierces the tissue 200. The tissue puncturing member may aid in passing a suture 240 from the proximal side of the tissue 200 to the distal side of the tissue 200. The tissue on one side of the defect may be punctured first as shown by puncture site P1 to pass a suture through the tissue. In one specific example, the distal tip 12 of device 100 defines a receiving chamber. The receiving chamber may be tapered distally to limit the distal movement of the needle/trap assembly 216 within the receiving chamber as the needle/trap assembly 216 is advanced. The trigger 218 is actuated to advance the needle/trap assembly 216 through the tissue 200 at the puncture site P1 such that it translates from the proximal side of the tissue and is received within the needle receiving chamber on the distal side of the tissue. Thus, the trap 316 carrying suture 240 allows the suture 240 to be positioned on the distal side of the tissue. The trap may then engage with the needle receiving chamber. The needle 116 may then be automatically retracted to its first position.

As illustrated in FIG. 1C, the device 100 may then be rotated and the position of the device 100 adjusted to allow suture 240 to be passed through a second segment, portion or flap of tissue on the other side of the tissue. In order to close the defect 300 the suture 240 may be passed through the tissue on the opposing side of the tissue 200 adjacent the puncture site P2. The trigger may be actuated again to allow the needle 116 to be re-advanced from its first position such that it punctures tissue at puncture site P2 on the other side of the defect. Thus needle 116 is advanced until it engages with the trap (with suture 240) which trap is then decoupled from the needle receiving chamber at the device distal tip 12. The needle 116 is then retracted automatically and the trap is retracted along with it. The suture 240 is passed from the distal side to the proximal side of the tissue through the second flap of the tissue. This allows the suture 240 to be passed through tissue on both sides of the defect to allow the two sides of the tissue to be approximated in order to close the defect.

In alternate embodiments, needle 116 may carry suture 240 directly to the other side of the defect, whereby suture 240 may be captured by trap 316 located on the other side of the defect.

In one example, the device 100 may comprise multiple needles 116 and corresponding needle receiving chambers within device distal tip 12. Similarly, the multiple needles 116 may be provided as multiple needle/trap 216 assemblies which may be used to pass a plurality of sutures. In one embodiment, the method of the present invention is used to treat a defect 300 within an annulus fibrosis tissue 400 of the intervertebral disc as shown in FIGS. 1B-1C. During treatment of such a defect within the intervertebral disc, a device 100 is inserted into the defect to allow a suture to be passed from the proximal surface 202 of the annulus tissue 400 to the distal surface 204 of the annulus tissue 400. In one example, a needle 116 and/or needle/trap assembly 216 is used to pass a suture 240. Thus in some embodiments, the suture 240 may be coupled to the needle and/or the needle/trap assembly 216. A suture is passed from the exterior annulus fibrosis to the inner annulus fibrosis and may be used to repair the defect 300 within the annulus tissue 400 using techniques known in the art.

In accordance with an embodiment of the present invention, an indicator may be provided that is associated with the device 100 that allows a user to ascertain if the first step has been successfully completed, i.e. This may allow the user to determine if the needle and/or needle/trap assembly 216 has deposited or transferred a component such as a suture 240 to the desired tissue location such as site P1. Depending on the indication received, the user may decide to proceed with the next step and re-advance the needle to deposit the suture through or at another desired location such as site P2. Conversely, if the first step was not successful, the user may decide to repeat it and may attempt to re-advance the needle 116 and/or needle/trap assembly 216, far enough to deposit the suture in the vicinity of the first desired location such as site P1.

Thus, as described herein above, the needle aids in passing the suture through one side of the defect (P1) and then the other side of the defect (P2) in order allow the two sides to be approximated to close the defect. Thus, an indicator may be used that provides an indication when the needle/suture assembly 216 is advanced far enough through one side of the defect (P1) such that the trap engages with the distal tip 12. The indication may be provided through the indicator moving into its second state from its first state. Thus when the needle automatically retracts to its original position without the trap, the indicator functions to provide an indication that the trap has successfully deposited the suture 240 where it is needed. The user may then proceed with the second step. The trigger 218 may be re-actuated after the device is adjusted to allow the needle to puncture through the tissue 200 on the second side of the defect (site (P2)). The needle is advanced again until it engages with the trap, allowing the trap to disengage from the distal tip. The needle is automatically retracted and the trap is consequently retracted along with the needle. The indicator automatically moves back to its first state from the second state, indicating that the trap has been successfully picked up and the suture has been threaded through tissue 200 on both sides of the defect, allowing the defect to be approximated.

Figure 1D:
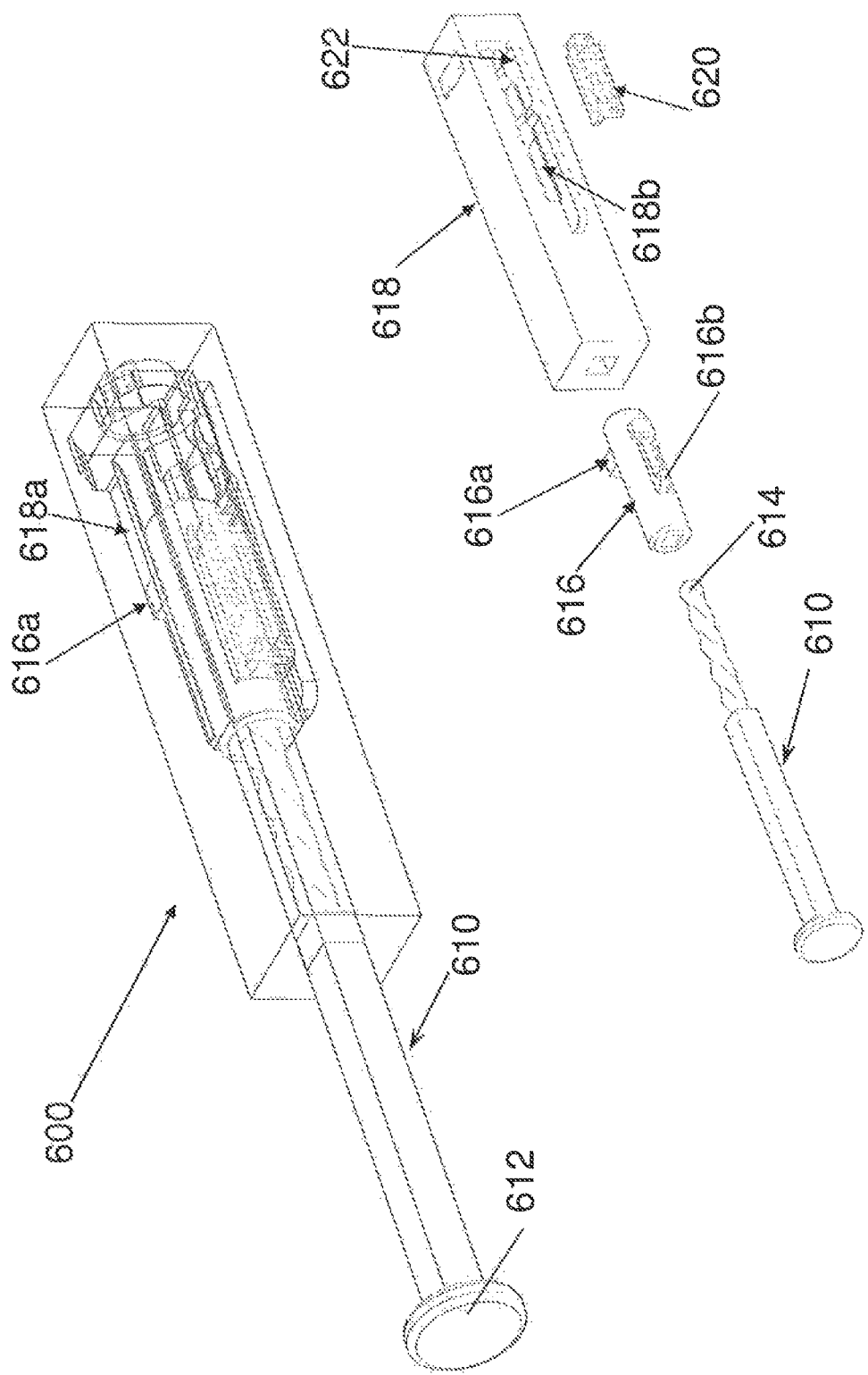
FIG. 1D illustrates a device in accordance with an embodiment of the present invention.

In one embodiment of the present invention, a device 100 is positioned within a region of tissue within the patient's body. The device 100 has a trigger 218 which allows advancement of a needle 116 to allow puncture of the tissue and to allow a suture to be deposited within the tissue, for example using a trap, in order to repair a defect 300 within the tissue. Referring now to FIG. 1D, when the trigger 218 is actuated to advance the needle 116, an indicator 612 may be used to indicate if the trap carrying the suture has been captured at the distal tip 12 of the device 100. This may provide a positive indication of trap capture at distal tip 12 and of the suture being passed successfully through the tissue 200.

In one embodiment, the indicator 612 has two states, a first state when the indicator is in its initial proximal position and a second state when the indicator is in its distal position. In one example, the indicator 612 is coupled to a proximal end of a rod 610 having a helical thread or helix 614 that can co-operatively engage with threads on the inside of a hub 616 of the needle 116 (the needle 116, not shown, extends distally from the needle hub 616). The rod 610 is actuated using a trigger 218. In another example, the indicator 612 is a part of a gear rack which co-operatively engages with a geared portion of the trigger 218. The gear rack is slidable along the housing 618 and is coupled to the rod 610.

When the trigger 218 is actuated, the rod 610 advances and the needle hub 616 translates with it, which in turn advances the needle 116 in order to puncture tissue 200 at site P1. The trap 316 may be then coupled to the distal tip 12. The indicator mechanism is associated with the threading of the helix 614 inside the threaded portion of the hub which shortens the exposed portion of rod 610 (i.e. portion of rod 610 that is exposed outside the hub 616 which effectively shortens the rod 610). Thus, when the trigger 218 is released, the hub 616 with the shortened rod 610 is retracted, which results in the indicator 612 (which may be a part of the gear rack coupled to rod 610) being positioned distal to the initial indicator position, and is now in its second state. Thus, in one example, upon actuation of the trigger and subsequent release of the indicator 612, the indicator 612 changes from its first state to its second state. After the actuation of the trigger, the needle 116 may be retracted to its original position. The trigger 218 is then re-actuated. Once the trigger is pressed the rod 610 travels distally and allows the needle 116 to puncture through tissue at site P2. The needle continues to advance and the needle 116 may then re-couple to the trap 316. When the trigger 218 is released, the helix 614 unthreads and lengthens to its original position, which is the indicator 612 proximal position. Thus, the indicator reverts to its first state. In addition, in some embodiments, when the trigger 218 is released, the needle 116 and trap 316 (coupled to the needle 116) return to their initial proximal positions.

The indicator 612 is indicative of needle advancement and/or retraction as well as the position of the trap 316. When the trigger 218 is first actuated, the threading of the helix 614 inside the hub 616 results in shortening of rod 610 and also results in the coupling of the trap 316 within the device distal tip 12 and the uncoupling of the trap 316 from the needle. Thus when rod 610 is retracted, the indicator 612 in its distal position indicates transfer of the trap 316 from the needle to the distal tip 12 and indicates that the trap 316 position is distal. Similarly, when the trigger is re-actuated the unthreading of the helix 614 as the trigger is released results in lengthening of rod 610 and results in decoupling of the trap 316 from the device distal tip 12 and re-coupling of the trap 316 to the needle 116. Thus, when rod 610 is retracted, the indicator 612 in its proximal position indicates transfer of the trap 316 from the distal tip 12 to the needle 116 and indicates that the trap 316 position is proximal.

Alternatively, the trap 316 may be initially positioned at the device distal tip 12 in the trap distal position. In such an embodiment, a first actuation of the trigger 218 allows advancement of the needle 116 to capture or retrieve the trap 316 from the trap distal position to transfer the trap 316 to the trap proximal position and concurrently allows the indicator 612 to automatically move or change from the first state to the second state to indicate that the trap 316 is now in its proximal position. In other words, the first actuation of trigger 218 allows the trap 316 to automatically disengage with the device distal tip 12 and coupled with the needle 116. The trap 316 may then retract with the needle 116 as the trigger 218 is released. A second actuation of the trigger 218 allows advancement of the needle 116 to return the trap 316 into the trap distal position, i.e. the second actuation of the trigger allows the trap 316 to automatically engage with the device distal tip 12. Concurrently, the second trigger actuation allows the indicator 612 to automatically revert from the second state to the first state to indicate that the trap 316 is in its distal position.

In one specific example of this embodiment described above, the indicator 612 is coupled to the trigger 218 via rod 610. The rod 610 is receivable within a needle hub 616. The rod 610 has a helical thread 614 along a portion thereof, which co-operatively engages with a corresponding thread within the needle hub 616. In the initial starting position the indicator 612 (which may be a part of the gear rack coupled to the rod 610) may be visible through a first aperture 612A within the device proximal portion 14, which defines the indicator 612 in its first state. Thus, when the trigger 218 is actuated, the rod 610 is advanced which in turn advances the needle hub 616 causing the needle 116 to advance in order to puncture the tissue 200. The needle hub 616 resides within a housing 618 which is fixed within the proximal portion 14 of the device.

Figure 4A:
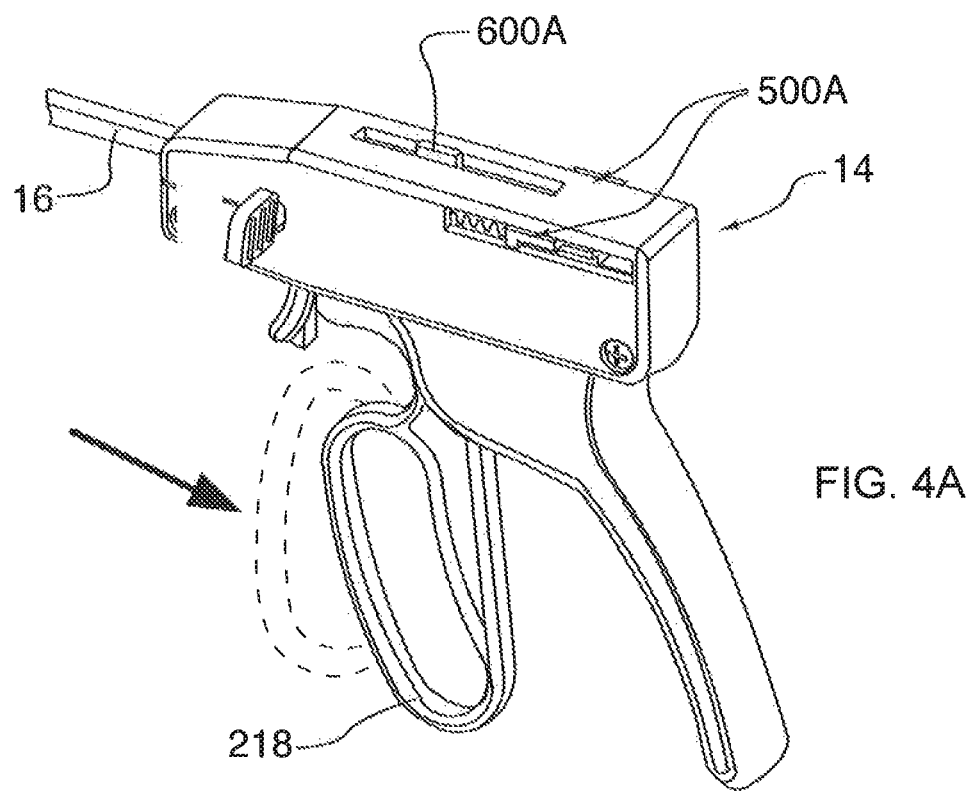
FIGS. 4A-4B illustrate steps of a method in accordance with an embodiment of the present invention.

As shown in FIG. 1A and FIG. 4a, the indicator 612 is initially in its proximal position 612A, when the trigger 218 is not depressed. The helical thread 614 is in its fully retracted position. The device 100 provides a mechanism that enables the needle hub 616 to translate within the housing 618 which allows advancement of the needle 116 from the initial or first needle position. In one specific example, as mentioned above, the trigger 218 has a geared portion that co-operatively engages with the gear rack (not shown) that is slidable along the housing 618 and is coupled to the rod 610. The trigger 218 is coupled to a biasing mechanism such as a spring biased mechanism. When the trigger 218 is in a neutral position, the spring is held against the bias. As the trigger is actuated, the geared portion of the trigger 218 advances the gear rack which further exerts a force against the spring bias. The rod 610 coupled to the gear rack translates distally causing the needle hub 616 and consequently the needle 116 to translate distally with respect to the housing 618. The hub 616 comprises a needle hub tab 616a that rides in a slot 618a within the housing 618. Due to the engagement of the needle hub tab 616a within the housing slot 618a, only translation of the hub 616 is permitted as shown in FIG. 4a. Since the hub 616 cannot rotate, the helical thread 614 of rod 610 pushes the hub 616 as the rod 610 is advanced. (Additionally, a snap tab 616b on the hub pushes a lifter 620 forwards, the lifter 620 allows the hub to retract back when the trigger 218 is released). In one example, the needle 116 punctures through site P1 as the hub is advanced.

Once the hub 616 has translated maximally within the housing 618, the needle 116 is in the second needle position which is the desired predetermined position of the needle 116. The helical thread 614 threads into the corresponding thread of the hub 616. This causes the hub to rotate, allowing the hub 616 to screw onto or thread onto the rod 610, which shortens the length of the rod 610 that is outside the hub 616 as shown in FIGS. 1F and 1G. The hub tab 616a rotates within rotational slot 618c within the housing. When the trigger 218 is released, the biasing mechanism, such as the spring biased mechanism automatically urges the gear rack and thus rod 610 proximally towards the bias back towards the needle first position. The rotation of the rod 610 is restricted again using housing slot 618b. Thus as the trigger is released, the helical thread 614 of the rod 610 retracts, and since the hub 616 cannot rotate, the helical thread 614 pulls the hub proximally. Thus, the hub tab 616a rides within slot 618b which prevents the helical thread 614 from unthreading from the hub 616, and when the rod 610 is retracted, only a short length is exposed outside the hub 616 (as shown in FIG. 1H) and the indicator 612 (which may be a part of the gear rack coupled to rod 610) is now in its second state and is visible through the second aperture 612B. (The position of the indicator 612 as shown in FIG. 1G upon full actuation of the trigger 218 is distal of the position of the indicator in FIG. 1H, which shows the indicator in its second state). In one specific example, a trap 316 that is carried by the needle 116, is deposited at the distal tip 12 as the hub 616 and needle 116 rotate during needle advancement. Thus, the trap 316 is coupled to the distal tip 12 through a rotational mechanism. In summary, as the needle 116 advances with the trap 316 (which carries the suture) it punctures through the tissue 200 at site P1. Once the hub 616 advances, the needle 116 punctures through a tissue flap on a first side of the defect 300 as shown in FIGS. 1B and is then coupled to the distal tip 12.

The hub 616 automatically retracts when the trigger is released and the indicator 612 automatically moves to its second or distal state (i.e. indicator 612 is visible through the second aperture 612B). This may be indicative of the trap 316 being received at the distal tip 12 and/or successful placement of suture through the tissue at site P1. In other words, the indicator 612 indicates to the physician that the needle 116 has been advanced far enough to a predetermined desired location to allow the trap 316 to be captured by/or engaged with the distal tip 12. In some embodiments, the indicator 612 may additionally indicate that the needle 116 has additionally been rotated fully after advancement to the predetermined desired location to allow the trap 316 to captured by/or engaged with the distal tip 12. Thus the physician has a positive indication that the suture was successfully deposited through the tissue flap along a first side of the defect 300 at site P1.

As described in the embodiment above, the retraction of hub 616 allows the indicator to move into its distal or second position. In one specific example, there is a snap arm 622 (shown in FIG. 1D) on the housing 618 that prevents proximal retraction of the hub 616 when the trigger is released. Thus, in order to enable the hub 616 to retract back as the trigger is released, a lifter 620 is engaged with the hub to the hub snap tab 616b when the rod 610 is advanced, as shown in FIGS. 1E and 1F. When the trigger 218 is fully actuated, the lifter 620 translates with hub 616 to its distal most position pushing the snap arm 622 out of the way of the hub 616. This allows the hub 616 to translate back as the trigger 218 is released. The indicator 612 which is coupled to the hub 616 via rod 610 moves to its distal position indicative of suture being passed successfully through site P1 and trap being captured at the distal tip 12.

The physician then may reposition the device in order to allow the suture to pass through tissue 200 through site P2 on the other side of the defect 300. In one specific example, the device 100 may be rotated by 180° and the trigger may be re-actuated. When the trigger 218 is re-actuated the geared portion on the trigger 218 pushes the gear rack distally. Thus, as, shown in FIG. 1I, re-actuation of the trigger 218 allows the needle to advance, allowing the indicator 612 to advance from the indicator distal position. The rod 610 remains in its threaded position inside the hub 616 (i.e. with only a short/small segment of rod 610 being exposed outside the hub 616). When the hub 616 is advanced, the movement of the hub 616 is restricted to translational motion only as needle hub tab 616a translates along slot 618b. This allows the threaded helical thread 614 of the needle 116 to push the needle hub 616 distally allowing the needle to puncture through tissue along a second side of the defect at site P2. The needle 116 is received within the trap 316 that is engaged at the distal tip 12. Once the needle hub tab 616b has reached the end of the translation slot 618b, it then moves into the rotation slot 618c and rotation is then permitted. However, proximal translation of the needle hub 616 is prevented by the snap arm 622 on the housing snapping behind and abutting against the hub 616. In some embodiments, the lifter 620 remains in the distal position after having detached from the hub 616 during initial actuation of the trigger.

Figure 1K:
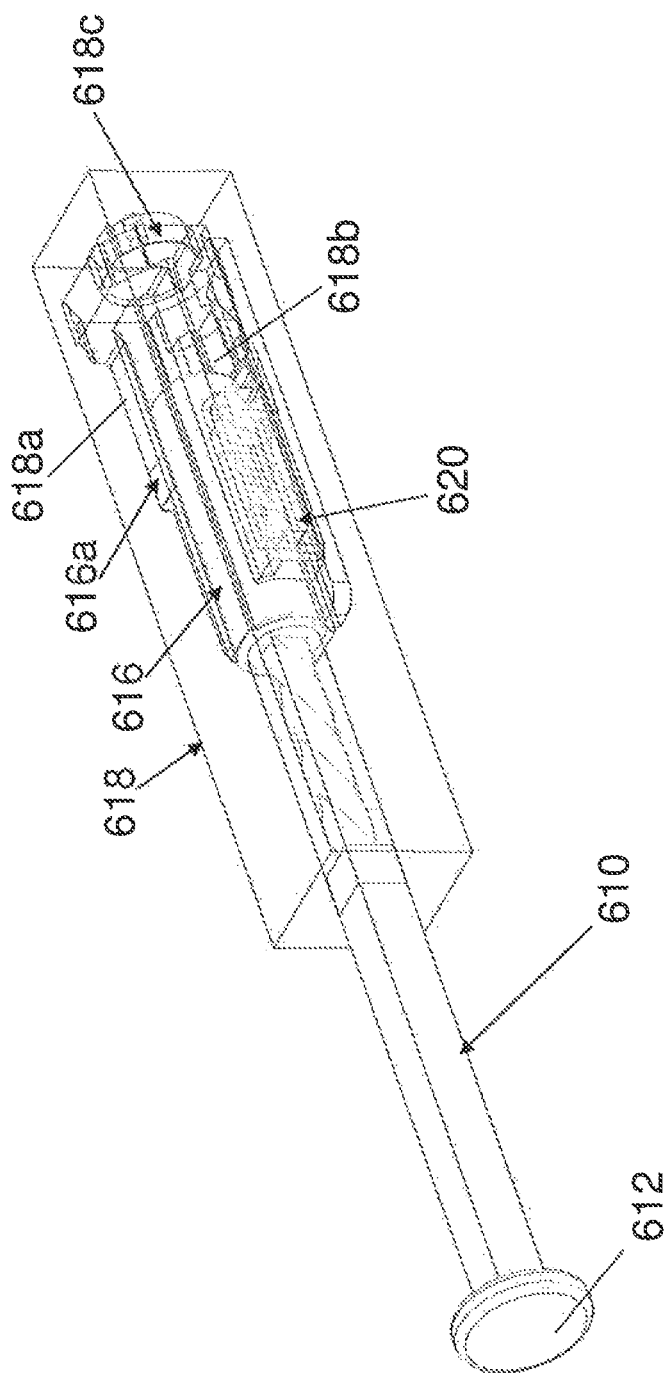

As the trigger 218 is released, the spring biased mechanism allows the trigger 218 to automatically retract proximally towards the bias. The geared portion of the trigger 318 causes the geared rack to translate proximally. The hub 616 unthreads from the helical thread on rod 610 causing the needle 116 to rotate, allowing the trap 316 to disengage from the distal tip 12, as shown in FIG. 1J. Thus the hub tab 616a is now located within the slot 618a and translation is now allowed. As the trigger is retracted further and as only translation is permitted, the helical thread 614 pulls the hub 616 proximally and hence the needle/trap assembly 216 along with it. Once the trigger has been fully released, the needle hub tab 616b has reached the end of the housing slot 618b and the needle/trap assembly 216 is fully retracted. The snap tab 616b on the hub 616 is deflected and snaps up, engaging the lifter 620 when it reaches full retraction. The indicator is now back in its original proximal position as shown in FIG. 1K and is visible through the proximal aperture 612A, indicating that the trap is now in the proximal portion of the device and the suture has been successfully transferred through tissue site P2. Thus, the indicator 612 has moved to its first state Thus, in the example outlined above, the indicator 612 is a mechanical indicator and indication is provided through relative movement of the indicator 612 that is visible through the proximal or distal apertures 612A and 612B. Thus the indicator 612 functions as a visual indicator. In other examples, the indicator 612 may be an audible indictor or a tactile indicator.

Further details regarding a procedure utilizing an indicator, as well as examples of an audible indicator, are found in co-pending U.S. provisional patent application Ser. No. 61/597,449, filed 10 Feb. 2012, incorporated previously herein by reference in its entirety, as well as in co-pending PCT application serial number PCT/IB2012/054204, filed 17 Aug. 2012, incorporated herein by reference in its entirety.

In one embodiment, the indicator 612 may be a mechanical indicator as mentioned above but may not involve a rotational mechanism. In other words, the indicator 612 may be coupled to the needle advancement mechanism but may be independent from the needle/trap coupling and decoupling mechanism. In one embodiment, the indicator 612 is coupled to the trap delivery mechanism and the indicator 612 is capable of indicating both when the trap has either reached or been captured at the distal tip 12 and when the trap has either reached or is positioned at the proximal portion 14 of the device. In one embodiment, the indicator 612 may comprise a first state indicating the trap proximal position and a second state indicating the trap distal position. The indicator 612 for indicating the trap position may be for example coupled to the needle advancement mechanism, where needle advancement upon actuation of a trigger to a predetermined desired location, for example to the distal tip 12, is indicated by the indicator 612 moving into an indicator second state, which is indicative of trap 316 capture at the distal tip 12. Similarly, re-actuation of the trigger in order to re-advance the needle to the predetermined desired location may allow capture of the trap and may allow the indicator 612 to move to its original or first state, which is indicative of trap return to the trap proximal position.

In an alternative embodiment of the present invention, the indicator 612 may comprise an electronic indicator means that may be wirelessly or electronically coupled to the needle advancement mechanism or the trap coupling or decoupling mechanism (for detaching/attaching the trap 316 either to the needle 116 or the distal tip 12). As an example, a sensor may be coupled to the either the needle 116 or the distal tip 12 that detects the presence of the trap 316. More specifically, a contact sensor at the distal tip 12 may be coupled via a conductor wire to an indicator 612 which is in the form of a light emitting diode (LED). When contact between the trap 316 and the distal tip is made, the information from the sensor may be relayed to the LED which may light up (indicator second state) indicating that the needle has been translated to the predetermined desired position. The lit LED may also be indicative of the trap 316 being captured at the distal tip 12.

Example 2

In additional embodiments of the present invention, embodiments of an indicator mechanism are disclosed that are useful for example with a second embodiment of a device 100. More specifically, one or more indicator mechanisms are disclosed that are usable with devices and methods for passing a suture through tissue as disclosed herein below. More specifically, the disclosure herein below provides details of the mechanism of one or more embodiments for a suture passing device, which is then followed by the details of the one or more indication mechanisms that are usable with these embodiments of the suture passing device.

More specifically, the disclosure relates to an indicator mechanism that is usable with a medical device a method of use thereof for passing suture through tissue bi-directionally. Still furthermore, the instant disclosure is directed to an indicator mechanism that is particularly usable with methods and devices that require differential traversal of a moveable member. For example where the device comprises a moveable member that is required to be moved or traversed through different distances or positions in order to achieve the desired functionality of the device and where there is limited capacity of the physician to visualize what is happening internally within the device or at the distal tip of the device due to use of the device deep within body tissues. In one particular example, the indicator mechanism of the present invention is useful in devices for passing suture bi-directionally using a hybrid approach where the moveable member such as a stylet is advanced to varying distances (either to deposit an end of the suture or to retrieve a suture trap) during multiple passes of the moveable member upon actuation of the moveable member. In one such embodiment, such an approach involves translating a suture strand in one direction directly, that is without requiring the suture to be coupled to a shuttle or ferrule, while translation of the suture in the other direction is accomplished by using a suture trap to capture the suture and translating the suture trap along with the suture. As the moveable member is required to traverse different distances in each of the two passes of the trigger actuation, the indicator mechanism of the present invention provides a useful tool for tracking the movement of the moveable member in each of the two passes.

As noted above the indicator mechanism of the present invention is usable with a hybrid device and method. A hybrid method such as is described herein-below provides several heretofore unknown and unrecognized advantages. The indicator mechanism of the present invention adds to these by enhancing the utility of the hybrid method by providing an interface that allows the user to receive an indication by which the user may ascertain that the moveable member such as the stylet has advanced to the desired distance. The advantages of the hybrid method include, but are not limited to, the following: In designs utilizing a shuttle or ferrule to carry the suture both to and from the distal tip, the first pass of the shuttle to the tip requires the shuttle to be coupled to the distal tip in some manner. This coupling can, in certain instances, be compromised by tissues or bodily fluids entering the device, or damage by the user, whereby the security and integrity of the trap is lessened. Furthermore, unintended severing of the suture during the first pass results in a free-floating shuttle or ferrule within the patient's body, whereas a hybrid approach, whereby one pass of suture is done without requiring a shuttle or ferrule, leaves only a comparatively insignificant section of suture for the same failure mode. Furthermore, in designs passing suture in both directions without utilizing a shuttle or ferrule, the ability to securely grasp a suture once it has entered the body is difficult to implement in a consistent and reproducible manner. A hybrid approach, whereby suture is captured by a suture trap prior to being translated in a second pass, provides an advantage since retrieving a suture trap is significantly more achievable. As such, a device that utilizes a hybrid approach requires the moveable member to be advanced through varying distances in two different passes of the moveable member upon two different trigger actuations. Thus, in some such embodiments, use of an indicator mechanism of the present invention provides for a means to determine if the moveable member such as the stylet has advanced to desired position at each of the trigger passes. More specifically the indicator mechanism of the present invention provides a first indication upon a first actuation of the moveable member (such as a stylet) to a first pre-determined distance, for example, to deposit an end of the suture through a suture trap at the distal end of the device. The indicator mechanism additionally provides for a second indication upon a second actuation of the moveable member (such as a stylet) to a second pre-determined distance, for example, to retrieve the suture trap along with the suture end from the device distal end. Thus, the indicator mechanism of the present invention provides an indication to the user of the internal mechanism as it relates to the advancement of moveable member (and which in some instances) may provide information to the user in terms of the operation of the device at its distal tip. As such the indicator mechanism of the present invention provides information to the user about aspects of the device operation that may be hidden within the device and/or may not be visible to the user during use (for example deep within the patient's body or areas within the patient's body that may be difficult to reach and may not readily be accessible making visualization at the distal tip of the device difficult).

In some such embodiments of a suture passing device, the device employs a suture trap, that is a component configured to capture or retain a suture once it is passed through the material to be sutured, provides a unique and unanticipated advantage over shuttles and ferrules to which the suture is pre-attached, as it facilitates certain methods utilizing a hybrid approach as discussed herein-below. An indicator mechanism of the present invention additionally provides the user with an indication that the moveable member such as a stylet has been advanced to a desired distance to facilitate use of a suture trap in such a hybrid device.

In one broad aspect, embodiments of an indicator mechanism are disclosed that are usable with a device and method described herein include steps of advancing a suture at least partially through tissue; and retrieving the suture; wherein one of the steps of advancing and retrieving comprises manipulating the suture directly, and wherein the other step of advancing and retrieving comprises manipulating a suture trap to which the suture is coupled.

In another broad aspect, embodiments of an indicator mechanism are disclosed that are usable with a device that may be used to practice the method embodiments include a bi-directional suture passer having a proximal portion for holding a portion of a suture therein; a distal tip coupled to the proximal portion and defining a tissue receiving gap there-between; a reciprocally moveable suture passing member housed within the proximal portion for translating the suture portion between the proximal portion and the distal tip; and a suture trap operable to be detachably coupled to the distal tip for capturing the suture passed by the suture passing member.

Various features of this aspect are described as well, including but not limited to indicator mechanisms comprising or included within or usable in conjunction with depth selection mechanisms, interlocking features for coupling and de-coupling components and suture routing features to minimize risk of suture damage during a suture passing procedure.

Overall Device Structure

Suture Passing Device

Figure 1L:
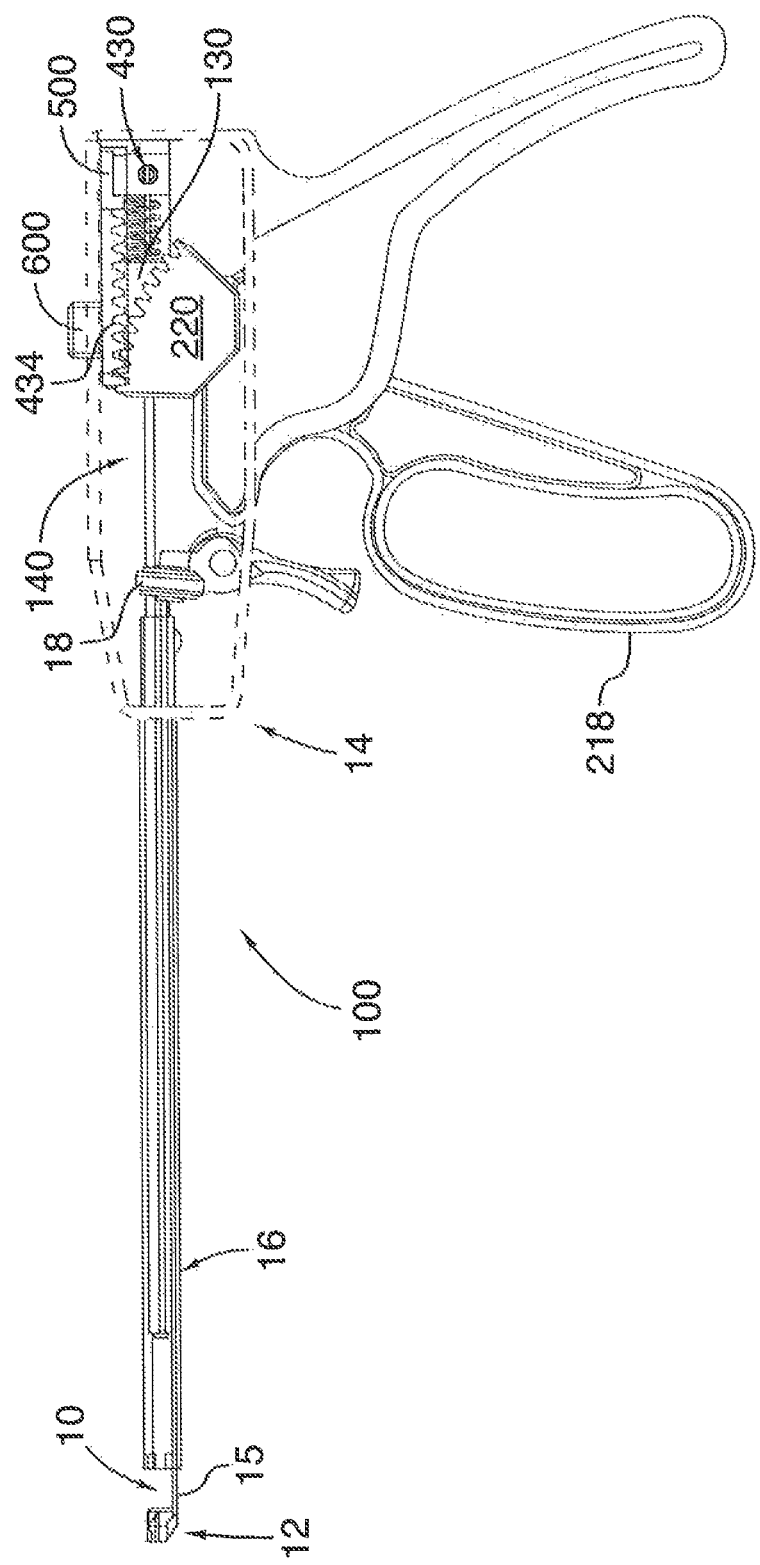

As outlined herein above embodiments of an indicator mechanism of the present invention are usable with a device 100 for treating a defect within a region of tissue. FIGS. 1L-1M illustrate one aspect of such a device for treating a defect in a tissue which is referred to herein as device 100. Device 100 may be configured for accessing tissue (e.g. disc annulus fibrosus tissue) having a defect and delivering an element such as a suture 240 through the tissue to treat the defect. In some embodiments, the suture may be resorbable. Device 100 includes a proximal portion 14 (also referred to herein as "device proximal portion 14") and a distal portion 13 having a neck portion 15 and a distal tip 12 (also referred to herein as "device distal tip 12"). Distal tip 12 is longitudinally spaced apart from proximal portion 14 and is coupled thereto via the longitudinally extending neck portion 15. According to one embodiment, distal tip 12 is coupled to a shaft 16 of the proximal portion 14 defining a tissue receiving gap 10 therebetween. Device 100 can be positioned such that distal tip 12 is positioned on a distal side of the tissue being treated and proximal portion 14 is positioned on a proximal side of the tissue.

Device 100 may comprise an actuator, actuating member or actuating mechanism (such as a trigger 218 shown in FIG. 1L) for advancing the various components within the device such as needle 116 and stylet 319, as described herein below, from the proximal portion 14 towards distal tip 12 of device 100. The trigger 218 may be used for advancing both needle 116 and stylet 319 in a direction along the longitudinal axis of device 100. As trigger 218 is actuated, both needle 116 and stylet 319 translate longitudinally from the proximal portion 14 towards distal tip 12. The needle 116 and stylet 319 may be configured to retract proximally back towards proximal portion 14 of device 100 when trigger 118 is released. As described further hereinbelow, the actuating member allows for at least two degrees of manipulation for advancing various components of the device 100 by differing amounts.

Structures internal to the handle 100 are presently described with reference to FIGS. 1L and 1M. As shown in FIG. 1L, the handle 100 comprises a handle body 14 that defines an inner chamber 140 (within which a stylet hub 430 and a needle hub 130 are located) where the stylet hub 430 is coupled to the stylet 319 and the needle hub 130 is coupled to the needle 116. The trigger 218 has a geared portion 220 that co-operatively engages with a gear rack 434 of the stylet hub 430 to allow the stylet hub 430 and the needle hub coupled thereto to slide within the chamber 140 defined by the handle of device 100.

Interlock or Needle Release Button

In some embodiments, a means for decoupling/coupling two coaxial members during translation, such as (i) a suture passing or suture holder retrieving member (e.g. stylet 319), and (ii) a tissue puncturing member (e.g. needle 116), is disclosed. The means for decoupling/coupling allows one member to travel further than the other, whereas translation of both members is affected by a single trigger. In some such embodiments, an indicator mechanism is provided that indicates coupling and decoupling of two members (such as needle 116 and stylet 319) to allow for one to travel beyond the other. As shown in FIG. 1L, needle 116 and stylet 319 are coupled using a needle release button 600 which allows the needle hub 130 to co-operatively engage with the stylet hub 430 allowing the needle 116 and stylet 319 combination to be advanced together. In some such embodiments, the interlock or needle release button 600 functions as an indicator mechanism to indicate relative advancement of the stylet 319 relative to the needle 116. In some such embodiments of the present invention, indicator mechanisms are provided that indicate release of an inhibiting member (such as a needle 116) to thereby allow a moveable member (such as stylet 319) to traverse a greater distance.

Depth Selection Mechanism

In additional embodiments indicators are provided for indicating traversal of a moveable member (such as a stylet 319) from point A to point B (for example from a first position to a second position). Such an indication mechanism is useful in hybrid device for passing suture such as device 100 where the moveable member is advanced to varying distances upon first and second actuations of the trigger. In some embodiments, an element for controlling the translation distance of a suture passing element/suture holder retrieving element such as a stylet 319 is provided, such that the translation distance of the stylet 319 at a first actuation of a trigger is different than the translation distance of the stylet 319 at a second actuation of the trigger. In order to allow for varying the distance to which a stylet 319 is advanced when the trigger 218 is actuated, certain embodiments of the present invention provide a depth selection mechanism (depth selector) 500, as shown in FIG. 1L. Thus, the depth selector 500 allows various degrees of advancement of the stylet 319 in terms of how far it can be translated relative to the needle 116. In some embodiments the depth selector 500 fits into the stylet hub 430, as shown.

Tissue Puncturing Member

In some such embodiments where an indicator mechanism of the present invention is employed, a tissue puncturing member, such as a needle 116 may be housed within the device proximal portion 14 may be used to puncture tissue to allow the suture passing member such as stylet 319 to be passed through the tissue. The needle 116 may be hollow and may define a lumen therethrough for housing a Stylet 319 and suture 240 therein. In one specific example, the needle 116 may be beveled at its distal end to allow engagement or interaction with the suture holder 316 to allow suture to be passed through a channel formed therebetween. In some embodiments, the suture passing member (e.g. stylet 319) may be coupled to the tissue puncturing member (e.g. a needle 116) for at least a part of the procedure.

Suture Passing Member

Device 100 has a suture passing mechanism capable of passing an element such as a suture 240 from proximal portion 14 to distal tip 12 (in order to pass the suture 240 from the proximal side of the tissue to the distal side of the tissue). Suture passing mechanism can include a moveable suture passing member, such as a stylet 319, which is housed within proximal portion 14. Stylet 319 is moveable between a proximal position and first or second predetermined distal positions. In accordance with embodiments of the present invention as described herein below indicator mechanisms are provided for indicating where the stylet 319 has advanced to the respective desired first or second predetermined distal positions. More specifically, the mechanism of device 100 provides for a stylet 319 is configured for passing suture knot 250 through tissue 200 and coupling suture knot 250 to suture holder 316 attached to the distal tip 12. This enables passing of suture 240 through tissue 200. In some examples, an indicator mechanism of the present invention provides for an indication that the stylet 319 has been advanced sufficiently to a first position or distance to couple the suture knot 250 to the suture holder 316. Device 100 further includes a mechanism for retrieving suture holder 316 from distal tip 12 such that suture holder 316 (and the suture coupled thereto) is passed from the distal side to the proximal side through tissue 200. Such a mechanism can include a suture holder retrieving member such as a stylet 319. Thus, stylet 319 is further configured for retrieving suture holder 316 (and thus the suture knot 250 coupled thereto) from the distal tip 12. In some examples, an indicator mechanism of the present invention provides for an indication that the stylet 319 has been advanced sufficiently to a second distance or position to retrieve the suture holder 316 and the suture knot 250 coupled thereto. Suture holder retrieving member is longitudinally translatable between proximal portion 14 and distal tip 12 and is optionally capable of reciprocal movement. Thus, in some embodiments stylet 319 is capable of passing a portion of suture 240 (which may include a knot 250), from proximal portion 14 to suture holder 316 at distal tip 12 and for retrieving suture holder 316 from distal tip 12 to proximal portion 14.

Suture Portion

In accordance with an embodiment of a device 100 of the present invention, an element such as suture 240 is housed within proximal portion 14 of device 100. According to one example, a portion of the suture 240 such as a knot 250 is held within the device proximal portion 14 adjacent to a suture passing member such as stylet 319, so that it can be passed through tissue by the stylet 319 as it advances from the device proximal portion 14 to the distal tip 12. In other embodiments, the element passed by the suture passing member may be an anchor which may be operatively coupled to the suture passing member. In these embodiments, an indicator mechanism may be provided as outlined herein below to indicate whether advancement of the moveable member such as the stylet 319 is sufficient to meet its purpose to deposit a suture portion such as knot 250 through the suture holder 316.

Slotted Needle and Shaft

In some embodiments of the device 100 of the present invention comprises features that facilitate the device 100 to pass suture through the tissue. In some embodiments as show in FIG. 1M, the device 100 described comprises a slot 117 within the needle 116 and a similar slot 117' within the shaft to allow the suture 240 to be routed to secure the suture in place. The suture 240 is guided through slot 117 to the exterior of the needle and exists through as similar slot formed within the shaft 16. The needle and shaft slots may be offset from one another. The knot 250 of the suture 240 is unable to pass through the slot within the needle, thus securing the knot 250 within the needle lumen.

Suture Holder/Suture Trap

In some embodiments, an indicator mechanism may be provided as outlined herein below to indicate whether advancement of the moveable member such as the stylet 319 is sufficient to meet its purpose to retrieve the suture holder 316. In some such embodiments the device 100 further includes a suture holder 316 that is removably attached to distal tip 12. The suture holder 316 is capable of receiving a portion of a suture 240 such a as a knot 250 from the proximal portion 14 of the device 100 from a suture passing member such as a stylet 319 and retaining it at the distal tip 12.

In one specific example, as shown in FIG. 1L, suture holder 316 is removably attached to the distal tip 12 of device 100 via a trap engagement feature such as wire 20 which interacts with a tip engagement feature of the trap (such as a window, slot or aperture) for allowing the suture holder 316 to be held within a receiving chamber 12B defined by the device distal tip 12 The wire 20 may be attached to a wire stop 18 which may allow removal of wire to decouple the suture holder 316 from the distal tip.

Detailed Device Structure

In some embodiments the structure of a device 100 is described that utilizes an indicator mechanism. The specific structure of the device 100 is described in further detail herein below with reference to FIGS. 2a-7e.

Distal Tip

In embodiments described in FIGS. 2a-3d, the device comprises a distal tip 12. The distal tip 12 may comprise a chamber 12B (FIG. 3d) for receiving the suture holder 316. The chamber 12B may define a lumen therethrough and may be open at both of its longitudinally opposed ends. In one embodiment as additionally shown in FIGS. 1a-b the distal tip may taper towards its distal end to facilitate positioning or advancement of the device 100 within a region of tissue. In some embodiments the device 100 includes a suture retaining element for retaining a portion of the suture 240 such as a suture knot 250 on a distal side of the tissue. In one embodiment, the suture retaining element may be a component of the distal tip 12. In some embodiments, as shown in FIG. 2d, the suture retaining element can be, for example a component of the suture holder, e.g. a distal opening thereof, with the suture holder being received within a the distal tip 12.

Figure 2C:
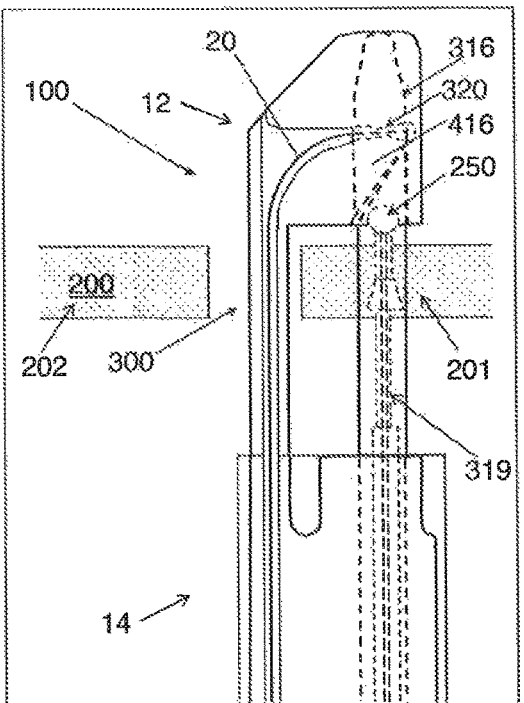

In one specific example, distal tip 12 of device 100 defines a receiving chamber 12B which holds suture holder 316 therein. As mentioned above, the suture holder 316 may be detachably coupled to the distal tip 12. Suture holder 316 comprises an engagement feature for detachably coupling the suture holder 316 to the distal tip 12. In one specific example, suture holder 316 is initially detachably coupled to the distal tip 12 within receiving chamber 12B using a wire 20 that is received within an opening or channel 320 of suture holder 316, as is further shown in FIGS. 2a-2f and FIGS. 3a-3c. The wire 20 is threaded through an opening or aperture in the distal tip 12 and into the receiving chamber 12B; it is received within the opening 320 of the suture holder 316 and secures the suture holder 316 within the receiving chamber 12B. The wire 20 may be attached to a wire stop which, when actuated, allows wire 20 to be removed. As shown in FIG. 3d, the wire 20 may be at least partially removed or retracted such that wire 20 is no longer coupled to suture holder 316, to allow disengagement of the suture holder 316 from the receiving chamber 12B of the distal tip 12. This enables retraction or retrieval of the suture holder 316 by the suture holder retrieving member which in this example comprises the stylet 319.

Mechanism for Enabling Differential Advancement of Needle and Stylet

In some embodiments of the present invention, an indicator mechanism is provided that indicates differential advancement of the needle 116 and stylet 319. Various embodiments or implementations of an engagement and release mechanism are provided to allow the stylet 319 to selectively engage with, and disengage from, the needle 116. In one example, a coupling/decoupling mechanism is provided (i) to couple the stylet hub 430 to the needle hub 130 in order to move the needle 116 and the stylet 319 together as an assembly, and (ii) to later decouple the needle hub 130 from the stylet hub 430 to allow the stylet 319 to advance on its own. The coupling/decoupling mechanism additionally functions as an indicator mechanism to indicate relative advancement of the stylet 319 with respect to the needle 116.

Example 2A (i)

Indicator Mechanism Comprising a Manual Interlock or Needle Release Button for Coupling and Decoupling the Stylet and the Needle The coupling/de-coupling mechanism may be in the form of a needle release button 600 as shown in FIGS. 4a-4g. The coupling/de-coupling mechanism functions as indicator for indicating whether the stylet 319 is capable of advancing together with the needle 116 or conversely independently from the needle 116. In its initial position the button 600 has both the needle hub 130 and the stylet hub 430 coupled. The button can be depressed manually for decoupling the two hubs. The needle release button 600 may be a spring-loaded button where the spring is biased away from the needle hub 130 in its first/initial position or the nominal position 600A. In one example, the button 600 may be connected to the needle hub 130 or may be a part of the needle hub 130. In its nominal position 600A, the button 600 provides an interference block 601 which obstructs the path the stylet hub 430 (and thus the stylet hub proximal portion 432), obstructing/impeding the movement of the stylet 319, as is further illustrated in FIG. 4d. More specifically, first the needle release button 600 in position 600A couples the needle hub 130 to the stylet hub 430 (which is driven by actuation of a trigger). By coupling the two hubs, the actuation of the trigger drives both the stylet 319, and the needle 116 forward. Thus needle release button 600 in its initial position 600A functions as the indicator mechanism and indicates that the stylet 319 is advancing in conjunction with the needle 116. This forward translation stops when the needle 116 hits the suture holder 316. At this point, the interference block 601 of needle release button 600 is obstructing/impeding the stylet hub 430.

When the button 600 is depressed (compressing the spring 603), the button 600 moves from its first position 600A to its second position 600B as shown in FIGS. 4e and 4f. Depressing the button 600 removes the obstruction created by the interference block 601 and allows the stylet hub 430, and thus the stylet hub proximal portion 432 to translate relative to the needle hub 130 (as shown in FIG. 4g) with the stylet hub proximal portion 432 depressing spring 605 against the bias. This allows the stylet 319 to advance beyond the needle 116, as the trigger 218 is continued to be pressed (as shown earlier in FIGS. 2d and 3c). As the stylet hub 430 is advanced, it continues to press against the needle release button 600, keeping it in the second or depressed position 600B. Thus, in its second position 600B, the needle release button 600 functions as an indicator mechanism to indicate that the stylet 319 is advancing independently from the needle 116 and it advancing further than the needle 116. The presently described needle release button 600 is additionally usable with an indicator mechanism comprising a depth selection mechanism as described in Example 2A (ii) herein below. In some such embodiments of the present invention, the needle release button 600 functions as a visual indicator and provides the user with a visual indication in each of its first and second positions 600A, 600B.

Example 2B (i)

Indicator Mechanism Comprising an Automatic Interlock or Needle Release Button for Coupling and Decoupling the Stylet and the Needle In an alternate embodiment, as shown in FIGS. 4h-4i, an automated system for coupling and decoupling the needle 116 and the stylet 319 is disclosed. Similar to the embodiment of the needle release button 600 described above, in the initial position, the needle release button 600 couples the stylet hub 430 to the needle hub 130. The needle release button 600, in its initial position 600A functions to indicate that the stylet 319 and the needle 116 are coupled and are advancing together. In one such example the needle release button 600, in its initial position, provides a visual indicator to the user. The button 600 can be depressed automatically for decoupling the two hubs. The button 600 is capable of automatically moving into its second position 600B to allow the stylet 319 to advance further than the needle 116 and to indicate that the stylet 319 is advancing further than the needle. More specifically, the interference block 601 of the button 600 engages with the stylet hub 430 when it is in its nominal or initial position 600A, as shown in FIG. 4h, to couple the needle hub 130 to the stylet hub 430 during forward translation. In some embodiments, the button 600 is coupled to the needle hub 130 or is a part of the needle hub 130. Thus, as the stylet hub 430 is advanced by actuation of the trigger, the needle hub 130 and the button 600 advance along with it. The button 600 comprises an overhang or hook 604 that rides over the handle body 14' of the device. In other words the hook 604 rests against the handle body that defines the inner chamber 140 (within which the stylet hub 430 and the needle hub 130 are located). The button 600 is retractable into the needle hub 130, but cannot retract until the hook 604 is positioned within a notch 142 defined within the handle body 14'.

Figure 4B:
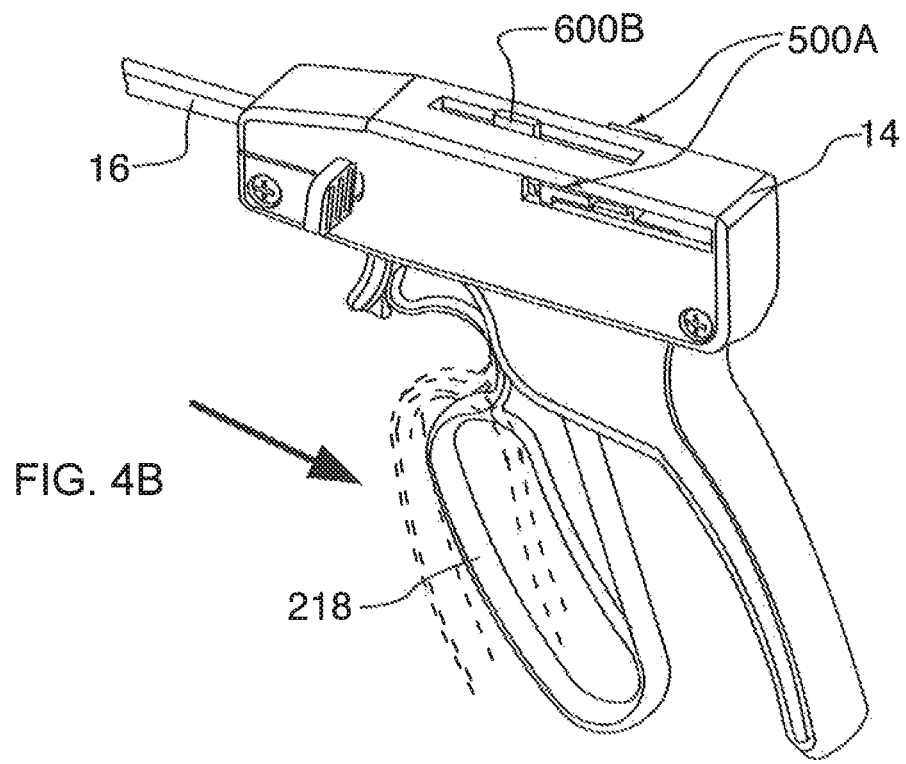
Figure 4J:
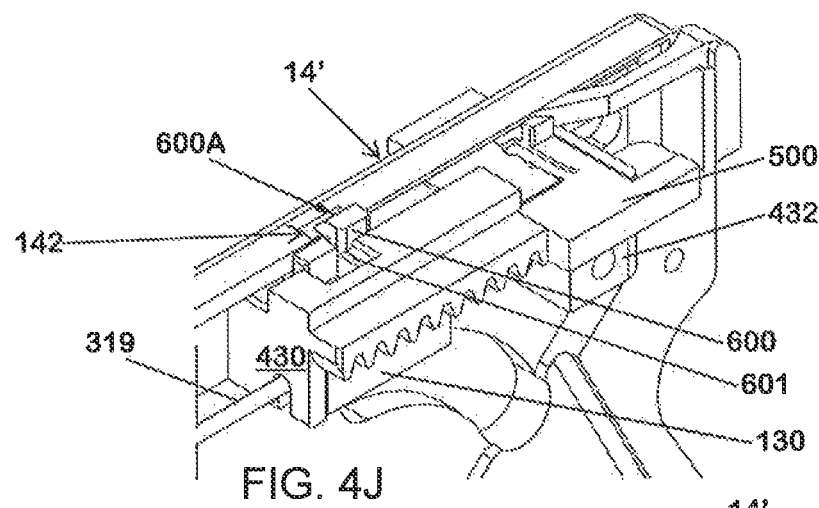
Figure 4K:
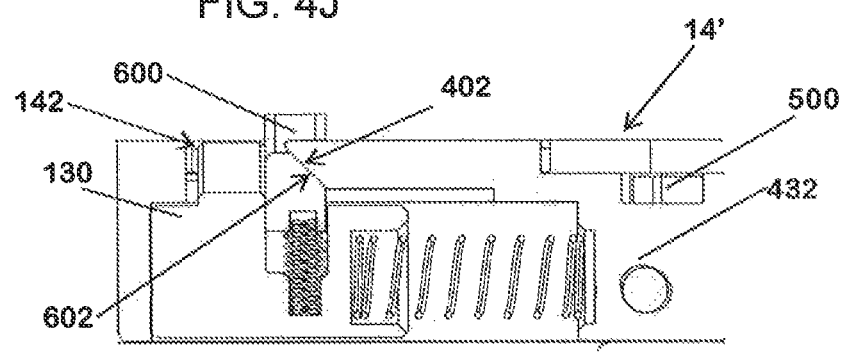
Figure 4L:
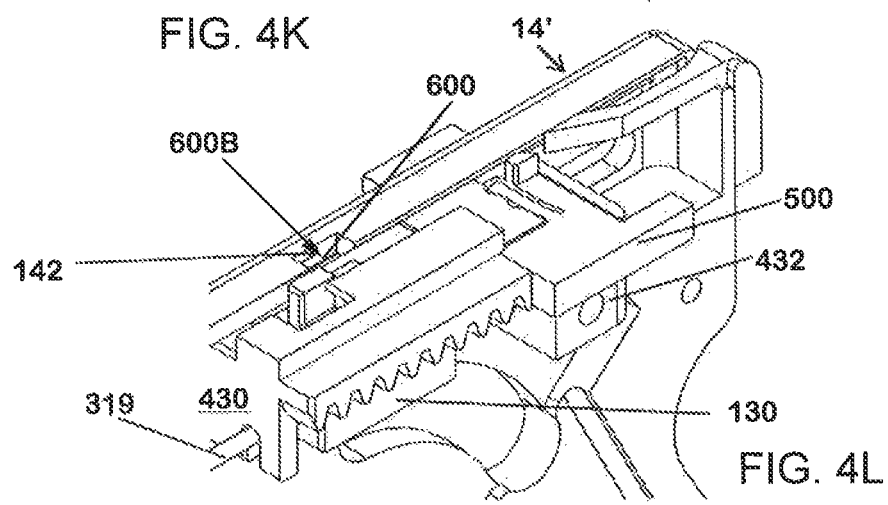
Figure 4M:
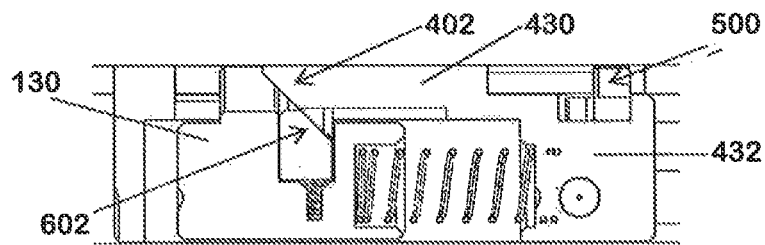

As shown, for example, in FIG. 4i, a ramp 602 is provided on the interference block 601 on its proximal face, and a corresponding ramp 402 is provided on a distal face of the stylet hub 430, that interacts with ramp 602 of the interference block 601. As the stylet hub 430 is advanced, for example, by pressing a trigger, ramp 402 of the stylet hub 430 engages ramp 602 of the interference block 601, allowing the button 600 (which includes interference block 601) to advance distally along with the stylet hub 430. The button 600 is advanced until the button 600 is aligned with the notch 142, as shown in FIGS. 4j and 4k. In other words, the needle hub 130 is pushed/advanced by the stylet hub 430/button 600 until the button 600 can retract out of the way into the needle hub 130. Once the interference block 601 is positioned within the notch 142, the interference block 601 is forced down by ramp 402 of the stylet hub 430, as it interacts with ramp 602 of the interference block 601. The button 600 now moves from its initial position 600A to its second position 600B. This allows the stylet hub 430 to be advanced further distally relative to the needle hub 130, as shown in FIGS. 4*l* and 4*m*. In other words, the portion of the stylet hub 430 that defines ramp 402, slides over the needle hub 130, thus decoupling the needle hub 130 from the stylet hub 430. As further shown in FIGS. 4*n* and 4*o*, the stylet hub 430 has advanced while the needle hub 130 has not. As such the button 600 in its second position 600B functions as an indicator mechanism to indicate that the stylet 319 is capable of and/or advancing further distally than the needle 116. In one such example the button 600 in its second position 600B provides a visual indication to the user.

The presently described needle release button 600 is additionally usable with an indicator mechanism comprising a depth selection mechanism as described in Example 2B (ii) herein below.

An Automatic Needle Release Button for Coupling and Decoupling the Stylet (Used in Conjunction with an Automatic Indicator Comprising the Automatic Depth Selector with Audible Feedback as Described Herein Below)

Figure 6A:
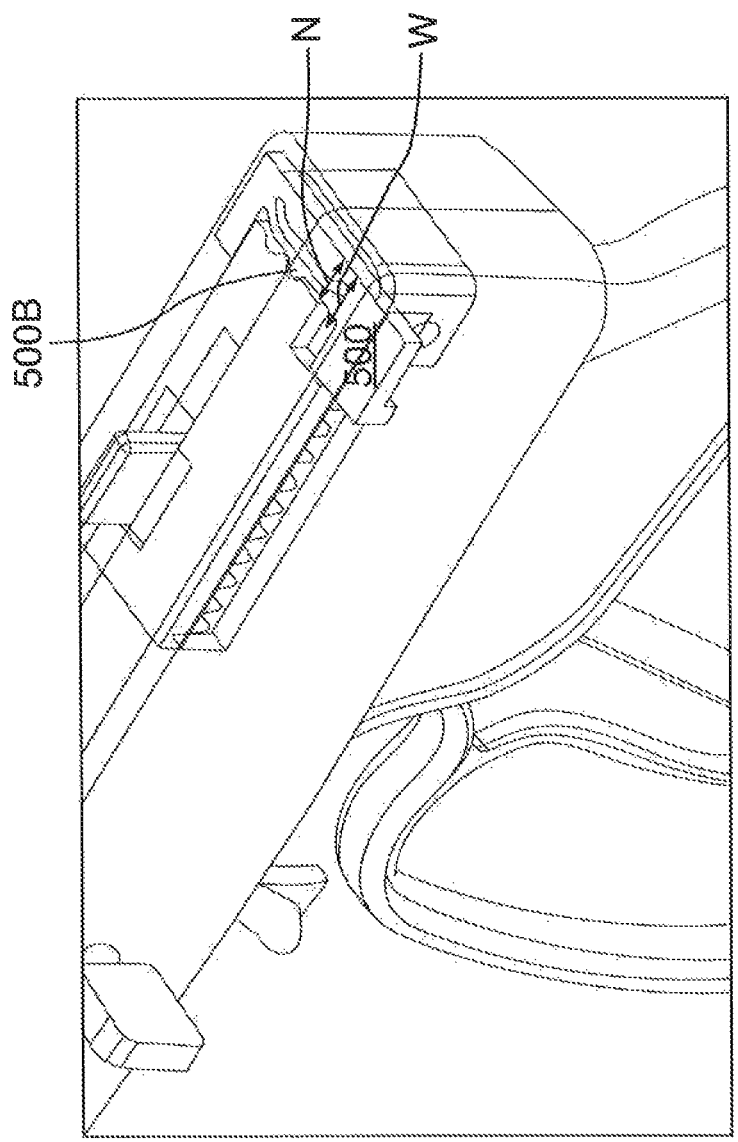

In some embodiments a needle release button 600' is provided internal to the handle body 14'. In some such embodiments, the mechanism of the needle release button 600' may be tied to an automatic indicator mechanism that is tied to a depth selector of the device 100 as described further herein-below. Presently an automatic needle release button 600' is described that allows the device 100 to allow the stylet 319 and needle 316 to be advanced together initially and then allow the stylet 319 to advance further beyond the needle 116 to allow the device 100 to achieve the functionality of a hybrid suture passing device. The mechanism of the device 100 with the needle release button 600' is described immediately herein below which allows the stylet 319 to travel together with the needle 116 initially and then beyond the needle 116 thereafter. Further herein below the automatic indicator mechanism with the depth selector mechanism described in Example 2C is disclosed that is usable with the presently described needle release mechanism 600'. The automatic indicator mechanism functions to indicate that the stylet 319 has been advanced to a first desired distance either to deposit the suture knot 250 within the suture holder 316 upon a first actuation, and to indicate that the stylet 319 has been advanced to a second desired distance to retrieve the suture holder 316 with the suture knot 250. The needle release button 600' aids in allowing the stylet 319 to advance differentially from the needle to achieve its desired functionality and the indicator mechanism within the depth selector described herein below in Example 2C provides the user with an indication that the stylet 319 has advanced to achieve its desired function at each trigger pass or actuation. The needle release button 600' initially locks the needle hub 130 and the stylet hub 430 and is automatically depressed for disengaging the two hubs, allowing the stylet 319 to be advanced beyond the needle 116 (while the needle is blocked by the suture holder 316 (FIG. 2*d*)). The embodiment of the needle/stylet interlock or needle release button 600' is shown in FIGS. 6*m*-6*x*.'. Similar to embodiments described herein previously with respect to FIGS. 4*j*-4*k* actuation of the trigger allows the stylet hub 430 to advance, and in its initial or engaged position 600A' the interlock or needle release button 600' allows or forces the needle hub 130 to advance in unison with the stylet hub 430. As discussed previously, FIG. 6*m* illustrates the device 100 prior to a first actuation of the trigger and additionally shows the interlock 600' in its first position 600A'. Furthermore, FIGS. 6*m* (i), 6*m* (ii) and 6*m* (iii) show a side bottom view of the device 100 showing the needle release button 600' in its initial position 600A'. FIGS. 6*m* (i) and 6*m*(iii) show a cut-away view showing ramp 602' provided on a proximal face of an interference block 601', and a corresponding ramp 402' that is provided on a distal portion of the stylet hub 430, that interacts with ramp 602' of the interference block 601. In one embodiment, the proximal housing or handle body 14' comprises a tab 1408 that extends from the handle body 14' into the handle inner chamber 140 defined by the handle body 14'. When the needle release button 600' is in its initial position as shown in FIG. 6*m* (ii), an overhang portion or hook 604' of the button 600' is positioned below the tab 1408 of the handle body 14' of the device 100. The tab 1408 may prevent the needle release button 600' from being prematurely depressed upwards into its second position 600B' and allows the stylet hub 430 and needle hub 130 to be advanced together. In one example, the tab 1408 functions to prevent the button 600' from being released by allowing the hook 604' to abut against or engage with the tab 1408. The button 600' is coupled to the needle hub 130 and is retractable into the needle hub 130; however, the button 600' cannot retract until the hook 604 is positioned/translated past the tab 1408 defined within the handle body 14'. In some embodiments, the needle release button 600' is coupled to the needle hub 130. The needle release button 600' may be biased towards its initial position 600A' by a biasing means. In some examples, the biasing means for the needle release button 600' comprises a spring biased mechanism. In a particular example of this, the hook 604' of the needle release button 600' is biased towards its initial position 600A' using a spring. The needle release button 600' and particularly the hook 604' has the ability to retract, when the needle release button 600' is in its depressed or second position 600B', for example under application of a force. This allows the stylet hub 430 to be advanced further distally relative to the needle hub 130. Each of these embodiments of the needle release button are described in greater detail hereinbelow with reference to the device in use.

Mechanism for Controlling the Translation Distance of the Stylet

In some embodiments of the present invention as described herein, additionally an element for controlling the translation distance of a suture passing element/suture holder retrieving element such as a stylet 319 is provided, such that the translation distance of the suture passing element at the first actuation of a trigger is different than the translation distance of the suture holder retrieving element at a second actuation of the trigger. In order to allow for varying the distance to which a stylet 319 is advanced when the trigger 218 is actuated, certain embodiments of the present invention provide a depth selection mechanism (depth selector) 500, 500', as shown in FIGS. 5*a*-5*e*, 6*a*-*h*, FIGS. 6*i*-6*l* and FIGS. 6*m*-6*x*. Thus, the depth selector 500 allows various degrees of advancement of the stylet 319 in terms of how far it can be translated relative to the needle 116. In some embodiments, the depth selection mechanism additionally functions as an indicator mechanism providing the user with an indication that the stylet 319 is either capable of travel to or has travelled the required desired distance at each pass or trigger actuation. In some embodiments the depth selector 500 fits into the stylet hub 430. The depth selector comprises a component that interferes with full advancement of the stylet 319, with the component capable of being positioned adjacent to the stylet hub 430, distal to the stylet hub 430. This interference component may be a tab (as shown in FIGS. 5a-e and 6a-h) and discussed further with respect to FIGS. 6i-6l. In other embodiments, the interference component may comprise an arm with a stop as shown in FIGS. 6m-6x. The depth selector may be actuated manually or automatically. Additionally, in some examples the depth selector may provide a visual indication or an audible indication.

Example 2A (ii)

Indicator Mechanism Comprising a Manual Depth Selector for Controlling the Translation Distance of the Stylet—(The Manual Depth Selector being Operational in Conjunction with the Manual Needle Release Button Discussed Above)

Figure 5A:
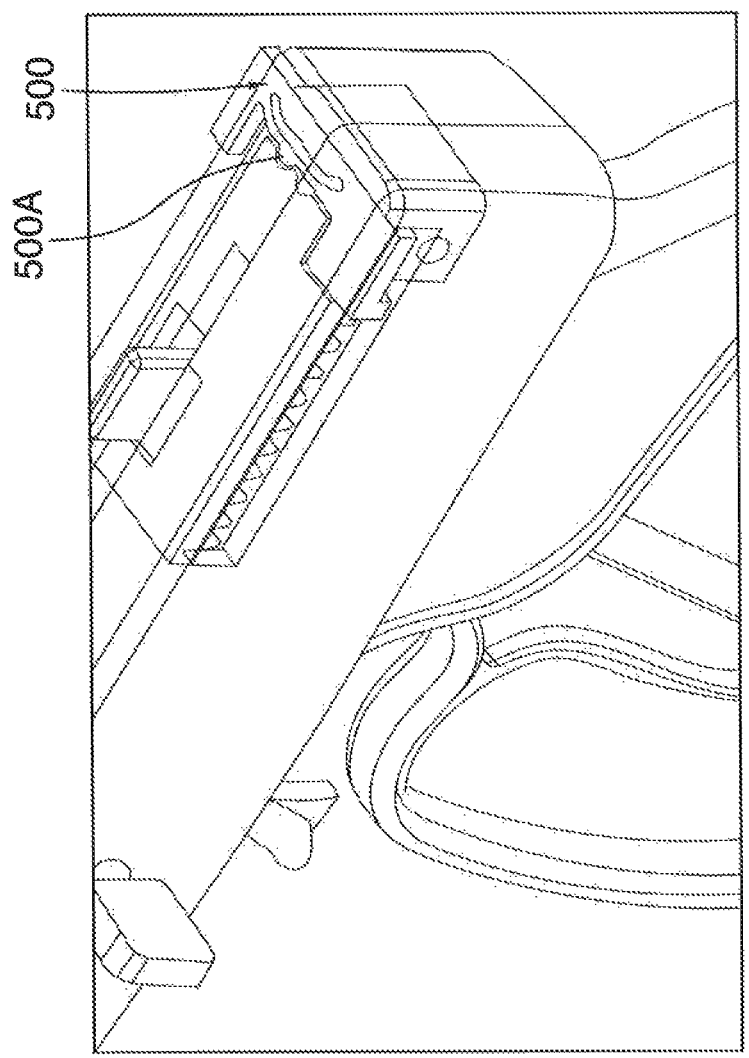
Figure 5B:
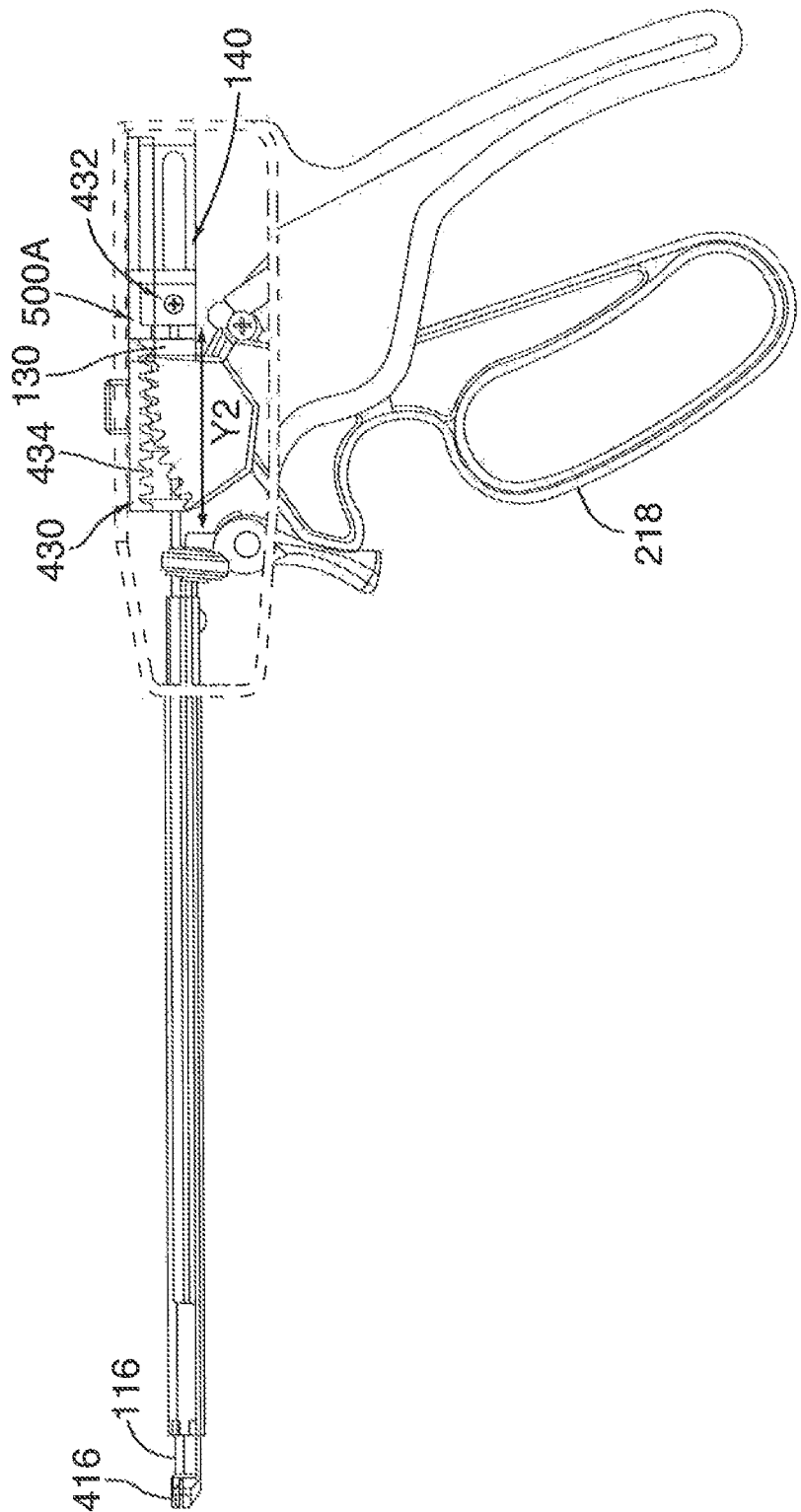

FIGS. 5a and 5b illustrate the depth selector 500 is in its first/initial or starting position or depth setting 500A and illustrate the starting and final (after trigger actuation) locations of the depth selection or adjustment mechanism 500 with respect to the handle housing. With reference to FIG. 5c, the depth selector 500 extends transversely with respect to the longitudinal axis of the device 100 and is coupled to the stylet hub 430. The depth selector 500 defines two positions, a first position 500A and a second position 500B. As such the depth selector 500 functions as an indicator mechanism that provides a visual indication in its first position to indicate that a moveable member such as a stylet 319 is moveable to a first desired distance upon a first actuation of the trigger, for example to deposit suture knot 250 within the suture holder 316. The depth selector 500 and thus the indicator mechanism defined thereby is described further herein. In the initial position 500A, an overhang or tab T of the depth selector 500 is positioned adjacent the proximal portion 432 of stylet hub 430 and abuts against a distal face of the proximal portion 432 of stylet hub 430. As shown in FIGS. 5c and 5d, In order to retain the depth selector 500 in its first position 500A, a projection 501 is provided on the depth selector that snaps into or otherwise engages with an indentation 502 within the stylet hub 430. The projection 501 is held within the indentation 502 until a transversally directed force is applied against the depth selector, to move the depth selector into its second position 500B.

With reference now to FIG. 5d, the depth selector 500 at its first position or initial depth setting 500A is positioned such that the tab T is positioned adjacent the stylet hub proximal portion 432. Thus, the tab T is positioned distal to the stylet hub proximal portion 432 between the distal surface of the stylet hub proximal portion 432 and the needle hub 130, and interferes with full advancement of the stylet in terms of how far it can be translated relative to the needle. This allows the stylet 319 to be advanced to a first predetermined distance to deposit the suture knot 250 within the suture holder 316 but not to engage therewith. The depth selector 500 is moveable into its second position by application of a transversally directed force F against the depth selector 500, thereby moving the projection 501 of the depth selector into the second indentation 503 within the stylet hub, which allows the depth selector to remain in its second position 500B. In its second position 500B, the depth selector 500 functions as a visual indicator to indicate to the user that the moveable member such as the stylet 319 is moveable to its second position upon a second actuation of the trigger, for example to retrieve the suture holder 316 with the suture knot 250. With reference now to FIG. 6e, when the depth setting 500B of depth selector 500 is in its second position the tab T of the depth selector 500 is not located between the distal surface of the stylet hub proximal portion 432 and needle hub 130. In this position, the depth selector tab T does not interfere with the advancement of the stylet hub 430 relative to the needle hub 130 and allows the stylet 319 to be advanced to a second predetermined distance to engage the suture holder to retrieve the suture holder 316

Example 2B (ii)

Indicator Mechanism Comprising an Automatic Depth Selector for Controlling the Translation Distance of the Stylet—(The Automatic Depth Selector being Operational in Conjunction with the Automatic Needle Release Button Discussed Above)

In some embodiments, as shown in FIGS. 6i-6l, the depth adjustment or selection mechanism may be automated. However, instead of requiring a manual transversally directed force to move the depth selector 500 from its initial position 500A to 500B, an automatic mechanism is provided to move the depth selector from its first position 500A to its second position 500B. As shown in FIG. 6i, a depth selector 500 is shown in its first position 500A, prior to the first trigger actuation of the trigger. The automatic depth selector 500 in its first position 500A, as described previously herein above, functions as a visual indicator and indicates to the user that the upon a first trigger actuation, the moveable member such as stylet 319 will be advanced to its first desired predetermined distance, for example to deposit suture knot 250 within the suture holder 316. The mechanism of operation of the device 100 with respect to the depth selector 500 is described further herein-below. The device proximal portion or housing 14 additionally comprises an arm 505 and a tab 506. When the depth selector is in its first position the tab 506 rests on a first side of the arm 505 and projection 501 of the depth selector is positioned within the first indentation 502 within the stylet hub 430. The tab 506 is moveable past the arm 505 upon actuation of the trigger to advance the stylet hub 430. The automatic depth selector 500 functions in a manner similar to the manual embodiment described above to limit the translation of stylet hub proximal portion 432 distally within the handle chamber 140, thus allowing the stylet 319 to be advanced to deposit the suture knot 240 within the suture holder 316. Upon release of the trigger, when the stylet hub 430 automatically retracts together with needle hub 130 to its initial position, the tab 506 is operable to hit the ramp 505b of the arm 505 forcing the depth selector 500 to move into its second position 500B, as shown in FIGS. 6k and 6l. Once the depth selector 500 automatically moves into its second position 500B, it functions as a visual indicator and indicates to the user that the moveable member such as stylet 319 is ready to be advanced to its second predetermined desired distance, for example to retrieve the suture holder 316. More specifically, in the second position 500B of the depth selector 500, the tab 506 is positioned on a second side of the arm 505. The projection 501 of the depth selector 500 engages with the second indentation within the stylet hub 430. The stylet hub proximal portion 432 may then be re-advanced with a second actuation of the trigger to allow the stylet 319 to be advanced further to engage the suture holder 316 so that it can be retracted therewith.

Example 2C

Indicator Mechanism Comprising an Automatic Depth Selector for Controlling the Translation Distance of the Stylet with an Audible Feedback—(The Automatic Depth Selector with Audible Feedback being Operational in Conjunction with the Automatic Needle Release Button Discussed Above)

In some embodiments of an indicator mechanism of the present invention, a depth selector is shown with an additional mechanism for generating audible feedback is provided which indicates when the translation of each of the suture passing element and the suture holder retrieving elements (to their respective distances) is complete. The suture holder passing element and the suture holder retrieving element can both translate to different distances when actuated. In one embodiment, as shown in FIGS. 6m-6w, a U-shaped depth stop or depth selector 500' is shown. As shown in FIG. 6m, the depth selector 500' comprises a lower arm 507 and an upper arm 508, which further comprises a stop 509. In a specific example, the depth selector 500' is pivotally coupled to the stylet hub proximal portion 432, for example using a pin. Upward rotational movement of the depth selector 500' is prevented as it abuts against the stylet hub proximal portion 432. Downward rotation movement of the depth selector 500' may also be limited by providing a tab on the depth selector 500' that engages with the stylet hub 430. The handle body 14' of the device, comprises depth selector control or guide ribs 1403, 1405 and click ribs 1404, 1406 that face/project towards the interior of the chamber 140 defined by the handle body 14'. In the initial position a tab 510 of the deflectable arm rests against an upper surface 1403a of the control rib 1403.

In the initial position, the depth selector 500' is positioned such that arm 508 is positioned between the needle hub 130 and the stylet hub proximal portion 432. The stop 509 of arm 508 is operable to contact or abut against the needle hub 130 upon a first actuation of the trigger to prevent full translation of the stylet hub 430 with respect to the needle hub 130. This allows the moveable member such as stylet 319 to be advanced distally to a first predetermined position to deposit a suture knot 250 within the suture holder 316 at the distal tip 12. Additionally the depth selector 500' comprises a lower arm 507 that functions as a spring like mechanism. The lower arm has a tab 510 that is moveable into its first deflected or biased position during the first actuation of the trigger as it rides along control rib 1403 and is moveable thereafter into its undeflected or unbiased position, to allow tab 510 to hit control rib or click rib 1404 of the handle body 14'. This allows the depth selector 500' to generate a "clicking" sound indicating the stylet advancement to its first desired distance is complete. More specifically, as the tab 510 of the lower arm 507 reaches an edge of the control rib 1403 where the control rib 1403 is thinner at its edge, the tab 510 slips past the edge allowing it to hit the click rib 1404 to generate an audible indication.

In its second position the depth selector 500' is pivoted downwards so that arm 508 is no longer positioned between the stylet hub proximal portion 432 and the needle hub 130, and does not interfere with full advancement of the stylet 430. This allows the moveable member such as stylet 319 to advance distally to a second position to engage with the suture holder. Additionally the lower arm 507 is further moveable into its second deflected or biased position as it travels along the control rib 1405 during the second actuation of the trigger and is moveable thereafter into its undeflected or unbiased position, to allow tab 510 to hit control rib or click rib 1406 of handle body 14'. More specifically, as the tab 510 of the lower arm 507 reaches an edge of the control rib 1405 where the control rib 1405 is thinner at its edge, the tab 510 slips past the edge allowing it to hit the click rib 1406 to generate an audible indication. This allows the depth selector to generate a "clicking" sound indicating the stylet advancement to its second desired distance is complete.

In some embodiments the stylet hub proximal portion 432 may be an integral part of stylet hub 430. In other embodiments, the stylet hub proximal portion 432 may be a separate component but is integrally coupled with the stylet hub 430. In some examples, the stylet hub proximal portion 432 may comprise a material that differs from the stylet hub 430. In a specific example, the stylet hub proximal portion 432 comprises stainless steel.

Each of these embodiments describing the depth selector 500 are described in greater detail hereinbelow with reference to the device in use.

Method of Use of Various Indicator Mechanism Usable in Conjunction with Depth Selection and Interlock Mechanisms Method of Use of Device 100 with Respect to an Indicator Mechanism Comprising the Manual Needle Release Button and Manual Depth Selector as Described Herein Above Example 2A (i)

Indicator Mechanism Comprising a Manual Needle Release Button

As described above, the stylet is advanced beyond the needle by various amounts during the course of a procedure. Various interlock and depth selection features (which allow the stylet 319 to decouple from the needle 116, to advance to various distances) can be embodied in various ways as described previously. In some such embodiments as described above, various indicator mechanisms may be utilized within the interlock and/or depth selection mechanism to indicate relative advancement of the stylet 319 with respect to the needle 116 and/or to indicate the advancement of the stylet 319 to varying predetermined positions. The specific embodiment of the manual needle release button is described further in terms of the operation of the device. The details of the mechanism of device 100 is described further with reference to FIG. 1a. The trigger 218 has a geared portion 220 that co-operatively engages with a gear rack 434 of the stylet hub 430 that is able to slide within the chamber 140 defined by the handle of device 100. The trigger 218 is coupled to a biasing mechanism such as a spring biased mechanism. When the trigger 218 is in a neutral position, the spring is held against the bias. As the trigger is actuated (also shown in FIG. 4a), the geared portion 220 of the trigger 218 advances the gear rack 434 which further exerts a force against the spring bias. The stylet hub 430 translates distally with the gear rack 434 causing the needle hub 130 (that is coupled to the stylet hub 430 by button 600 in its initial position 600A that indicates the stylet 319 and needle 116 are travelling together), to translate distally with respect to the handle chamber. Additionally, needle 116 is advanced with the needle hub 130.

The needle functions as a tissue puncturing member and in one example, advancement of needle 116 allows needle 116 to puncture tissue 200 at site P7. As mentioned previously, in the illustrated embodiment of FIG. 2b, the stylet 319 is housed within the needle 116 and is also passed through the tissue 200 at site P1. The stylet 319 functions as a suture passing member and the suture 240 having a knot 250 is passed through the tissue using the stylet 319. The suture knot 250 is positioned adjacent the stylet tip and is carried distally by the stylet tip as it is advanced. As the needle 116 is advanced further it abuts against a proximal face of the suture holder 316 at the distal tip 12 and the trigger 218 cannot be actuated further as shown by FIG. 2c. The needle release button 600 is then depressed (to position 600B, as shown in FIG. 4b which indicates that the stylet 319 is free to translate independently from the needle 116 and further from the needle 319), allowing the needle hub 130 to disengage from the stylet hub 430. This allows the trigger 218 to be depressed further and the stylet hub 430 to translate distally with respect to the needle hub 130. This allows the stylet hub 430 to be advanced distally such that the stylet 319 is received within the suture holder 316 to deposit the suture knot 250 therein.

Figure 2D:
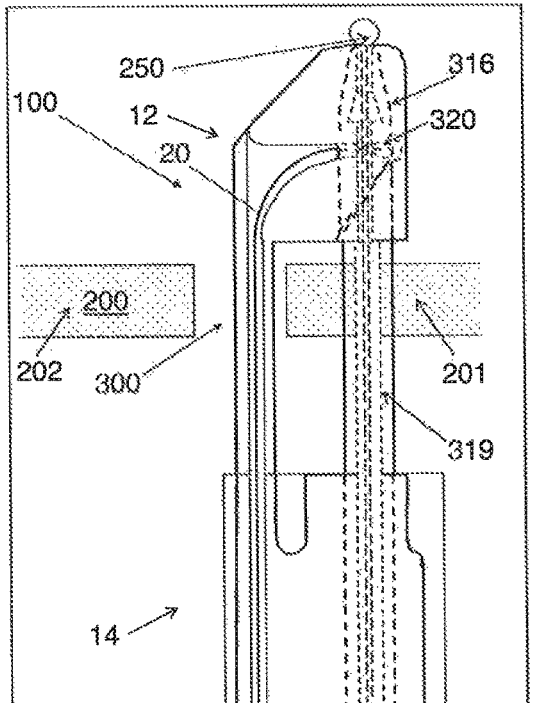
Figure 2E:
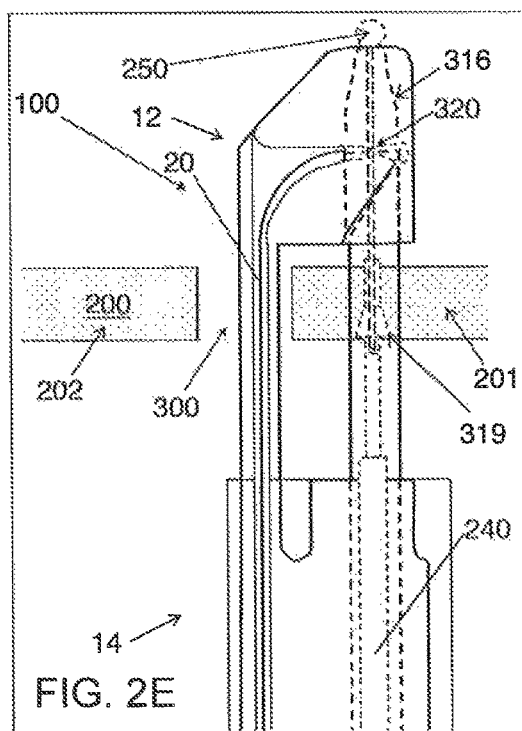
Figure 2F:
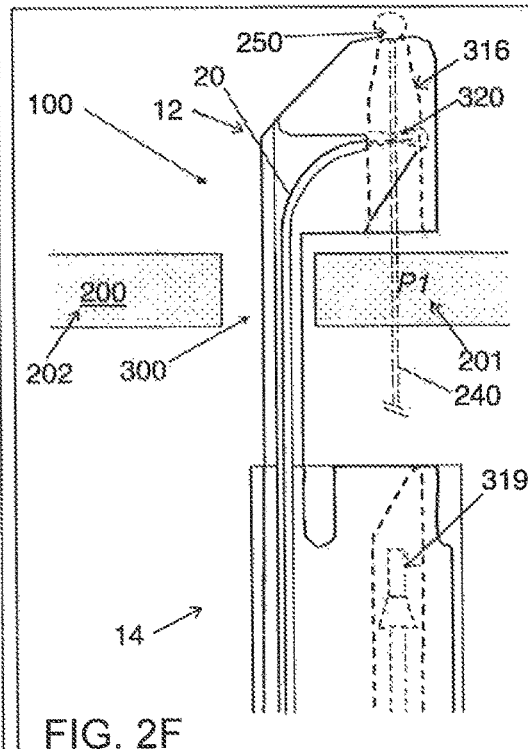
Figure 3H:
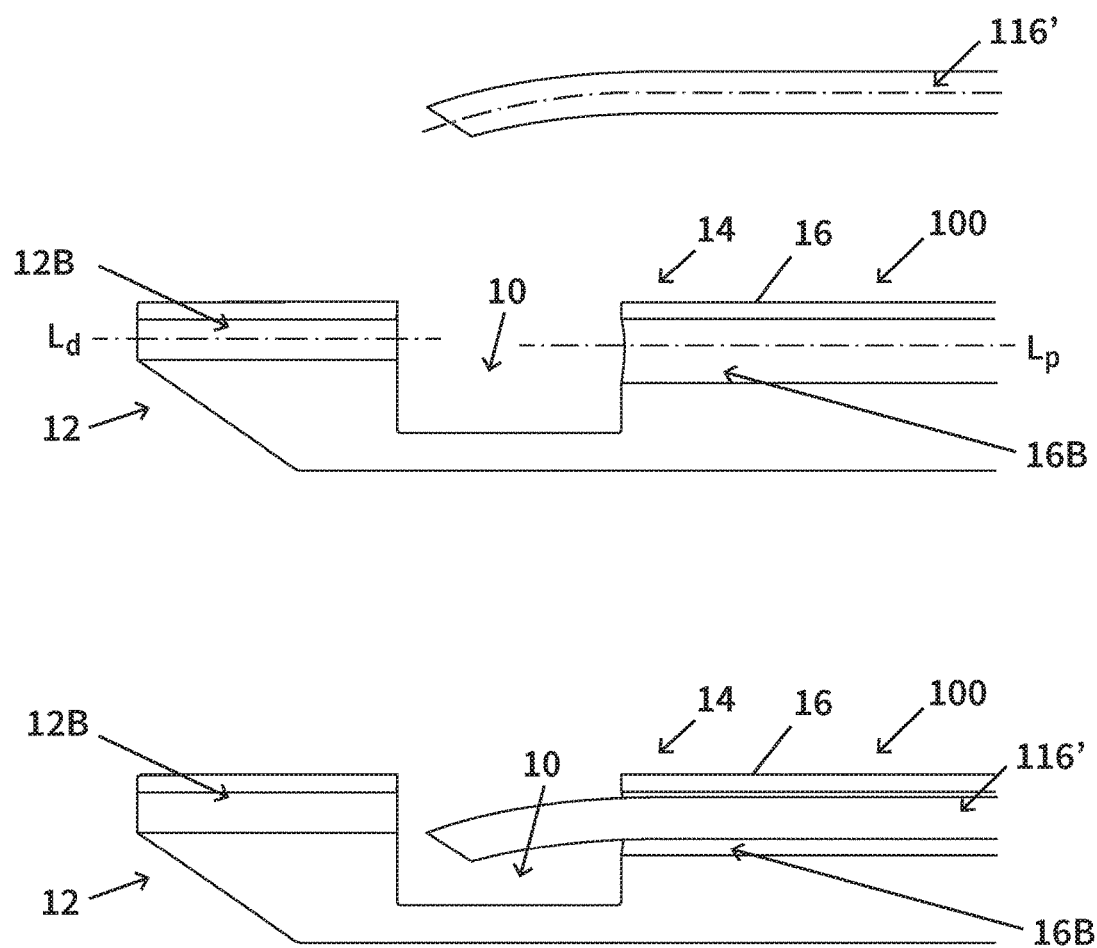

With reference to FIG. 2d, stylet 319 is advanced distally, to a predetermined distance required to deposit the suture knot 250, such that the knot 250 is coupled to the suture holder 316. The suture holder 316 comprises a suture retaining component for retaining the suture knot 250. FIGS. 4a-4g illustrate the operation of device 100 with respect to selective advancement of the stylet 319 with respect to the needle 116 to allow a suture 240 to be passed through a first segment of tissue 201. In accordance with a method of the present invention (discussed above) the device 100 is then repositioned to then allow suture 240 to be passed through a second segment of tissue 202 as shown in FIGS. 3a-3d. The trigger 218 may be re-actuated to re-advance until needle 116 abuts the suture holder 316 (FIG. 3b). Similar to the mechanism described above, the needle release button 600 may be depressed again to position 600B (indicating that the stylet 319 may be advanced further relative to the needle 116, independently from the needle 116). More specifically, the needle release button 600 is depressed to position 600B to remove the obstruction from interference block 601 to allow the stylet hub 430 to advance. The stylet 319 is then advanced distally, further than the predetermined distance required to deposit the suture knot 250, such that the stylet 319 is coupled to the suture holder 316 to retract the suture holder 316 with the stylet 319 (FIGS. 3c-3d). Thus, as can be seen in FIGS. 2d and 3c, in this specific embodiment of the present invention, the stylet 319, upon a first actuation of the trigger, is initially advanced a certain distance to deposit the suture portion such as knot 250 through the suture holder 316 (FIG. 2d). Further, upon a second actuation of the trigger (after repositioning the device on the other side of the defect), the stylet 319 is subsequently advanced a greater distance to capture the suture holder 316 (FIG. 3c). In order to allow for varying the distance to which a stylet 319 is advanced when the trigger 218 is actuated, certain embodiments of the present invention provide a depth selection mechanism (depth selector) 500, as shown in FIGS. 5a, 5b and 6a-e.

Example 2A (ii)

Indicator Mechanism Comprising a Manual Depth Selector

The mechanism of the device 100 is now described with reference to the depth selector 500 which functions as an indicator mechanism. FIGS. 5a-5e illustrate operation of device 100 using the depth selector 500 (also referred to as the depth selection or adjustment mechanism) to advance the stylet 319 through a first region of tissue to deposit the knot 250 within the suture holder 316 such that the stylet 319 functions as a suture passing member. Additionally FIGS. 6a-6h illustrate operation of device 100 using the depth selector 500 to advance the stylet 319 further to retrieve the suture holder 316 through a second region of tissue 200, such that the stylet functions as a suture holder retrieving member. As mentioned with respect to an embodiment of a device of the present invention, FIGS. 5a and 5b illustrate the depth selector 500 is in its first/initial or starting position or depth setting 500A indicating that the stylet 319 may be advanced to a first position to deposit knot 250 within the suture holder. Additionally, FIGS. 5a and 5b illustrate the starting and final (after trigger actuation) locations of the depth selection or adjustment mechanism 500 with respect to the handle housing. In accordance with the method, prior to actuation of the trigger 218, the device may be position at a defect 300 as shown in FIGS. 2a-2d, to receive a first segment of tissue 201 the tissue receiving gap 10 so that suture 240 may be passed through tissue adjacent the puncture site P1. With reference now to FIG. 5d, the depth selector 500 is initially its first position or initial depth setting 500A and is positioned such that the tab T is positioned adjacent the stylet hub proximal portion 432. Thus, the tab T is positioned distal to the stylet hub proximal portion 432. As the trigger is actuated to advance needle 116 and stylet 319, the needle release button 600 is depressed as discussed above, The button 600 moves from its initial position 600A to 600B (Not shown) to allow the stylet 319 to travel further than needle 116. At initial depth setting 500A, the tab T is positioned or contained between the distal surface of the stylet hub proximal portion 432 and the needle hub 130, and prevents the stylet hub proximal portion 432 from being further advanced to be positioned flush with the needle hub 130. Thus, travel of the stylet hub 430 distally within the handle chamber 140 is limited due to the interference created by the tab T, resulting in the stylet hub proximal portion 432, being positioned at a distance Y2 (FIG. 5b) from the distal end of the handle chamber 140. This allows the stylet 319 to extend into the suture holder 316 (for example, trap 416) so that only the distal portion of the stylet and thus the suture knot 250 is passed through the suture holder 316, as shown in FIG. 2d. Thus, allowing the stylet 319 to function as a suture passing member. The stylet 319 does not couple to suture holder 316 and is free to travel back when the trigger 218 is released.

FIG. 5e illustrates the step described above with respect to FIGS. 2e and 2f, whereby the trigger 218 is released, allowing the stylet 319 to retract while leaving the suture knot 250 engaged with the trap 416 at the distal tip 12. After depositing the suture knot 250 through tissue site P1, when the trigger 218 is retracted it allows the stylet hub 430 to translate proximally, and further retraction of the trigger 218 allows the needle release button 600 to move back to its first or original position 600A to re-engage the needle hub 130 to the stylet hub 430, as shown in FIG. 5e. In further detail, as the trigger is released, the stylet hub 430 translates proximally and spring 605 returns to its uncompressed state allowing the needle hub 130 to be spaced at its nominal distance with respect to the stylet hub proximal portion 432. In other words, in FIG. 5e, the needle hub 130 and the stylet hub 430 both return to substantially the same position they occupied in FIG. 5c prior to trigger actuation). Previously, the button 600 had been kept in the depressed position 600B by the stylet hub 430 pressing against it. As the stylet hub is retracted, it no longer presses on the button 600. The stylet 319 may then re-engage the needle 116 with button 600 moving to its first position 600A (as the spring 603 in the spring loaded button 600 recoils back to its uncompressed state), and both the stylet and needle 116 may then be automatically retracted together to their initial positions within proximal portion 14.

In accordance with FIG. 3a, the device 100 may be rotated and the position of the device 100 adjusted to allow suture 240 to be drawn through a second segment of tissue on the other side of the defect 300. For example, in order to substantially seal the defect 300, the suture 240 may be passed through tissue adjacent the puncture site P2. The depth selector may now be set to its second position or depth setting 500B as shown in FIG. 6a (also depicted in FIGS. 4c and 4e).

Figure 6B:
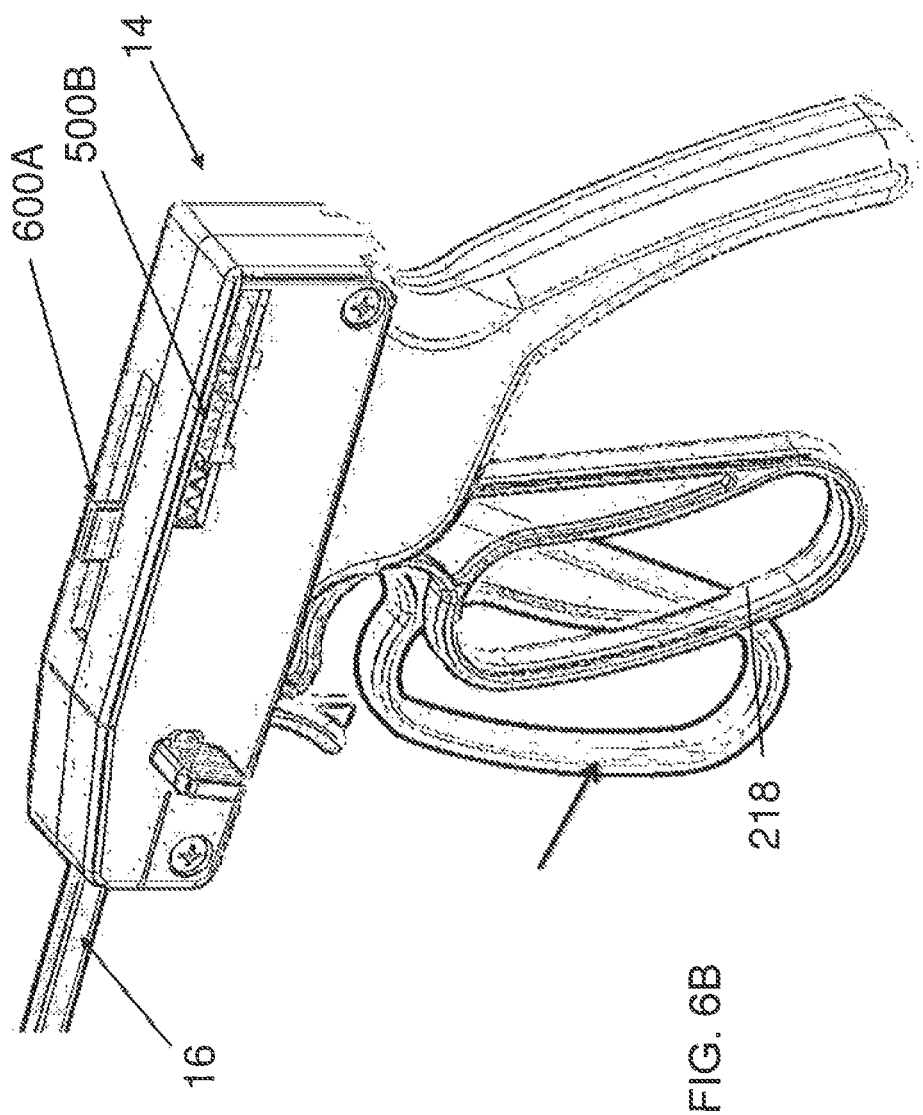
Figure 6C:
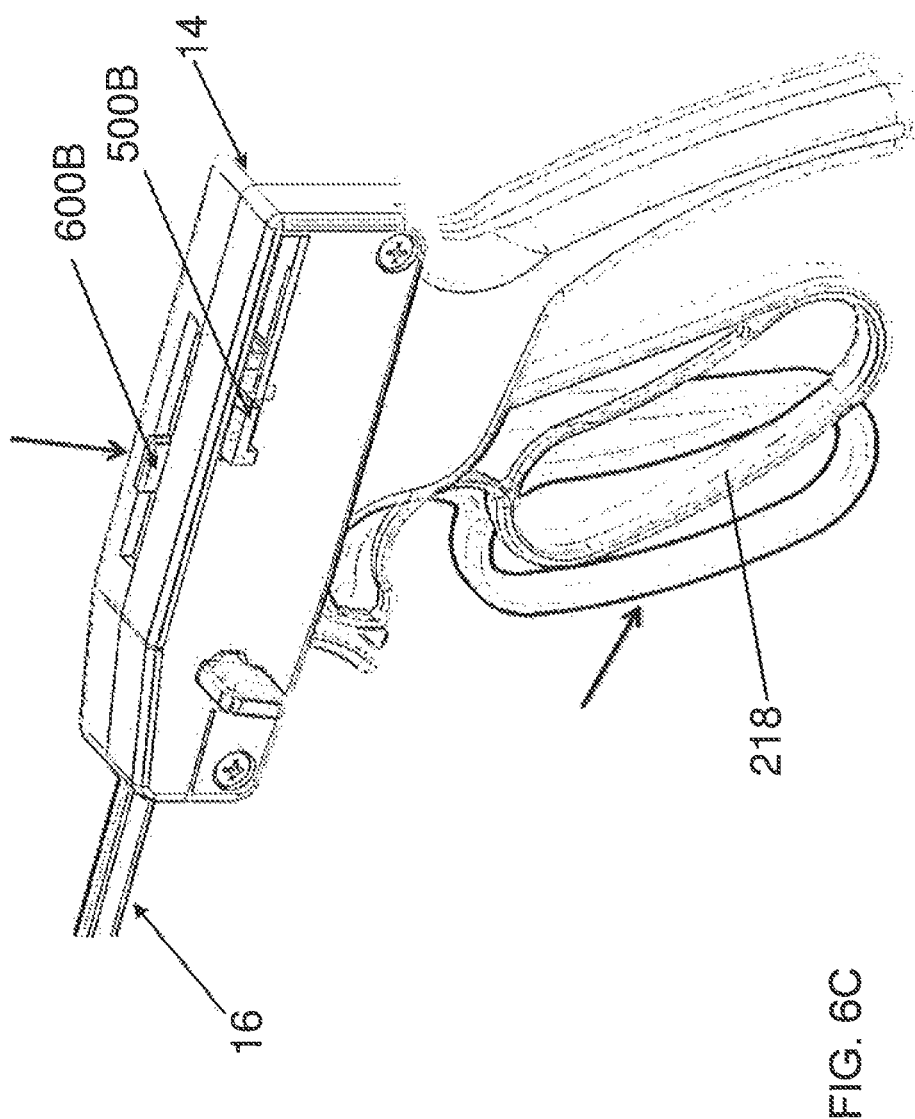
Figure 6D:
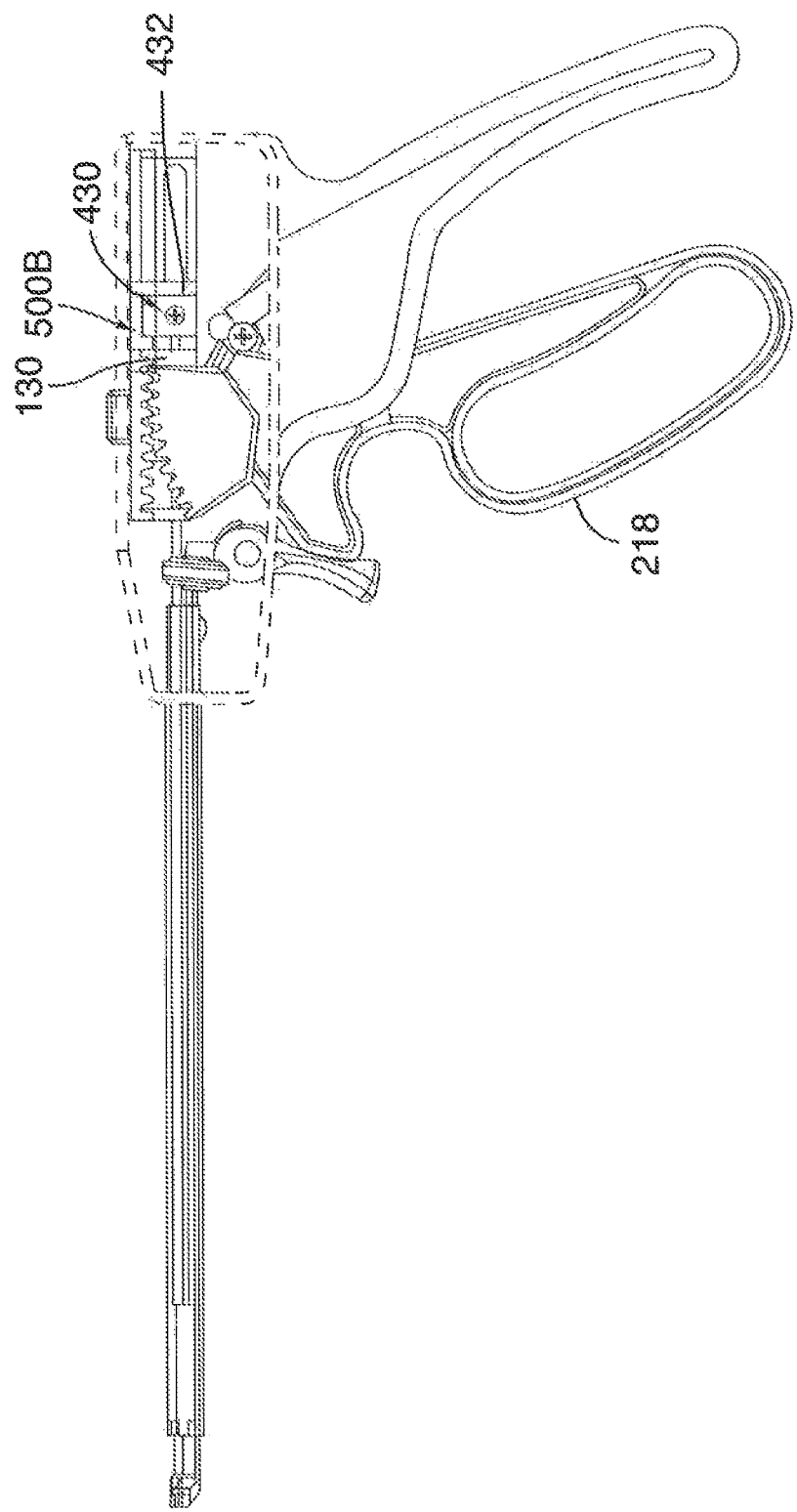
Figure 6E:
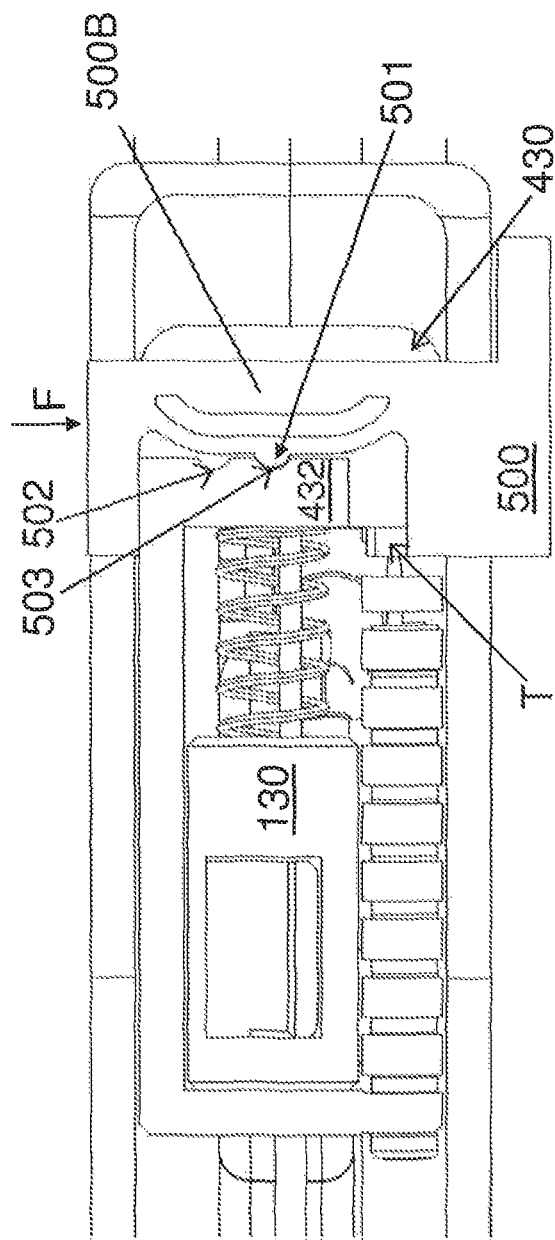

With reference to FIG. 6b, the trigger is actuated to allow the stylet 319 and the needle 116 to be re-advanced from their initial positions such that the needle 116 punctures tissue at puncture site P2 on the other side of the defect. As outlined previously, the needle 116 is advanced until it abuts against the suture holder 316 at the distal tip 12. The needle release button 600 is then depressed, as shown in FIG. 6c, so that it moves from its first position 600A to its second position 600B. This decouples the stylet 319 from the needle 116, allowing the stylet to advance into the suture holder 316 at the device distal tip 12 to engage the suture holder 316, as shown in FIG. 6d and as described previously with reference to FIG. 3c. Thus, allowing the stylet 319 to function as a suture holder retrieving member. Actuation of the depth selector 500 to its second depth setting 500B, as shown in FIG. 6a, allows the stylet 319 to advance to a second distal position (e.g. a second predetermined distal position) which is further distally, relative to the position described above with reference to FIGS. 2d and 5b and which allows stylet 319 to engage or couple to suture holder 316. As such the second depth setting 500B of the depth selector functions to indicate that the stylet 319 is advanceable to its second pre-determined position to retrieve the suture holder 316.

Figure 6F:
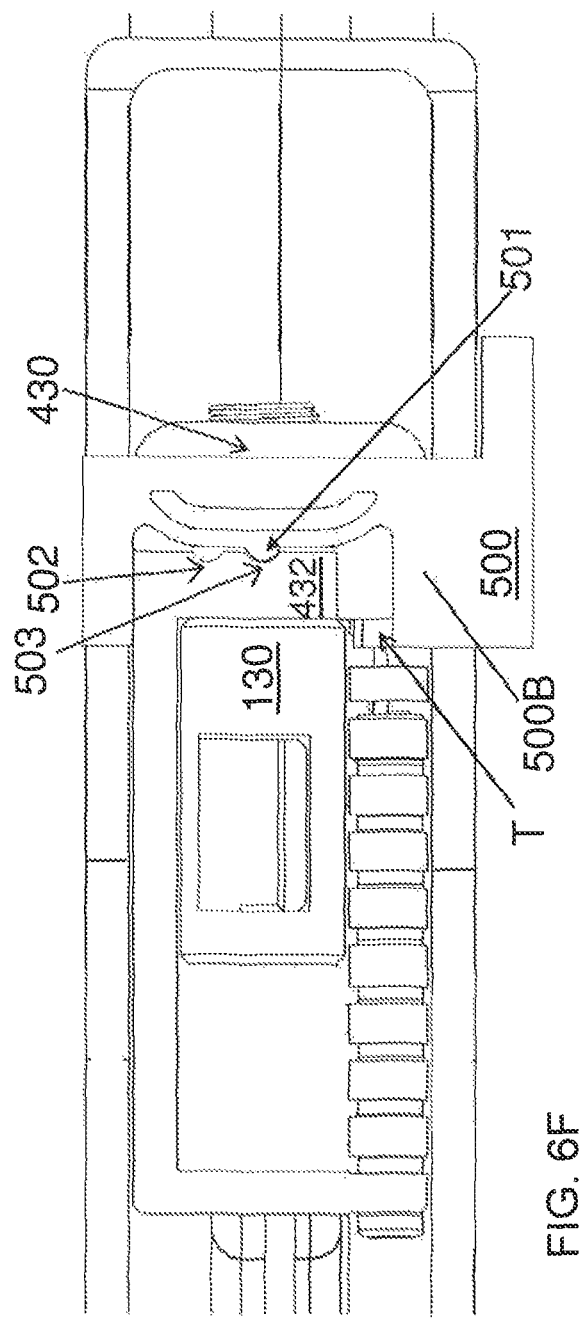
Figure 6G:
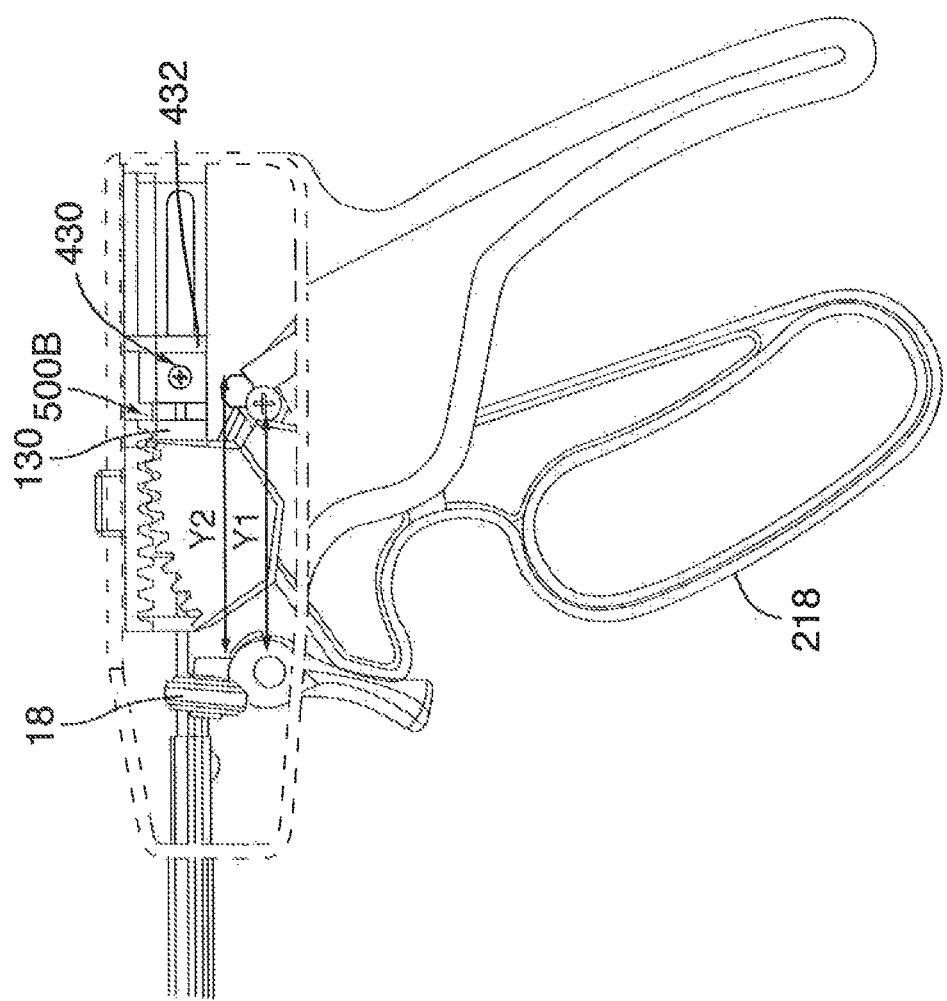

As shown in FIG. 6e, the depth selector 500 may be moved into its second position by applying a transversally directed force F against the depth selector 500, thereby moving the projection 501 of the depth selector into the second indentation 503 within the stylet hub, which allows the depth selector to remain in its second position 500B (until a counter force is applied to move it back to its first position). With reference now to FIG. 6e, when the depth setting 500B of depth selector 500 is in its second position the tab T of the depth selector 500 is no longer located between the distal surface of the stylet hub proximal portion 432 and needle hub 130. In this position, the depth selector tab T does not interfere with the advancement of the stylet hub 430 relative to the needle hub 130. In other words, the tab T is located external to the travel path of stylet hub 430. As the stylet hub 430 is advanced within the handle chamber 140 relative to the needle hub 130, the distance the stylet hub 430 travels distally is not limited by the depth selector 500. In an alternative embodiment, during the second trigger actuation as the stylet 319 is advanced a second time, the distance the stylet hub 430 travels may also be limited by the depth selector 500. This allows the stylet hub proximal portion 432 to be positioned flush against the proximal surface of the needle hub 130, i.e. the stylet hub proximal portion 432 travels maximally with respect to the needle hub 130 within the handle chamber 140, as shown in FIG. 6f. Thus, as illustrated in FIG. 6g, using the second depth setting 500B results in the stylet hub proximal portion 432 being positioned at a closer distance Y1 from the distal end of the handle chamber 140, compared to distance Y2 using the first depth setting 500A. This enables further advancement of the stylet which allows the stylet 319 to extend into the suture holder 316 (such as trap 416) so that it engages the suture holder 316 as shown in FIG. 3c.

With reference now to FIG. 6h, when the trigger 218 is released, the biasing mechanism coupled to trigger 218, such as the spring-biased mechanism, automatically urges the gear rack 434 of the stylet hub 430 to translate proximally within the handle chamber 140. The stylet 319 is then retracted when the trigger 218 is released, allowing the suture holder 316 to be retracted along with the stylet 319 (as previously discussed with respect to FIG. 3d).

As noted above with respect to FIG. 3d, the distal tip 12 of device 100 defines a receiving chamber 12B. The receiving chamber 12B receives the suture holder 316 therein. The suture holder 316 comprises an engagement feature for releasably coupling the suture holder 316 to the distal tip 12. In one specific example of this, the suture holder 316 is initially secured within the receiving chamber using a wire 20 that engages the suture holder 316. The wire 20 may be attached to a wire stop 18, shown in FIG. 6h. The wire 20 may be removed by pulling the wire stop 18, to allow disengagement of the suture holder 316 with the receiving chamber 12B. This allows retraction of the suture holder 316, upon release of the trigger 218 (FIG. 6h).

Example 2C

Figure 6N:
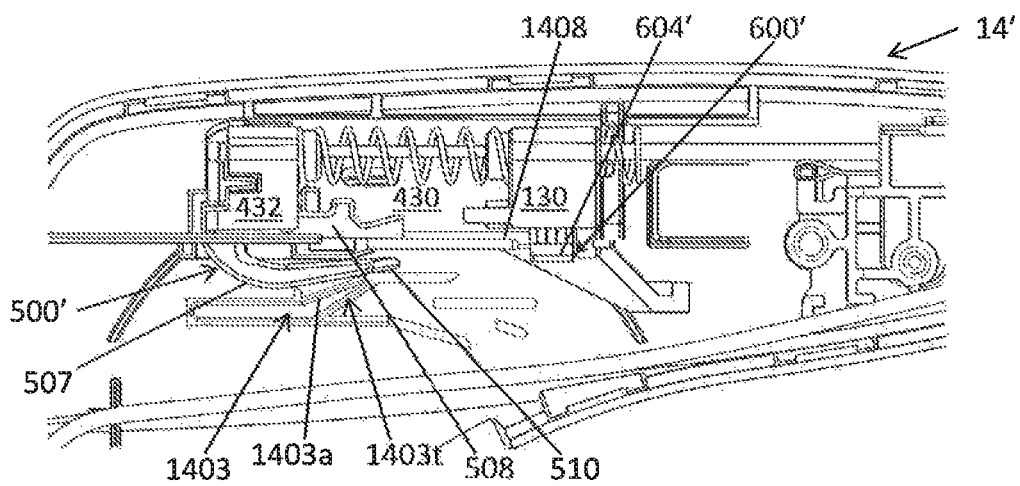
FIGS. 6M-6X illustrate a device and method in accordance with yet another alternative embodiment of the present invention.
Figure 6O:
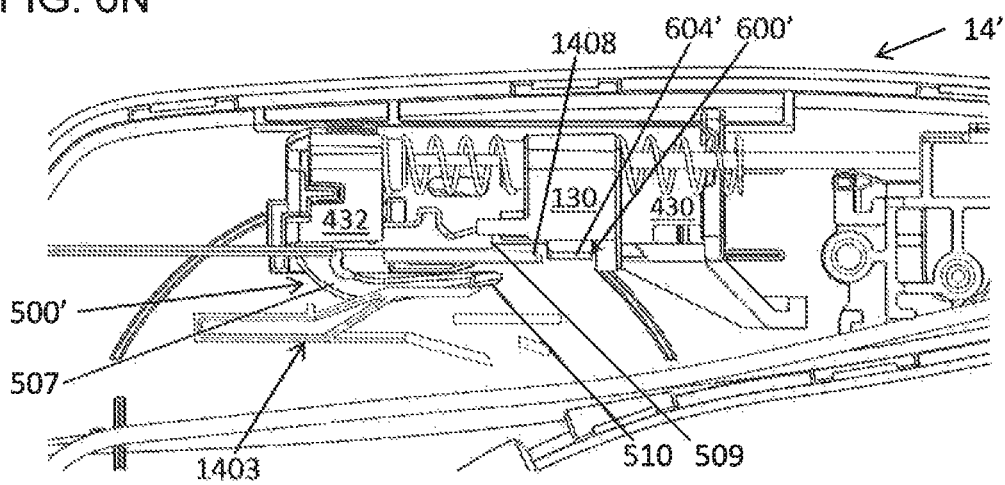
Figure 6P:
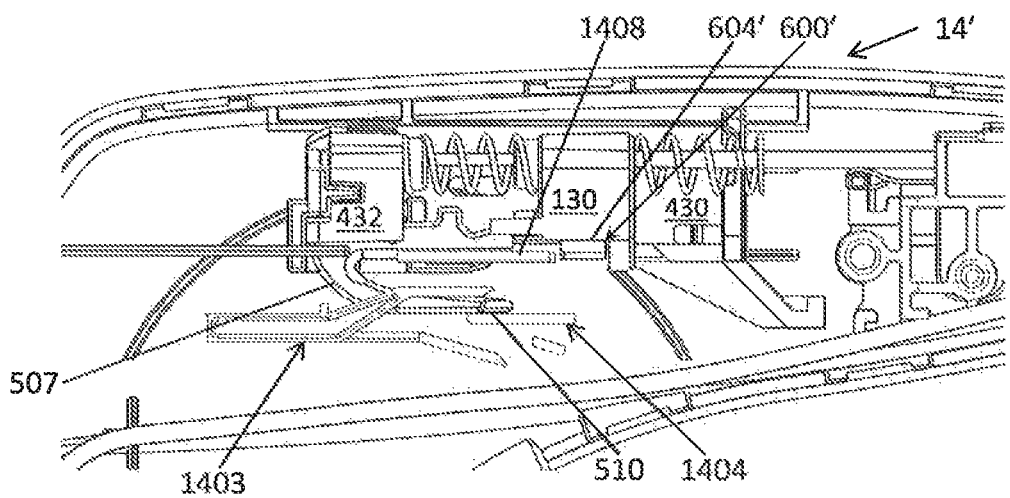
Figure 6Q:
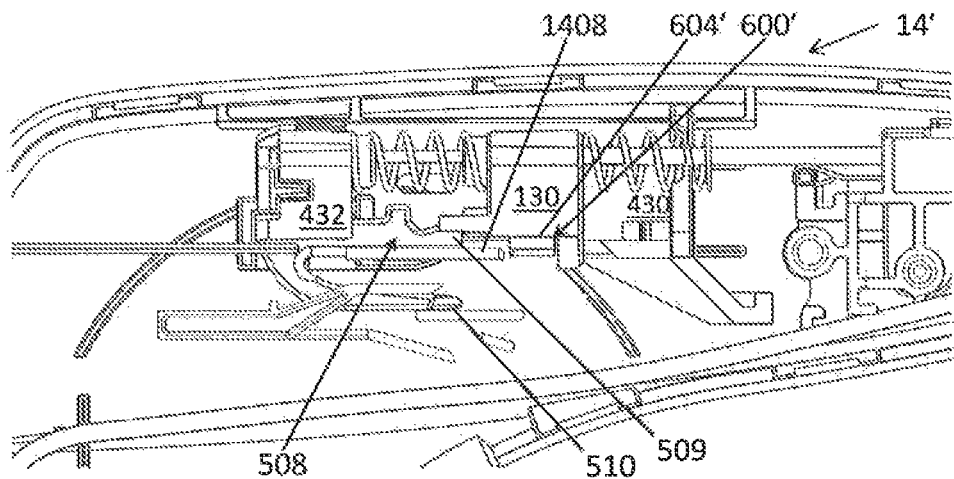
Figure 6R:
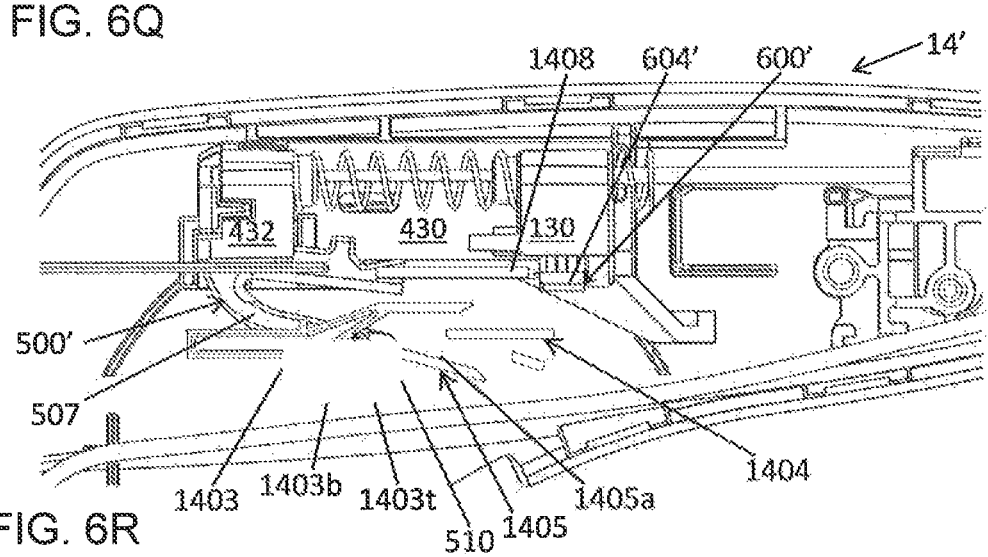
Figure 6S:
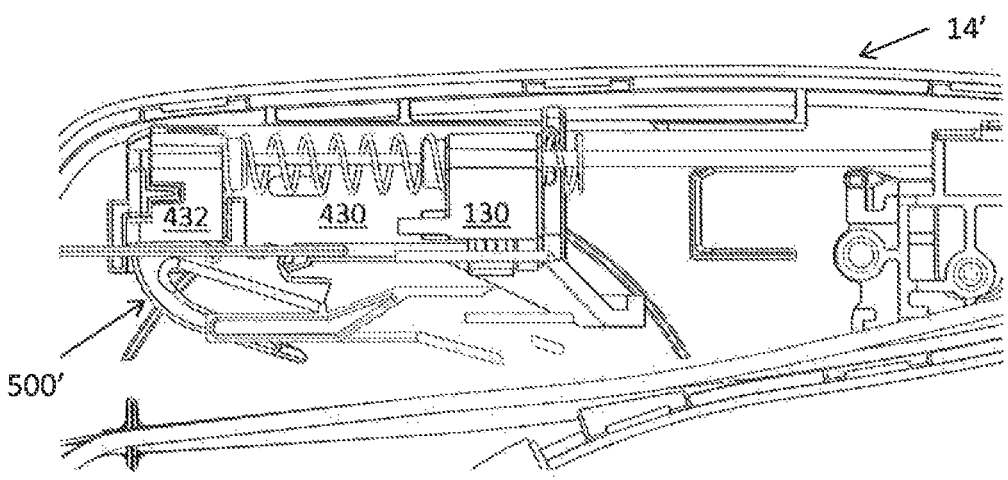

Method of Use of One or More Indicator Mechanisms Comprising an Automatic Needle Release Button with an Automatic Depth Selector Having a Mechanism for Generating an Audible Feedback as Described Herein Above Method of Using an Indicator Mechanism Comprising an Automatic Depth Selector with a Mechanism for Generating an Audible Feedback An alternative embodiment of an indicator mechanism comprising the depth selector 500' is described with references to FIGS. 6m-6x that comprises an additional mechanism for generating audible feedback indicating when the translation of the moveable member such as the stylet 319 to each of its respective first and second translation distances is complete. During the first actuation of the trigger, the moveable member such as the stylet 319 is moveable between a first position and second position for transferring a component such as the suture knot 250. More specifically, during the first actuation of the trigger, the stylet hub proximal portion 432 translates distally, allowing the depth selector 500' coupled thereto to translate distally. In one such example, the depth selector 500' defines a part of an indicator mechanism that is coupled to the moveable member such as the stylet 319 for indicating a position of the stylet 319. The indicator mechanism comprises at least two components that are functional to interact with one another to produce an indication. More specifically, one of the at least two components of the indicator mechanism is coupled to the moveable member. In this particular case the lower arm 507 of the depth selector 500' is coupled to the mechanism for advancing the stylet 319. As such, the lower arm 507 is indirectly coupled to the moveable member which is the stylet 319. Upon actuation of the trigger and thus the moveable member such as the stylet 319, the depth selector 500' (and as such one of the at least two components of the indicator mechanism, which in this instance comprises the lower arm 507) is moveable within the housing 14' upon actuation of the moveable member such as the stylet 319. During the first actuation of the trigger, as shown in FIG. 6n, the lower arm 507 of the depth selector 500' functions like a spring and is deflectable and flexes (into a biased position) as tab 510 rides up along an upper surface 1403a of the control rib 1403 (which includes a tapered section 1403t). As such, the deflectable lower arm 507 functions as a biased component of the indicator mechanism that forms a part of the depth selector 500'. In one such instance, where the device 100 comprises a housing 14', the other of the at least two components of the indicator mechanism comprises a feature of the housing 14', such as the click rib 1404 as outlined herein below. During the first actuation, as the lower arm 507 rides along the tapered section 1403t and the portion of the control rib 1403 beyond it, the lower arm 507 moves into a more biased or deflected position. Thus, the lower arm 507 moves from its un-deflected position into its first deflected position. Contrary to this, the upper arm 508 may not flex and remains in its initial position. In one example, the upper arm 508 is in contact with the stylet hub proximal portion 432 which limits the upward movement of arm 508.

As the stylet hub proximal portion 432 and the depth selector 500' are advanced further, the tab 510 on the lower arm 507 reaches the end of the control rib 1403 just prior to the stop 509 contacting the needle hub 130, as shown in FIG. 60. As the tab 510 on the lower arm 507 advances past the end of the control rib 1403 (which in some examples may be a thin edge at the end of the control rib 1403 as shown), the arm 507 springs back to its un-deflected or unbiased initial position as shown in FIG. 6p. As it deflects back to its initial position it collides with click rib 1404, thus making a "click" sound. The "click" sound indicates that the translation of the suture passing element, such as the stylet 319 to its desired translation distance is complete. For example, the "click" may indicate that the stylet 319 has been advanced to a distance to allow the stylet to deposit a suture through a suture holder. Thus, in a particular instance, the click rib 1404 functions as a rigid member that is a non-biased component of the indicator mechanism. More particularly the click rib 1404 is a feature that is integral with the housing 14'. As such, in one such embodiment of the present invention, the interaction between the at least two components of the indicator mechanism (such as the lower arm 507 of the depth selector 500' and the click rib 1404 of the housing 14') occurs automatically upon actuation of the moveable member such as the stylet 319, thereby providing an automatic indication of the movement of the moveable member such as the stylet 319 between the first and second positions. In the particular example discussed herein the indication comprises an audible indication. As shown in FIG. 6q (in which the components are in positions similar to those shown in FIG. 6p), the stop 509 on the upper arm 508 touches the needle hub 130 and thus limits further forward or distal translation of the stylet hub proximal portion 432. As the trigger is released as shown in FIG. 6r, the stylet hub 430 retracts proximally towards its initial/starting position. As the depth selector 500' is retracted with the stylet hub 430, in some examples, tab 510 of the lower arm 507 slides along and past the proximal end of the click rib 1404, and is then guided along an upper surface 1405a of control rib 1405. The tab 510 of the lower arm 507 then engages with the control rib 1403 pivoting the depth selector 500' downwards. In some embodiments, a lower surface 1403b of the control rib 1403 along the tapered section 1403t may additionally guide/force the tab 510 of the lower arm 507 down, thus guiding/forcing the depth selector 500' to deflect or pivot into its second position. In one such example, as the trigger is released the tab 510 engages with and hits the lower surface 1403b of the control rib 1403 along or adjacent the tapered section 1403t. The lower surface 1403b adjacent or along the tapered section 1403t may additionally functions as a component of the indicator mechanism. More specifically, it is a feature that is integral with the housing 14' and functions as a rigid member that is a non-biased component of the indicator mechanism. In one such example the arm 507 functions as a moveable component of the indicator mechanism that interacts with the lower surface 1403b along of the control rib 1403 to provide an audible indication indicating that the moveable member such as stylet 319 has been retracted, for example to its initial or starting position. In one such example, as the trigger is released the stylet 319 retracts and the depth selector 500' and as such the arm 507 retract along with it. Once the tab 510 of the arm 507 hits the lower surface 1403b adjacent or along the taper 1403t, the clicking sound indicates to the user that the first trigger actuation and release is compete and the moveable member such as stylet 319 as well as the needle are now in their initial or starting position and the device 100 is ready for the second actuation of the trigger. Once the stylet hub 430 has been fully retracted upon release of the trigger, as shown in FIG. 6s, the depth selector 500' is now in its second position and is ready for the second actuation of the trigger. The depth selector 500' has been rotated downwards such that it will not contact the needle hub 130, and will not impede/limit the movement of the stylet hub 430.

Figure 6T:
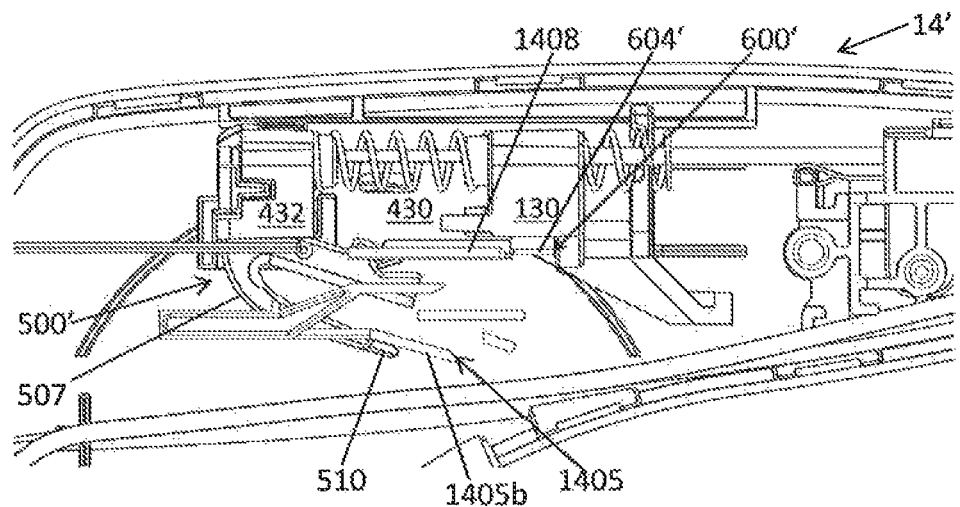
Figure 6U:
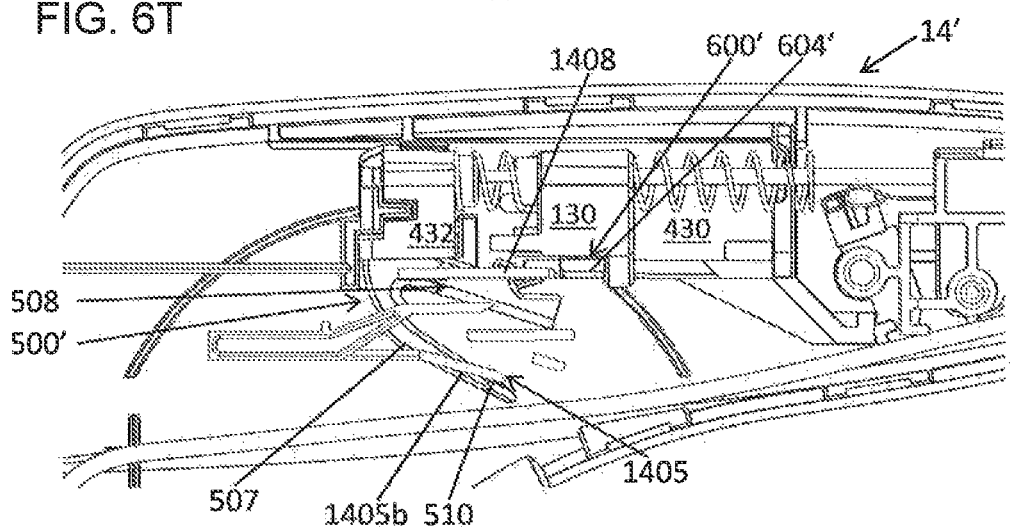
Figure 6V:
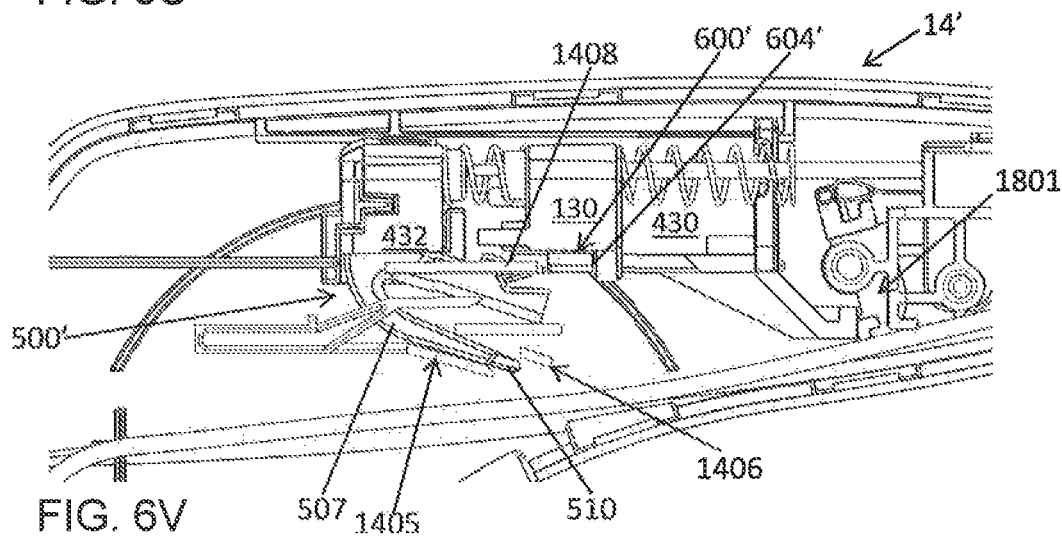
Figure 6W:
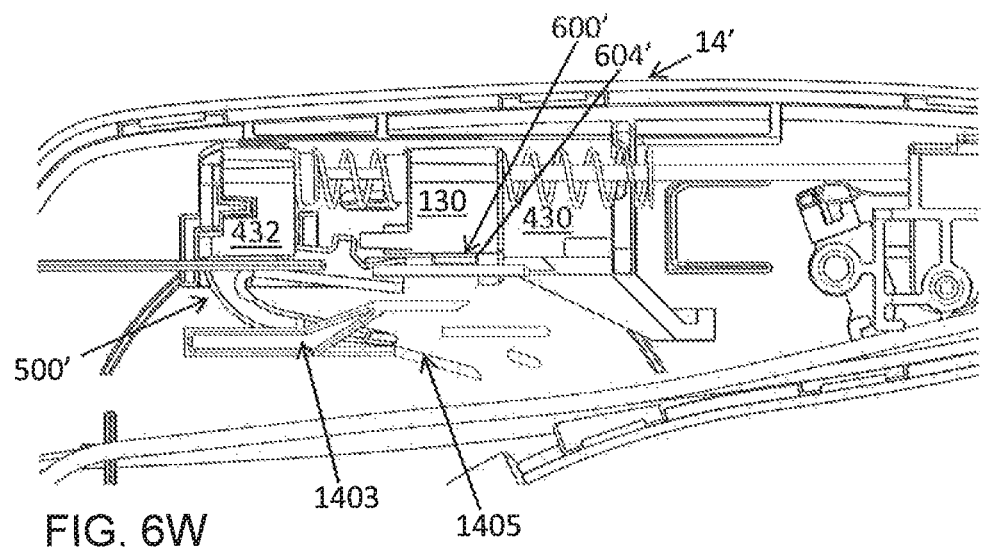
Figure 6X:
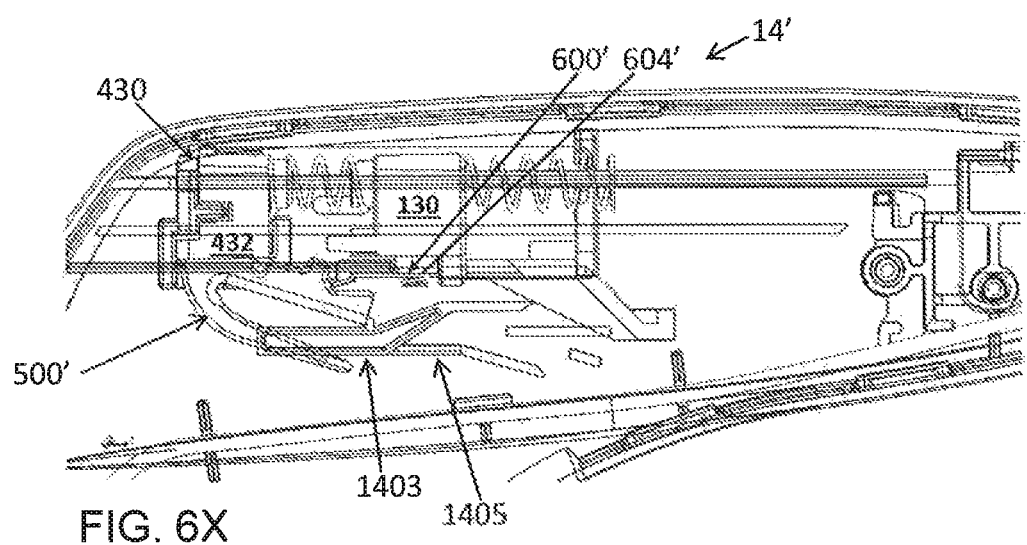
Figure 6M:
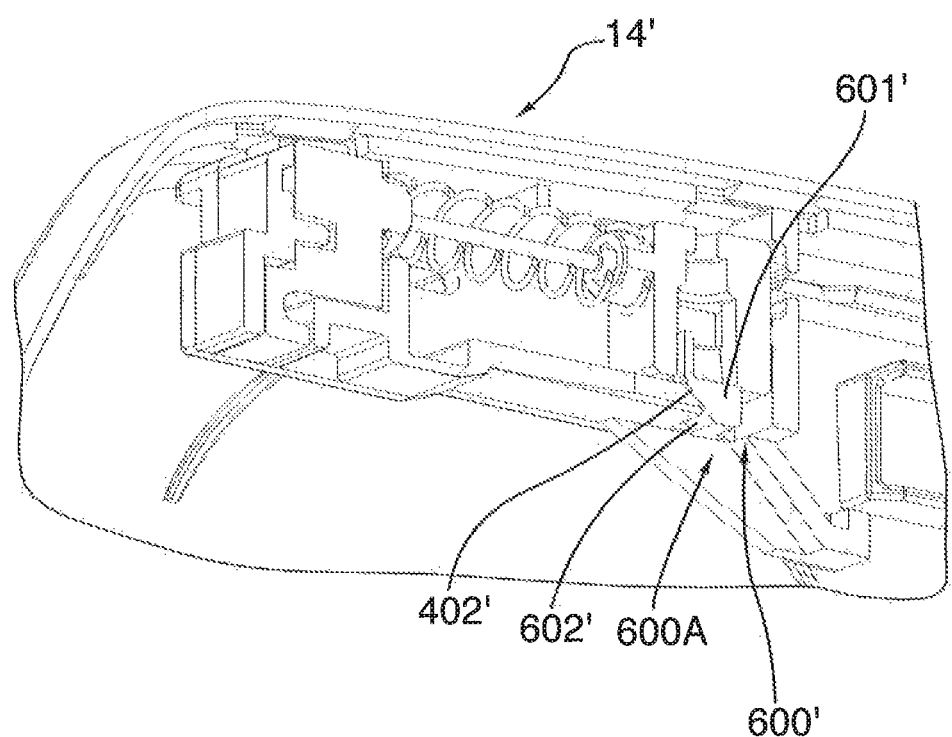

As the trigger is actuated again to advance the stylet hub 430, the depth selector 500' remains in its second position as shown in FIG. 6t with tab 510 of lower arm 507 translated distally until it abuts against or engages the lower surface 1405b of the guide or control rib 1405. The lower arm 507 is deflectable and defines a deflectable member that is a part of the depth selector 500', and as before functions as one of the at least two components of an indicator mechanism of the present invention. The depth selector 500' and as such the deflectable arm 507 is indirectly coupled to the moveable member such as the stylet 319, as the movement of the stylet 319 is tied to the movement of the depth selector 500' upon actuation of the trigger. As such, the indicator mechanism is coupled to the moveable member (e.g. stylet 319) for indicating a position of the moveable member, and indicator mechanism comprises at least two components that are functional to interact with one another to produce an indication (such as lower arm 507 of the depth selector 500' and the click rib 1406 of the housing 14' as outlined herein below). More specifically, upon the second actuation of the trigger, as tab 510 of the lower arm 507 rides down/along the a tapered portion of the lower surface 1405b of the control rib 1405, the lower arm 507 flexes and moves into a second deflected position or biased position, whereas the upper arm 508 cannot flex and remains in its position as shown in FIG. 6u. The position of the upper arm 508 is maintained by contact with the stylet hub 430. As the lower arm 507 flexes the upper and lower arms 508, 507 are pushed apart from each other. As tab 510 of the lower arm 507 reaches the end of the control rib 1405 (for example an edge of the control rib 1405 which may be a thin edge as shown), the lower arm 507 springs back to its un-deflected position and collides with the click rib 1406 making a "click" sound, as shown in FIG. 6v. The click rib 1406 is a feature of the housing 14', and in the present example, is formed integrally with the housing 14'. The click rib 1406 defines the other of the at least two components of an indicator mechanism of the present invention. As such, one of the at least two components of the indicator mechanism, the lower arm 507, is moveable within the housing 14' upon actuation of the moveable member such as the stylet 319. In one particular case, the click rib 1406 is a rigid member that functions as a non-biased component of the indicator mechanism that interacts with the lower arm 507 to provide an audible indication. The "click" sound indicates that the translation of the suture holder retrieving member, such as the stylet 319, to its desired translation distance, is complete. In such an embodiment, the arm 507 and rib 1406 may be understood to be components of a feature for providing an indication that the suture passing member has been advanced by a desired amount. For example, the "click" indicates that the stylet 319 has been advanced to a distance to allow it to engage with the suture holder, which will allow the stylet 318 to withdraw the suture holder along with it when it is retracted. As such, in accordance with an embodiment of the present invention, the indication mechanism provides an audible indication to indicate that the moveable member (e.g. stylet 319) has reached a desired distance in a medical device 100 where a moveable member (e.g. stylet 319) is moveable for transferring a component such as the suture trap or suture holder 316. More specifically, in the present embodiment of an indicator mechanism of the present invention, the interaction between the at least two components of the indicator mechanism (e.g. lower arm 507 and click rib 1406) occurs automatically upon actuation of the moveable member (e.g. stylet 319), thereby providing an automatic indication of the movement of the moveable member between the first and second positions. As shown in FIG. 6v, during the second actuation of the trigger, the depth selector 500' does not contact needle hub 130, allowing further translation of the stylet hub 430, which in turn allows the stylet to be advanced further for engaging with the suture holder. The translation of the stylet hub 430 is limited by a wire puller 1801 also shown in FIG. 6v. The trigger is then released allowing the stylet hub 430 to retract, allowing depth selector 500' to retract therewith. As illustrated in FIGS. 6w and 6x, the depth selector 500' is guided by control ribs 1405 and 1403 as it is retracted, allowing it to pivot back to its second position. In one such example, as the trigger is released after the second actuation, the tab 510 engages with and hits the lower surface 1403b of the control rib 1403 along the tapered section 1403t. The lower surface 1403b along the tapered section 1403t may additionally functions as a component of the indicator mechanism. More specifically, it is a feature that is integral with the housing 14' and functions as a rigid member that is a non-biased component of the indicator mechanism. In one such example the arm 507 functions as a moveable component of the indicator mechanism that interacts with the lower surface 1403b adjacent o along the taper 1403t of the control rib 1403 to provide an audible indication indicating that the moveable member such as stylet 319 has been retracted, for example to its initial or starting position. In one such example, as the trigger is released the stylet 319 retracts and the depth selector 500' and as such the arm 507 retract along with it. Once the tab 510 of the arm 507 hits the bottom surface 1403b adjacent or along the taper 1403t, the clicking sound indicates to the user that the second trigger actuation and release is compete and the moveable member such as stylet 319 as well as the needle are now in their initial or starting position.

Method of Use of an Automatic Needle Release Button Along with an Automatic Indicator Mechanism Comprising the Depth Selector Described Presently Above.

The automatic needle release button is usable with the automatic depth selector 500' and is usable therewith to allow the stylet 319 to advance with respect to the needle 116 past the needle 116 on each trigger pass to allow it to achieve the desired predetermined position required to achieve the target functionality. For example the needle release button 600' allows the stylet 319 to be advanced past the needle 116 in the first pass or trigger actuation to a first distance to deposit the suture knot 250 within the suture holder 316, where the depth selector 500' provides an indication confirming the stylet 319 has been advanced to the appropriate distance. The needle release button 600' additionally allows the stylet 319 to be advanced past the needle 116 in the second pass or trigger actuation to a second distance to retrieve the suture holder 316, where the depth selector 500' provides an indication again confirming that the stylet 319 has been advanced to the appropriate distance. The operation of the device 100 with the needle release button 600' is described further herein-below. During the first actuation of the trigger, as the stylet hub 430 translates distally, it allows the needle hub 130 to translate distally to the position shown in FIG. 6n. The ramp 402' of the stylet hub 430 engages ramp 602' of the button 600' that is coupled to the needle hub 130 as shown in FIG. 6n(i), pushing the needle hub 130 distally. The hook 604' of the button 600' is now positioned past the tab 1408 as shown in FIG. 6n(ii).

As the trigger is actuated further, the needle coupled to the needle hub 130 may encounter tissue resistance. In some embodiments, resistance may be observed as the needle abuts against the suture holder at the distal end of the device. This causes the ramp 402' on the stylet hub 430 to depress the ramp 602' on the needle hub 130 as shown in FIG. 6o(i). As tab 1408 is no longer preventing the hook 604' of the needle release button 600' from retracting, the needle release button 600' moves to its depressed or second position 600B', illustrated in FIGS. 6o(i) and 6o(ii). The stylet hub 430 and the needle hub 130 disengage from each other and are no longer operationally coupled. This allows the stylet hub 430 to advance relative to the needle hub 130 as shown in FIGS. 6o, 6p and 6q while keeping the needle release button 600' in its depressed position 600B'. This is further illustrated in FIGS. 6q(i) and 6q(ii) by the translation of ramp 402' of the stylet hub 430 past the needle release button 600 and the needle hub 130. In some embodiments, this may allow the stylet to be translated to deposit a suture within the suture holder at the distal tip of the device. The trigger is then released allowing the stylet hub 430 to retract or translate proximally. As shown in FIGS. 6r, 6r(i) and 6r(ii), as the stylet hub 430 is retracted it no longer depresses the needle release button 600' allowing it to return to its nominal position 600A. In some embodiments, as the needle release button 600' moves to its initial position 600A an audible indication may be provided to the user, for example, such as a 'clicking sound' that may be generated as the button 600A returns to its nominal position which may indicate to the user that the stylet 319 and the needle 116 have been retracted to their initial or starting position and the device 100 is ready to be actuated again. The needle hub 130 and the stylet hub 430 are coupled once again. As shown in FIGS. 6s, 6s(i) and 6s(ii), the stylet hub 430 and the needle hub 130 then translate further proximally. During this proximal translation, hook 604' of the needle release button 600' rides below tab 1408 of the housing 14' as shown in FIG. 6s(ii) and the button 600' remains in its nominal position 600A.

Upon second actuation of the trigger, the stylet hub 430 is then re-advanced. The interaction between ramp 402' of the stylet hub 430 and ramp 602' of the needle release button 600' (that is coupled to the needle hub 130), allows or forces the stylet hub 430 and the needle hub 130 to advance together. Hook 604' of the needle release button 600' rides below the tab 1408 until it is advanced beyond the tab 1408. As shown in FIGS. 6t, 6t(i) and 6t(ii), once the hook 604' is positioned past the tab 1408, further actuation of the trigger causes the stylet hub 430 to depress the needle release button 600' into its second or depressed position 600B'. In some embodiments, this is a result of the needle encountering resistance and not being able to advance. This causes the needle hub 130 to be decoupled from the stylet hub 430, allowing the stylet hub 430 to advance relative to the needle hub 130. As the trigger is actuated further, the stylet hub 430 advances further relative to the needle hub 130, as shown previously in FIGS. 6u and 6v and is further illustrated in FIGS. 6v(i), and 6v(ii). In one particular embodiment, the stylet hub 430 is advanced to allow the stylet to engage the suture holder at the distal tip to allow the suture holder to be retracted with the stylet. As the trigger is then released the stylet hub 430 and the needle 130 retract together as a unit. The needle release button 600' remains in its depressed position 600B' and hook 604' of the needle release button 600' rides above the tab 1408 as shown in FIG. 6w and further illustrated in FIGS. 6w(i) and 6w(ii). When the trigger is fully released, the stylet hub 430 and needle hub 130 have been retracted proximally as shown in FIG. 6x, and the stylet withdraws the suture holder proximally as it is retracted. The needle release button 600' remains in its depressed or second position 600B'. As outlined previously herein above, the automatic needle release button 600' is usable with the automatic indicator mechanism comprising an automatic depth selector 500' which provides an indication to the user that the stylet 319 has advanced to the appropriate desired distance, for example to deposit the suture knot 250 within the suture holder 316 or to retrieve the suture holder 316 from the distal tip 12.

As a general note: in some of the embodiments described above with respect to FIGS. 6m-6x, the springs illustrated in the figures are shown in their uncompressed state but as would be known to one skilled in the art the springs will be compressed between the respective components.

Thus, embodiments of the present invention comprise a medical device having a moveable member, that is a member operable to be advanced, translated, actuated or otherwise moved, and an indicator that provides information about the absolute or relative location or position of the moveable member. In some embodiments, the moveable member is used, for example, to deposit a component within a region of tissue.

In some embodiments, the indicator has at least two states, a first state and a second state. In some such embodiments, the indicator automatically changes or transitions between the first state and the second state when the moveable member is advanced from its initial position to another position, for example by a predetermined or desired distance or to a specific position relative to another portion of the medical device.

In one broad aspect embodiments of the present invention provide a medical device comprising: a moveable member that is moveable between a first position and a second position for transferring a component; and an indicator mechanism coupled to the moveable member for indicating a position of said moveable member, said indicator mechanism comprising at least two components that are functional to interact with one another to produce an indication; wherein the interaction between the at least two components occurs automatically upon actuation of the moveable member, thereby providing an automatic indication of the movement of the moveable member between the first and second positions.

As a feature of this broad aspect, the indication comprises an audible indication.

As another feature of this broad aspect, one of the at least two components of the indicator mechanism is coupled to the moveable member. In one such example, one of the at least two components is indirectly coupled to the moveable member.

In some embodiments, one of the at least two components is moveable within the housing upon actuation of the moveable member. In some such embodiments, the device comprises a housing, wherein another of the at least two components comprises a feature of the housing.

As another feature of this broad aspect, one of the at least two components comprises a biased component and the other of the at least two components comprises a non-biased component. As an example of this feature, the biased component comprises a deflectable member and the non-biased component comprises a rigid member.

In one particular embodiment, the deflectable member comprises a deflectable arm that is a part of a depth selector. In one such embodiment, the rigid member comprises a feature that is integral with the housing.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A medical device comprising:
   a moveable member that is moveable between an initial position and multiple predetermined positions for transferring at least one component there-between;
   an actuator coupled to the moveable member for actuating said moveable member between the initial position and the multiple predetermined positions; and
   at least one automatic indicator mechanism coupled to the moveable member for providing multiple indications, each for indicating movement of said moveable member between the initial position and one of said multiple predetermined positions, wherein the at least one indicator mechanism comprises multiple indicator mechanisms, each for providing one of said multiple indications, and
   wherein the multiple indicator mechanisms comprise a first indicator mechanism for providing a first indication and a second indicator mechanism for providing a second indication;
   said first indication for indicating movement of said moveable member between said initial position and a first predetermined position from said multiple predetermined positions, said movement being sufficient to transfer at least a first component of said at least one component between said initial position and the first predetermined position; and said second indication for indicating movement of said moveable member between said initial position and a second predetermined position from said multiple predetermined positions, said movement being sufficient to transfer the first component between said initial position and the second predetermined position.

2. The medical device of claim 1, wherein at least one of the multiple indications comprises an audible indication.

3. The medical device of claim 1, wherein the at least one indicator mechanism comprises a single indicator mechanism for providing each of said multiple indications.

4. The medical device of claim 1, wherein the at least one indicator mechanism comprises at least two components that are functional to interact with one another to produce the multiple indications;

wherein the interaction between the at least two components occurs automatically upon actuation of the moveable member, thereby providing an automatic indication of the movement of the moveable member between the initial position and one of said multiple predetermined positions.

5. The medical device of claim 4, wherein one of the at least two components of the at least one indicator mechanism is coupled to the moveable member.

6. The medical device of claim 5, wherein said one of the at least two components is indirectly coupled to the moveable member.

7. The medical device of claim 6, wherein said one of the at least two components is moveable within a housing of the medical device upon actuation of the moveable member.

8. The medical device of claim 7 wherein the device comprises the housing, wherein another of the at least two components comprises a feature of the housing.

9. The medical device of claim 8, wherein the said one of the at least two components comprises a biased component and the other of the at least two components comprises a non-biased component.

10. The medical device of claim 9, wherein the biased component comprises a deflectable member and the non-biased component comprises a rigid member.

11. The medical device of claim 10, wherein the deflectable member comprises a deflectable arm that is a part of a depth selector.

12. The medical device of claim 11, wherein the rigid member comprises a feature that is integral with the housing.

13. The medical device of claim 1, wherein the at least one indicator mechanism comprises multiple indicator mechanisms, each for providing one of said multiple indications, wherein each of said multiple indicator mechanisms comprises at least two components.

14. The medical device of claim 13, wherein at least two of said indicator mechanisms share a component from each of their respective at least two components.

* * * * *